US011135186B2

(12) United States Patent
Cooley et al.

(10) Patent No.: US 11,135,186 B2
(45) Date of Patent: Oct. 5, 2021

(54) REGULATORS OF THE ENDOPLASMIC RETICULUM PROTEOSTASIS NETWORK

(71) Applicant: The Scripps Research Institute, La Jolla, CA (US)

(72) Inventors: Christina Cooley, San Antonio, TX (US); Jeffery W. Kelly, Solana Beach, CA (US); Ryan Paxman, San Diego, CA (US); Lars Plate, San Diego, CA (US); R. Luke Wiseman, Chula Vista, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 16/066,555

(22) PCT Filed: Dec. 29, 2016

(86) PCT No.: PCT/US2016/069284
§ 371 (c)(1),
(2) Date: Jun. 27, 2018

(87) PCT Pub. No.: WO2017/117430
PCT Pub. Date: Jul. 6, 2017

(65) Prior Publication Data
US 2019/0008809 A1    Jan. 10, 2019

Related U.S. Application Data

(60) Provisional application No. 62/272,233, filed on Dec. 29, 2015.

(51) Int. Cl.

| | |
|---|---|
| *A61K 31/167* | (2006.01) |
| *A61K 31/506* | (2006.01) |
| *A61K 31/381* | (2006.01) |
| *A61K 31/415* | (2006.01) |
| *A61K 31/4184* | (2006.01) |
| *A61K 31/42* | (2006.01) |
| *A61K 31/422* | (2006.01) |
| *A61K 31/428* | (2006.01) |
| *A61K 31/437* | (2006.01) |
| *A61K 31/4439* | (2006.01) |
| *A61K 31/454* | (2006.01) |
| *A61K 31/497* | (2006.01) |
| *A61K 31/4245* | (2006.01) |
| *A61K 31/47* | (2006.01) |
| *A61K 31/4196* | (2006.01) |
| *A61K 31/53* | (2006.01) |
| *A61K 31/4178* | (2006.01) |
| *A61K 31/137* | (2006.01) |
| *A61K 31/50* | (2006.01) |
| *A61K 31/4174* | (2006.01) |
| *A61K 31/136* | (2006.01) |
| *A61K 31/429* | (2006.01) |
| *A61K 31/5377* | (2006.01) |

(52) U.S. Cl.
CPC .......... *A61K 31/167* (2013.01); *A61K 31/136* (2013.01); *A61K 31/137* (2013.01); *A61K 31/381* (2013.01); *A61K 31/415* (2013.01); *A61K 31/4174* (2013.01); *A61K 31/4178* (2013.01); *A61K 31/4184* (2013.01); *A61K 31/4196* (2013.01); *A61K 31/42* (2013.01); *A61K 31/422* (2013.01); *A61K 31/428* (2013.01); *A61K 31/429* (2013.01); *A61K 31/4245* (2013.01); *A61K 31/437* (2013.01); *A61K 31/4439* (2013.01); *A61K 31/454* (2013.01); *A61K 31/47* (2013.01); *A61K 31/497* (2013.01); *A61K 31/50* (2013.01); *A61K 31/506* (2013.01); *A61K 31/53* (2013.01); *A61K 31/5377* (2013.01)

(58) Field of Classification Search
CPC .. A61K 31/167; A61K 31/381; A61K 31/415; A61K 31/4184
See application file for complete search history.

(56) References Cited

U.S. PATENT DOCUMENTS

| | | |
|---|---|---|
| 7,012,159 B1 | 3/2006 | Hidaka et al. |
| 2009/0203605 A1 | 8/2009 | Segatori et al. |
| 2013/0344530 A1 | 12/2013 | Oyadomari |

FOREIGN PATENT DOCUMENTS

| | | |
|---|---|---|
| WO | WO-2013192165 A2 | 12/2013 |
| WO | WO-2017117430 A1 | 7/2017 |

OTHER PUBLICATIONS

Sanchorawala. Light-Chain (AL) Amyloidosis: Diagnosis and Treatment. Clin. J. Am. Soc. Nephrol, 1: 1331-1341, 2006.*
Gatt & Palladini. Light chain amyloidosis 2012: a new era. British Journal of Haematology, 2013, 160, 582-598.*
Nakawatase et al. "Alzheimer's Disease and Related Dementia." Cecil's Textbook of Medicine. (Twenty-First Edition, vol. 1, W. B. Saunders Company, 2000, pp. 2042-2045.*
Greicius et al. "Presenile Dementia Syndrome: an update on taxonomy and diagnosis." Journal of Neurol. Neurosurg. Psychiatry, 2002; 72:691-700.*

(Continued)

*Primary Examiner* — Anna Pagonakis
(74) *Attorney, Agent, or Firm* — Rimon, P.C.; Dale L. Rieger

(57) ABSTRACT

The invention provides compounds for activating the activating transcription factor 6 (ATF6) arm of the unfolded protein response (UPR), or activating the transcriptional targets of ATF6, in the endoplasmic reticulum of a cell, the compounds being of any of formulas (I) through (IX) as described herein. The compounds can be used for treatment of conditions involving gain-of-toxic-function and loss-of-function folding disorders including lysosomal storage diseases, antitrypsin-associated emphysema and similar diseases. These molecules are also expected to have disease-ameliorating effects in Alzheimer's disease and diabetes.

2 Claims, 33 Drawing Sheets
Specification includes a Sequence Listing.

(56) References Cited

OTHER PUBLICATIONS

Gauthier et al. "Alzheimer's disease: Current Knowledge, Management and Research." Can. Med. Assoc. J. 1997; 157(8): 1047-1052.*
Gasparini et al. "Peripheral Markers in Testing Pathophysiological Hypotheses and Diagnosis Alzheimer's Disease." FASEB. J. 12, 1998: 17-34.*
Quinton et al. Cystic fibrosis: a disease in electrolyte transport. FASEB, vol. 4, Jul. 1990.*
Boucher. New concepts of the pathogenesis of cysti fibrosis lung disease. Eur. Respir. J. 2004; 23: 146-153.*
"International Application Serial No. PCT US2016 069284, International Preliminary Report on Patentability dated Jul. 12, 2018", 6 pages.
"International Application Serial No. PCT/US2016/069284, International Search Report dated May 8, 2017", 5 pgs.
"International Application Serial No. PCT/US2016/069284, Invitation to Pay Add'l Fees and Partial Search Rpt dated Mar. 7, 2017", 2 pgs.
"International Application Serial No. PCT/US2016/069284, Written Opinion dated May 8, 2017", 4 pgs.
"N-(2-hydroxy-5-methylphenyl)-3-phenylpropanamide", Compound Summary for CID 882909, Pub Chem: Open Chemistry Database, [Online]. Retrieved from the Internet: <https://pubchem.ncbi.nlm.nih.gov/compound/882909>, (Jul. 9, 2005), 13 pgs.
"STK224171", Compound Summary for CID 892165, Pub Chem: Open Chemistry Database, [Online]. Retrieved from the Internet: <https://pubchem.ncbi.nlm.nih.gov/compound/892165>, (Jul. 9, 2005), 14 pgs.
Ashraf, Ghulam MD, et al., "Protein misfolding and aggregation in Alzheimer's disease and Type 2 Diabetes Mellitus", CNS Neurol Disord Drug Targets, (Dec. 28, 2016), 27 pgs.
Detoma, Alaina S, et al., "Misfolded Proteins in Alzheimer's Disease and Type II Diabetes", Chem Soc Rev., (Jan. 21, 2012), 608-621.
"European Application Serial No. 16882684.0, Communication pursuant to Rule 164(1) EPC dated Aug. 7, 2019", 19 pgs.
Cooley, Christina B, et al., "Unfolded protein response activation reduces secretion and extracellular aggregation of amyloidogenic immunoglobulin light chain", PNAS, vol. 111, No. 36, (Sep. 9, 2014), 13046-13051.
Fu, Suneng, et al., "Phenotypic assays identify azoramide as a small-molecule modulator of the unfolded protein response with antidiabetic activity", Science Translational Medicine, vol. 7, No. 292, (Jun. 17, 2015), 16 pgs.
Kudo, T, et al., "A molecular chaperone inducer protects neurons from ER stress", Cell Death and Differentiation, vol. 15, No. 2, (Nov. 30, 2007), 364-375.
Paxman, Ryan, et al., "Pharmacologic ATF6 activating compounds are metabolically activated to selectively modify endoplasmic reticulum proteins", Elife, vol. 7, (Aug. 7, 2018), 29 pgs.
Plate, Lars, et al., "Small molecule proteostasis regulators that reprogram the ER to reduce extracellular protein aggregation", Elife, vol. 5, (Jul. 20, 2016), 49 pgs.
Shoulders, Matthew D, et al., "Stress-Independent Activation of XBP1s and/or ATF6 Reveals Three Functionally Diverse ER Proteostasis Environments", Cell Reports 3, (Apr. 25, 2013), 1279-1292.

Hovey, B. M., et al., "Preclinical development of siRNA therapeutics for AL amyloidosis", Gene Therapy (2011) 18, 1150-1156, (May 12, 2011), 1150-1156.
Lachmann, Helen J., et al., "Outcome in systemic AL amyloidosis in relation to changes in concentration of circulating free immunoglobulin light chains following chemotherapy", British Journal of Haematology, 2003, 122, 78-84, (Feb. 3, 2003), 78-84.
Mahmood, Shameem, et al., "Update on treatment of light chain amyloidosis", Haematologica 99(2), (2014), 209-221.
Ohno, Satoko, et al., "The Antisense Approach in Amyloid Light Chain Amyloidosis: Identification of Monoclonal Ig and Inhibition of Its Production by Antisense Oligonucleotides in In Vitro and In Vivo Models", J Immunol 2002; 169:4039-4045, (Jul. 24, 2002), 4039-4045.
Phipps, Jonathan E., et al., "Inhibition of pathologic immunoglobulin-free light chain production by small interfering RNA molecules", Experimental Hematology 2010;38:1006-1013, (Jul. 6, 2010), 1006-1013.
Sanchorawala, V., et al., "Serum free light-chain responses after high-dose intravenous melphalan and autologous stem cell transplantation for AL (primary) amyloidosis", Bone Marrow Transplantation (2005) 36, 597-600, (Jul. 25, 2005), 597-600.
"European Application Serial No. 16882684.0, Communication pursuant to Article 94(3) EPC dated Oct. 23, 2020", 8 pgs.
Dubois, Bruno, et al., "Preclinical Alzheimer's disease: Definition, natural history, and diagnostic criteria", Alzheimers Dement. Mar. 2016; 12(3): 292-323, (Mar. 2016), 292-323.
Genereux, Joseph C., et al., "Unfolded protein response-induced ERdj3 secretion links ER stress to extracellular proteostasis", The EMBO Journal (2015) 34: 4-19, (Oct. 31, 2014), 4-19.
Hayashi, Takeshi, et al., "Induction of GRP78 by Ischemic Preconditioning Reduces Endoplasmic Reticulum Stress and Prevents Delayed Neuronal Cell Death", Journal of Cerebral Blood Flow & Metabolism, 23:949-961 (2003), (Apr. 30, 2003), 949-961.
Hoshino, Tatsuya, et al., "Endoplasmic reticulum chaperones inhibit the production of amyloid-Beta peptides", Biochem. J. (2007) 402, 581-589, (Nov. 29, 2006), 581-589.
Oida, Y., et al., "Induction of BiP, an ER-resident protein, prevents the neuronal death induced by transient forebrain ischemia in gerbil", Brain Research, vol. 1208, 217-224 [abstract only], (May 7, 2008), 217-224.
Ouyang, Yi-Bing, et al., "Overexpressing GRP78 influences Ca2+ handling and function of mitochondria in astrocytes after ischemia-like stress", Mitochondrion. Mar. 2011; 11(2): 279-286, (Mar. 2011), 279-286.
Yang, Lucie, et al., "Brain Amyloid Imaging—FDA Approval of Florbetapir F18 Injection", N. Engl J Med 367:10, 885-887, (Sep. 6, 2012), 885-887.
Yoshikawa, Akifumi, et al., "Deletion of Atf6alpha impairs astroglial activation and enhances neuronal death following brain ischemia in mice", Journal of Neurochemistry (2015), 132(3): 342-353, (2015), 342-353.
Yu, Zaifang, et al., "The Endoplasmic Reticulum Stress-Responsive Protein GRP78 Protects Neurons Against Excitotoxicity and Apoptosis: Suppression of Oxidative Stress and Stabilization of Calcium Homeostasis", Experimental Neurology, vol. 155, Issue 2 [abstract only], (Feb. 1999), 302-314.

* cited by examiner

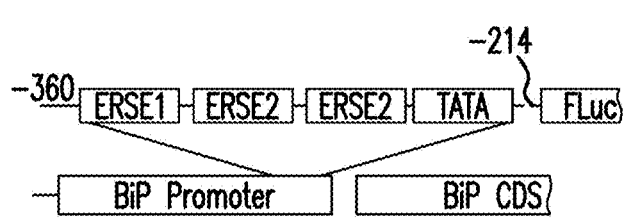
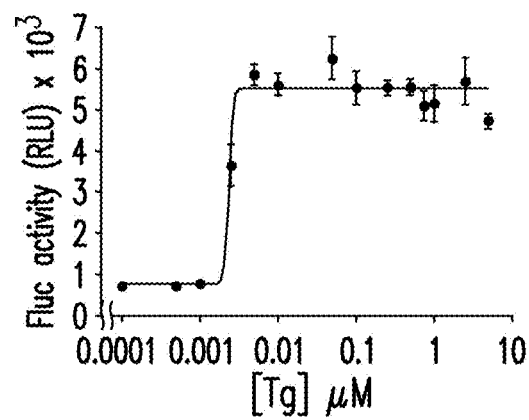
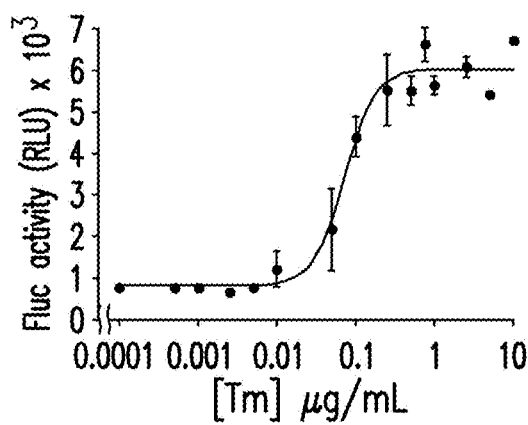
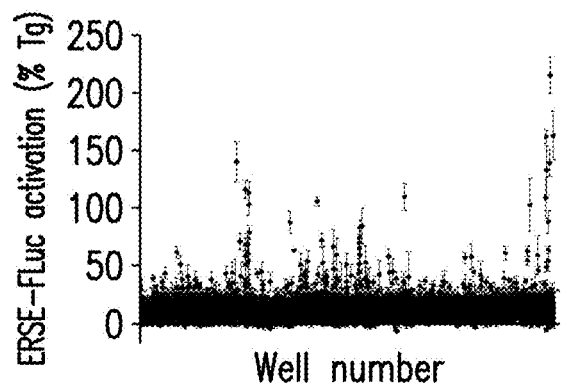
FIG. 1A
FIG. 1B
FIG. 1C
FIG. 1D

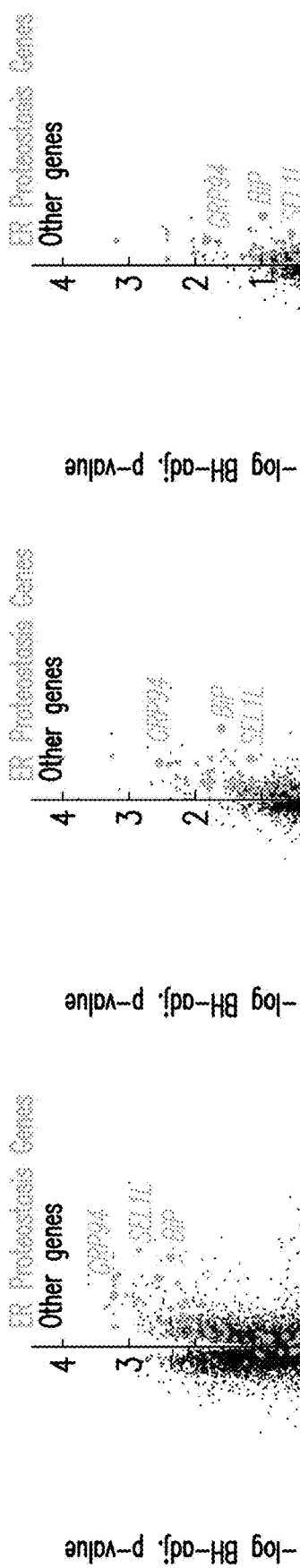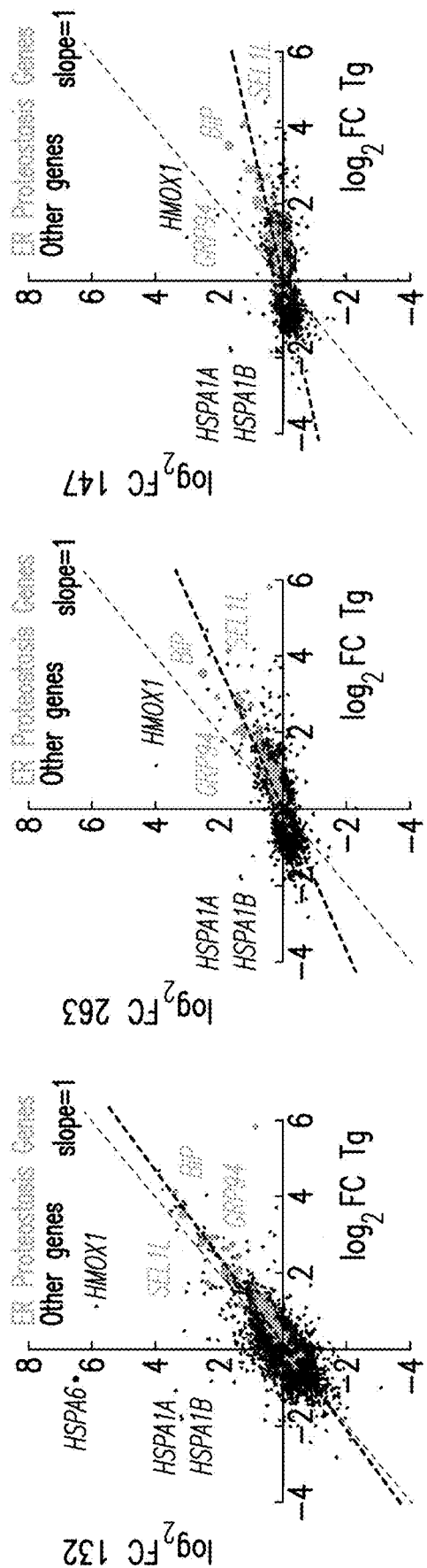

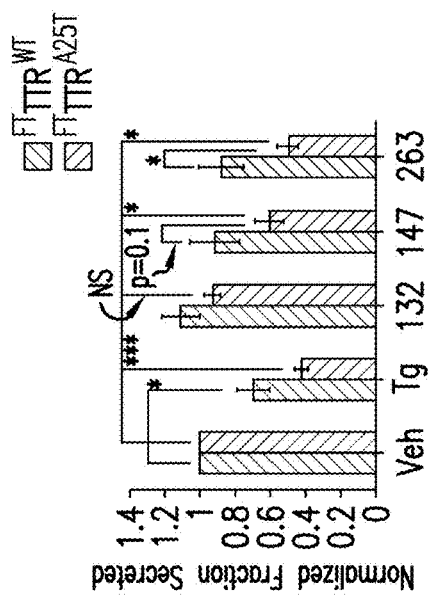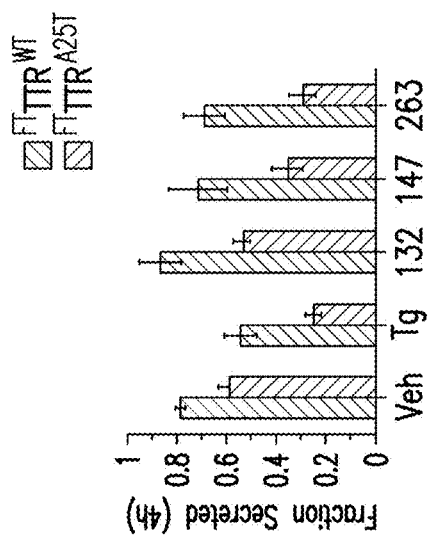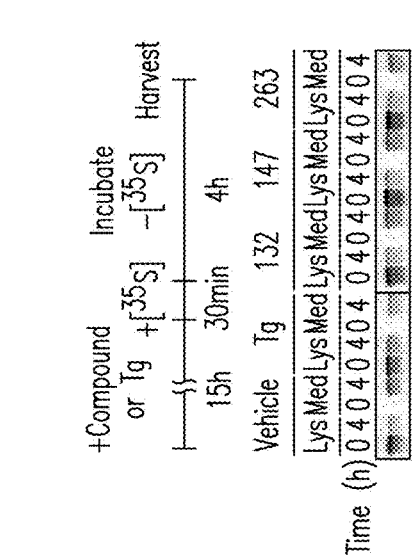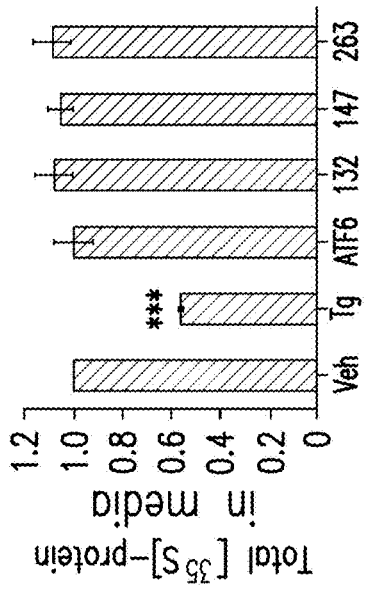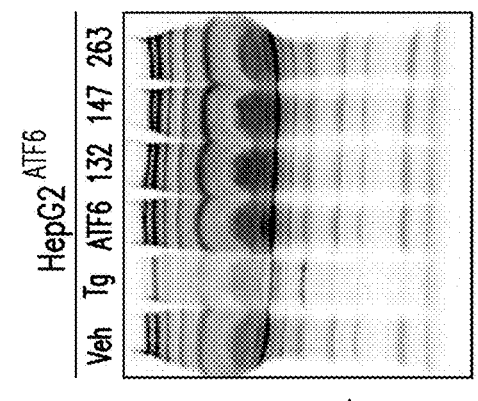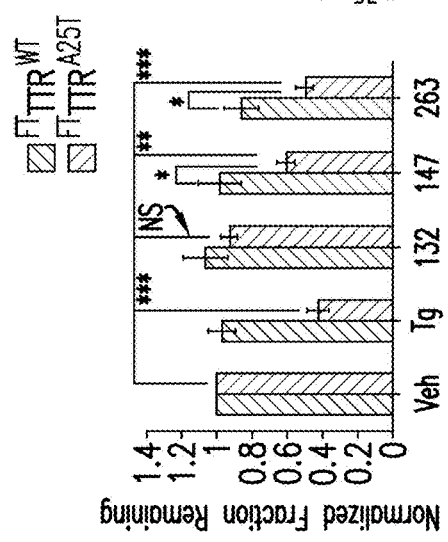

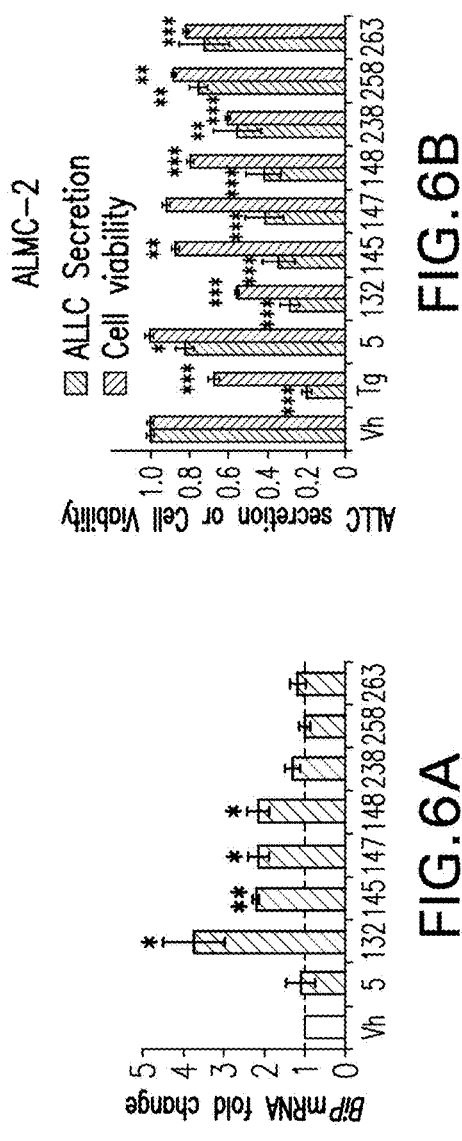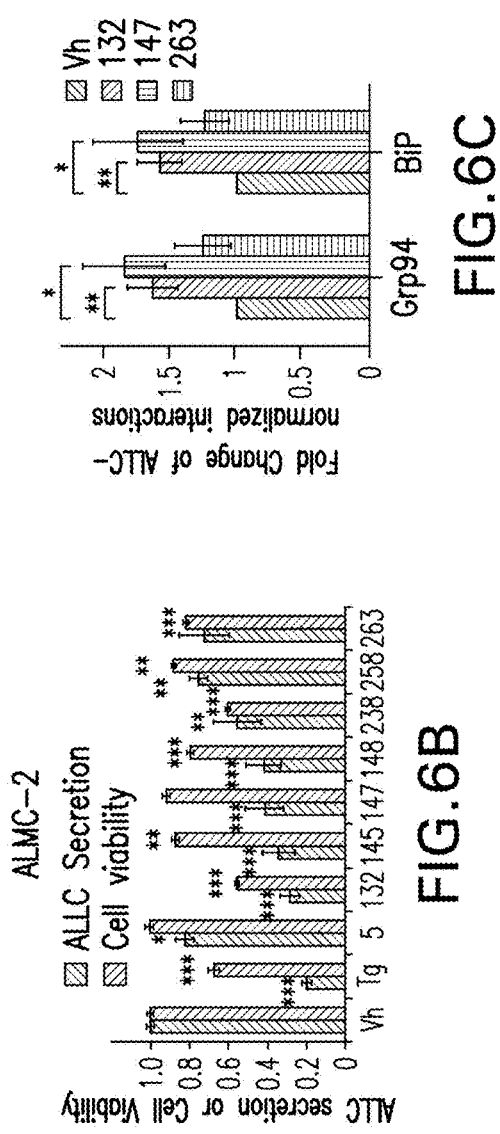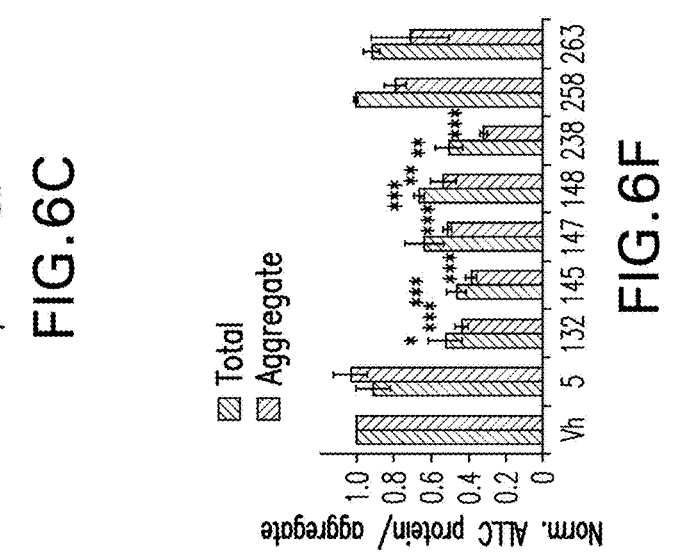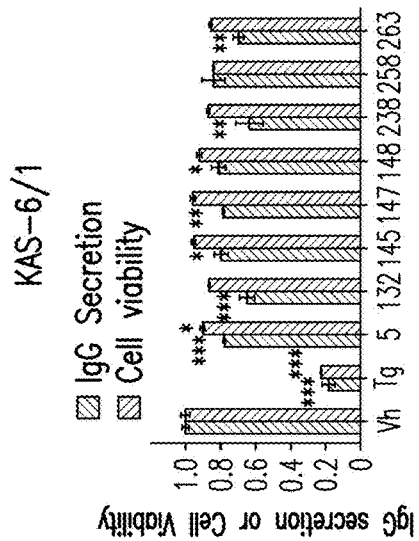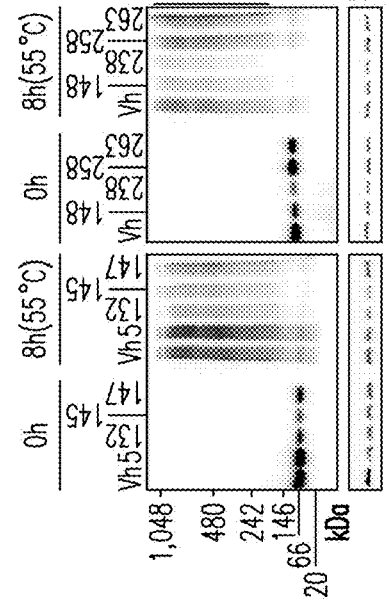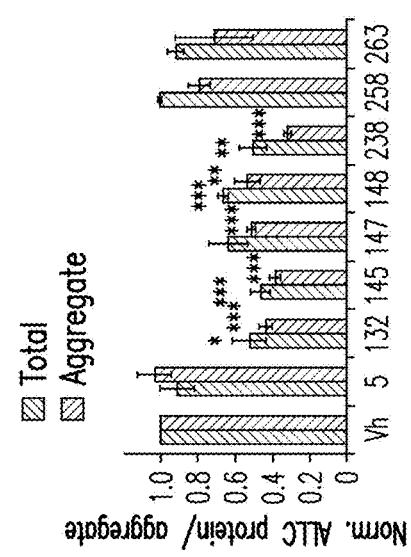

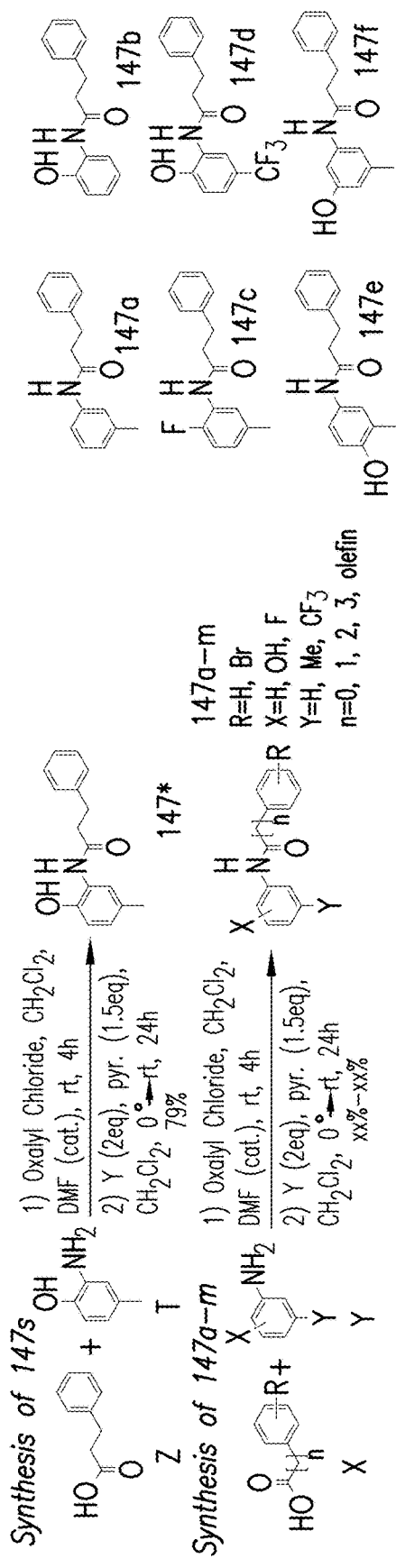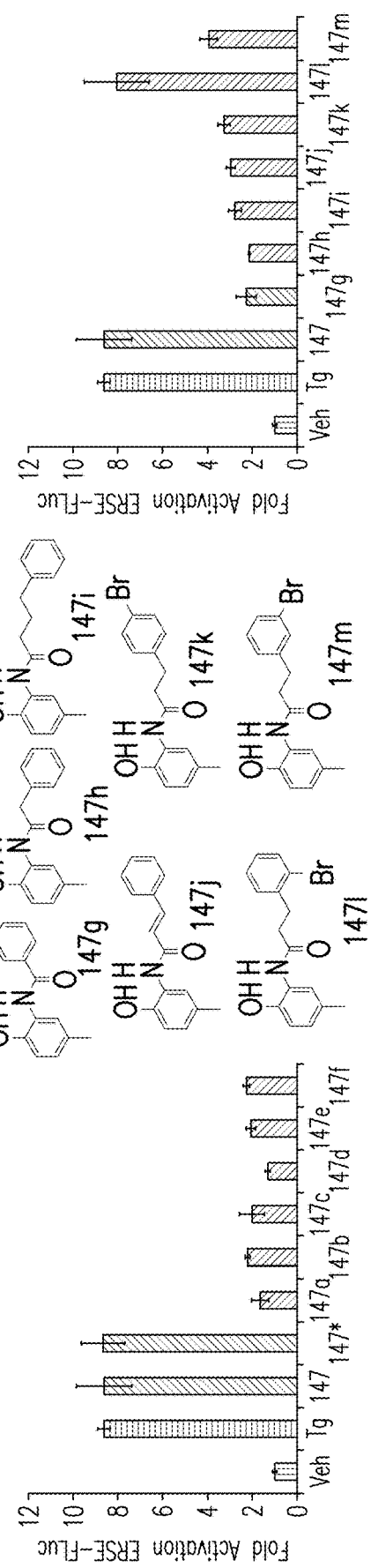
FIG. 7A  FIG. 7B  FIG. 7C  FIG. 7D  FIG. 7E

AA147 and AA263 analogues

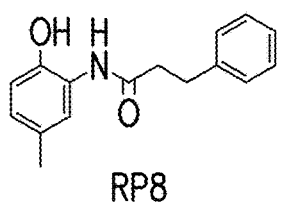
RP8
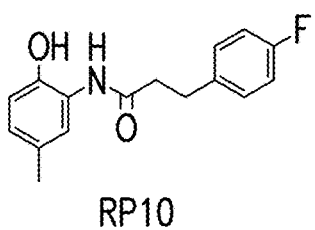
RP10
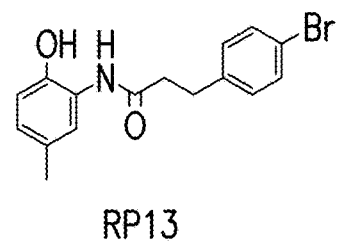
RP13
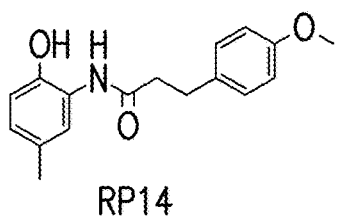
RP14
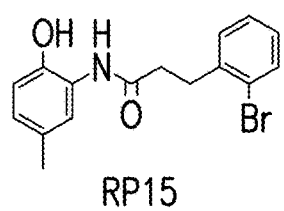
RP15
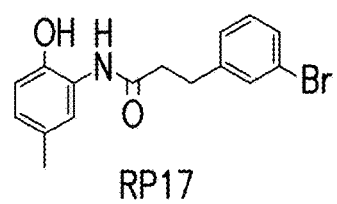
RP17
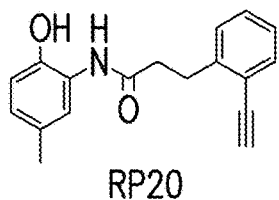
RP20
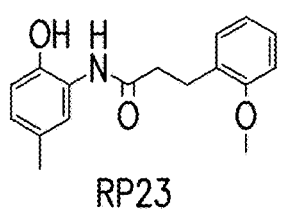
RP23
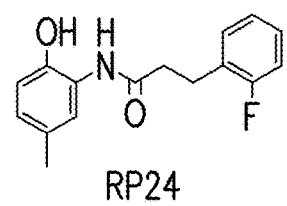
RP24
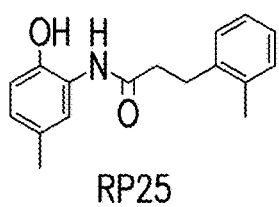
RP25
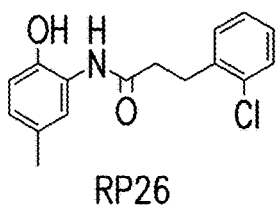
RP26
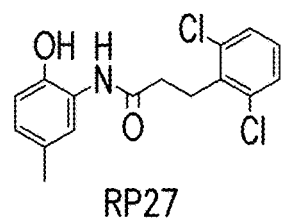
RP27
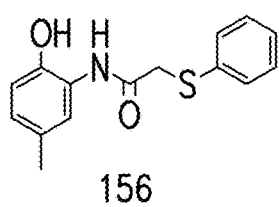
156
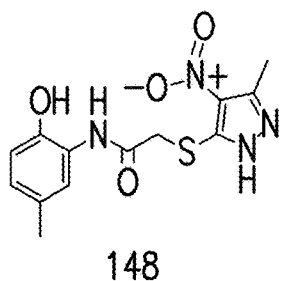
148
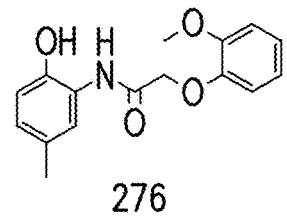
276
FIG.9A

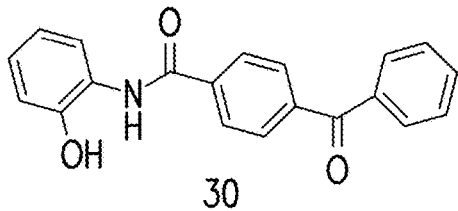
30
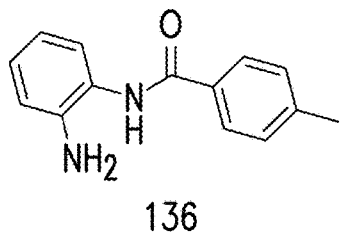
136
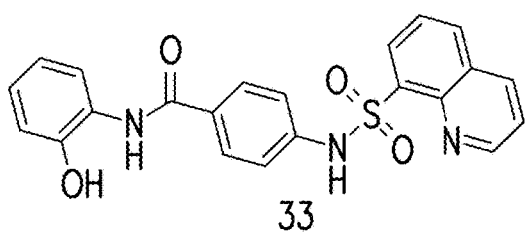
33
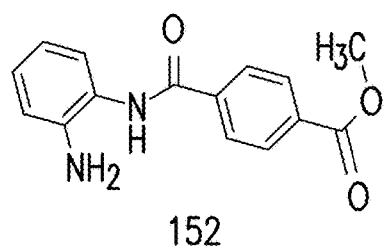
152
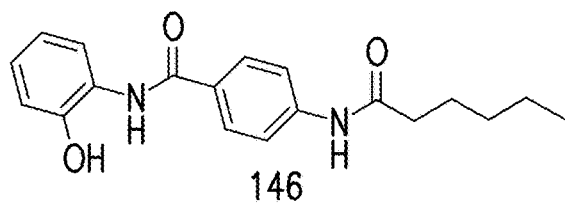
146
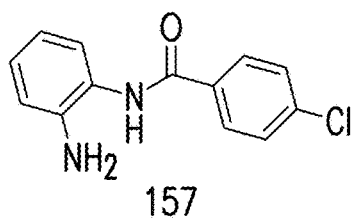
157
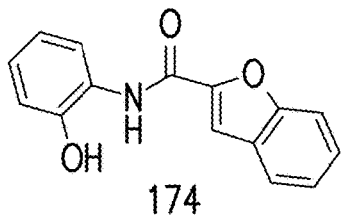
174
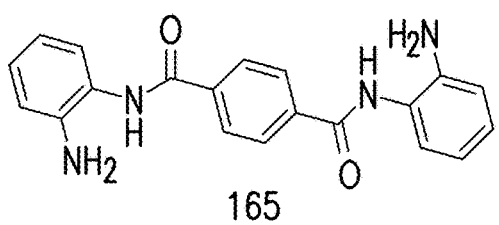
165
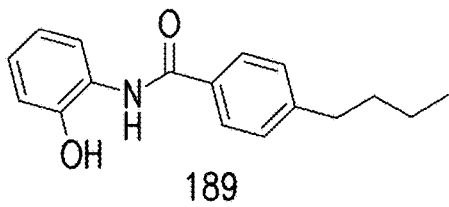
189
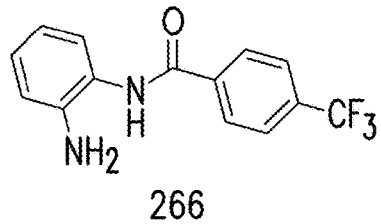
266
FIG.17A

REGULATORS OF THE ENDOPLASMIC RETICULUM PROTEOSTASIS NETWORK

CROSS-REFERENCE TO RELATED APPLICATIONS

This application is a national stage application under 35 U.S.C. 371 of PCT/US2016/069284, filed on Dec. 29, 2016, and published as WO 2017/117430 on Jul. 6, 2017, which claims the benefit of priority to U.S. provisional application Ser. No. 62/272,233, filed on Dec. 29, 2015 which applications and publication are incorporated by reference herein in their entireties.

STATEMENT OF GOVERNMENT SUPPORT

This invention was made with government support under grant numbers AG042259, AG046495, DK046335, and DK102635 awarded by the National Institutes of Health. The government has certain rights in the invention.

BACKGROUND

Nearly ⅓ of the human proteome is targeted to the endoplasmic reticulum (ER) for folding and trafficking to downstream environments of the secretory pathway, including the plasma membrane and the extracellular space. These proteins engage ER-localized protein homeostasis (or proteostasis) factors such as chaperones and folding enzymes that facilitate the proper folding of the secreted proteome[1-3]. Folded proteins are packaged into COPII vesicles for trafficking to downstream environments of the secretory pathway[4]. Proteins unable to fold in the ER are identified by ER proteostasis components comprising degradation pathways and directed towards the proteasome (via ER-associated degradation) or the lysosome for degradation[3,5]. Partitioning of proteins between ER protein folding and degradation pathways prevents the trafficking of destabilized proteins that could misfold and/or aggregate into proteotoxic conformations in downstream secretory environments[3,6].

Despite the general effectiveness of ER proteostasis pathways, many protein misfolding diseases result from imbalances in the partitioning of destabilized mutant proteins between ER protein folding and trafficking pathways versus degradation pathways. Gain-of-proteotoxicity phenotypes can result from the inability to efficiently degrade destabilized mutant proteins, facilitating their intracellular aggregation. This is observed in the case of rhodopsin and α-1-antitrypsin (A1AT) mutants resulting in retinitis pigmentosa and liver disease, respectively[7-9]. Alternatively, proteotoxicity can result from the efficient secretion of a properly folded, but destabilized, protein that subsequently misfolds and aggregates in the extracellular space leading to demise of post-mitotic tissue. Examples include the transthyretin (TTR) or light chain (AL) systemic amyloid diseases[10,11].

Considering the importance of ER proteostasis imbalance in these maladies, we posit that adapting ER proteostasis network (PN) capacity is a potential therapeutic strategy to intervene in gain-of-proteotoxicity disorders as well as loss-of-function diseases[12-15]. ER PN remodeling can be achieved by activation of the unfolded protein response (UPR), comprising three signaling pathways activated downstream of the ER stress sensing proteins IRE1, ATF6, and PERK[16]. In response to the ER accumulation of misfolded proteins (i.e., ER stress), these sensors are activated, resulting in the remodeling of the ER PN predominantly through the activity of the UPR-associated transcription factors XBP1s and/or ATF6. XBP1s is activated through a mechanism involving IRE1-dependent splicing of XBP1 mRNA to remove a 26-nt intron. The spliced mRNA product encodes the active basic Leucine Zipper Domain (bZIP) transcription factor XBP1s[17]. ATF6 is activated by trafficking of the full-length ATF6 protein to the Golgi. Here, ATF6 is proteolytically processed by Site-1 Protease (S1P) and Site-2 Protease (S2P) to release the N-terminal active bZIP ATF6 transcription factor domain to the cytoplasm, allowing its nuclear localization[18].

The XBP1s and ATF6 transcription factors induce distinct, but overlapping, sets of genes that encode ER PN components[19-21]. Thus, activating XBP1 s and/or ATF6 provides a mechanism to sensitively adapt the ER PN and alter the fate of disease-associated proteins[14,15]. Genetic activation of IRE1/XBP1s and/or ATF6 reduces intracellular accumulation of mutant rhodopsin[22,23]. Similarly, ATF6 activation attenuates intracellular aggregation of the A1AT Z-variant[24]. Furthermore, stress-independent activation of a ligand-regulated ATF6 attenuates the secretion and extracellular aggregation of destabilized, disease-associated amyloidogenic TTR variants or amyloidogenic immunoglobulin light chain (LC) sequences, without significantly impacting secretion of stable, non-amyloidogenic TTR, energetically normal LCs, or the global endogenous secreted proteome[21,25,26]. These results suggest that small molecule-mediated activation of IRE1/XBP1s and/or ATF6 arms of the UPR could adapt the ER PN and attenuate the aberrant secretion and/or aggregation of proteins involved in gain-of-toxicity protein misfolding diseases[14,15].

Currently, few small molecules exist to preferentially activate the IRE1/XBP1s or ATF6 arms of the UPR[14,15,27]. Traditionally, these pathways are activated using small molecules that induce ER stress such as the SERCA inhibitor thapsigargin (Tg) or the inhibitor of N-linked glycosylation tunicamycin (Tm)[14,15]. While these molecules are useful for elucidating UPR signaling pathways, chronic addition of these ER stressors induce apoptosis predominantly through the PERK arm of the UPR[28,29]. Small molecule kinase inhibitors and ATP mimetics have been shown to activate the IRE1/XBP1s arm of the UPR[30-32], although the specificity for these molecules for IRE1 relative to other kinases remains to be established. Alternatively, the small molecule BIX induces expression of the ATF6-target gene BiP through an ATF6-dependent mechanism, but does not significantly induce expression of other ATF6 target genes such as GRP94, p58$^{IPK}$ and PDIA4, which likely limits its utility for ER PN remodeling in protein misfolding diseases,[33] as such molecules would alter the stoichiometry of the ER proteostasis network components, likely compromising overall proteostasis in the ER.

SUMMARY

Here, we used cell-based high-throughput screening (HTS) combined with a luminescent transcriptional reporter to identify new small molecule ER proteostasis regulators that selectively activate the ATF6 arm of the UPR. Transcriptional and proteomic profiling analyses demonstrate that a subset of the molecules discovered preferentially induce ATF6-dependent remodeling of the ER PN in the absence of global UPR activation. Addition of these molecules to mammalian cells phenocopies genetic ATF6 activation in their ability to preferentially decrease the secretion and proteotoxic aggregation of destabilized, amyloidogenic proteins without significantly affecting secretion of stable, non-amyloidogenic proteins or the global endogenous secreted proteome. Through these efforts, a first-generation library of small molecule ER proteostasis regulators was established that adapt the ER PN through preferential ATF6 activation. These compounds, as exemplified in the formulas (I) through (IX) as disclosed herein, are suitable for treatment of a protein misfolding disease(s) by preferentially activating the activating transcription factor 6 (ATF6) arm of the unfolded protein response (UPR) in the endoplasmic reticulum of a cell. Specific examples of these generic formulas are disclosed and claimed. The protein misfolding disease can comprise a gain-of-proteotoxicity protein aggregation disease including Alzheimer's disease, light chain amyloidosis, or a transthyretin amyloidosis, or retinitis pigmentosa associated with mutant rhodopsin aggregation, or antitrypsin associated liver cancer. Alternatively, the protein misfolding disease can comprise a loss-of-function protein misfolding disease including a lysosomal storage disease, Cystic Fibrosis, or antitrypsin associated emphysema. There is increased recognition that diseases categorized as "loss-" or "gain-" of function likely exhibit bot attributes. In other embodiments, the protein misfolding disease is associated with secretory pathway protein homeostasis stresses, including diabetes, metabolic disorders, eye disease, and cardiovascular disease, which can be treated using methods disclosed and claimed herein.

BRIEF DESCRIPTION OF THE FIGURES

FIG. 1—High-throughput screen to identify small molecule ER proteostasis regulators FIG. 1A. Schematic of the ERSE-FLuc reporter used in our HTS approach.

FIG. 1B. Activation of firefly luciferase (FLuc) luminescence in HEK293T-Rex cells stably expressing ERSE-FLuc treated with the indicated concentration of thapsigargin (Tg) for 18 h. Error bars represent standard deviation for n=3 replicates.

FIG. 1C. Activation of FLuc luminescence in HEK293T-Rex cells stably expressing ERSE-FLuc treated with the indicated concentration of tunicamycin (Tm) for 18 h. Error bars represent standard deviation for n=3 replicates.

FIG. 1D. Plot showing ERSE-FLuc activation in HEK293T-Rex cells stably expressing ERSE-FLuc treated with the 13,750 small molecule ER proteostasis activators identified in the primary screen (6.8 µM; 18 h). Luminescence is shown as % signal relative to Tg treatment (500 nM; 18 h). Error bars show standard deviation from n=3 replicates. The dashed gray line shows 25.1% Tg activity.

FIG. 3—Small molecule ER proteostasis regulators preferentially induce UPR-regulated ER proteostasis genes to varying extents.

FIG. 3A-C. Volcano plots showing $\log_2$ mRNA fold-change (relative to vehicle-treated controls) versus $-\log_{10}$ Benjamini Hochberg (BH) adjusted p-value for mRNAs in HEK293T-Rex cells treated with small molecule ER proteostasis regulators 132 (FIG. 3A), 263 (FIG. 3B) or 147 (FIG. 3C) (all treated at 10 µM, 6 h). The gray symbols represent ER proteostasis factors. The ATF6-regulated ER proteostasis genes BiP, GRP94, and SEL1L are highlighted.

FIG. 3D-F. Correlation of $\log_2$ mRNA fold change (FC) with Tg (500 nM; 6 h; relative to vehicle-treated control) versus $\log_2$ mRNA fold change with small molecule ER proteostasis regulators 132 (FIG. 3D), 263 (FIG. 3E) or 147 (FIG. 3F) in HEK293T-Rex cells (treated as indicated above). All genes displaying a significant change (BH adjusted p-value <0.1) for Tg-treatment or treatment with small molecule ER proteostasis regulators are shown. The gray symbols represent ER proteostasis factors. The gray dashed line reflects levels of gene induction observed following Tg-induced ER stress. The black dashed line reflects the induction of ER proteostasis gene induction observed following treatment with the indicated small molecule ER proteostasis regulator. Treatment with 132 (FIG. 3D) shows a clear correlation with Tg treatment indicating global UPR activation, while 263 (FIG. 3E) and 147 (FIG. 3F) do not globally increase transcription of Tg-regulated genes and show lower levels of select ER proteostasis gene induction. The ATF6-regulated ER proteostasis genes BiP, GRP94, and SEL1L are highlighted.

FIG. 5—Small molecule ER proteostasis regulators reduce secretion of destabilized amyloidogenic TTR$^{A25T}$ from HepG2 cells FIG. 5A. Representative autoradiogram of [$^{35}$S]-labeled $^{FT}$TTR$^{A25T}$ in the lysate (Lys) and media (Med) secreted from HepG2$^{ATF6}$ cells pretreated for 15 h with 10 µM small molecule 132, 147 or 263, or 1 µM Tg. The experimental paradigm is shown above.

FIG. 5B. Quantification of the fraction $^{FT}$TTR$^{WT}$ or $^{FT}$TTR$^{A25T}$ secreted following a 4 h chase in HepG2$^{ATF6}$ cells pretreated for 15 h with Tg (1 µM) or 10 µM small molecule 132, 147 or 263. A representative autoradiogram for this experiment is shown in FIG. 5A. Fraction secreted was calculated as described in Online Methods. Error bars show standard error for n=4 replicates.

FIG. 5C. Quantification of the normalized fraction $^{FT}$TR$^{WT}$ or $^{FT}$TTR$^{A25T}$ secreted following a 4 h chase in HepG2$^{ATF6}$ cells pretreated for 15 h with Tg (1 µM) or 10 µM small molecule 132, 147 or 263. Normalized fraction secreted was calculated relative to the vehicle-treated control using the values shown in FIG. 5B. Error bars show standard error for n=4 replicates; *p<0.05, **p<0.001.

FIG. 5D. Quantification of the normalized fraction $^{FT}$TR$^{WT}$ or $^{FT}$TTR$^{A25T}$ remaining (lysate+media) following a 4 h chase in HepG2$^{ATF6}$ cells pretreated for 15 h with Tg (1 µM) or 10 µM small molecule 132, 147 or 263. Normalized fraction remaining was calculated relative to the vehicle-treated control as described in the Online Methods. Error bars show standard error for n=4 replicates; *p<0.05, *p<0.01, **p<0.001.

FIG. 5E-F. Representative autoradiogram (FIG. 5E) and quantification (FIG. 5F) for total [$^{35}$S]-labeled protein secreted from HepG2$^{ATF6}$ cells following 15 h pretreatment with 1 µM Tg, TMP (10 µM)-dependent DHFR-ATF6 activation, or 10 µM small molecule ER proteostasis regulators 132, 147 or 263. Following pretreatment, cells were labeled with [$^{35}$S] for 30 min. After washing, the cells were incubated for 4 h in non-radioactive media prior to collecting conditioned media and analyzed by SDS-PAGE/autoradiography. Bar graph (FIG. 5F) shows total [$^{35}$S]-labeled protein in media normalized to the vehicle-treated control. Error bars show standard error for n=4 replicates. **indicates p<0.001.

FIG. 6—Small molecule ER proteostasis regulators reduce secretion of destabilized, amyloidogenic immunoglobulin light chains from AL patient-derived plasma cells.

FIG. 6A. qPCR analysis of BiP expression in ALMC-2 cells treated for 6 h with 10 µM of the indicated small molecule ER proteostasis regulators. Error bars show standard error for n=3 replicates. *p<0.05, **p<0.01.

FIG. 6B. Graph showing relative media levels of ALLC measured by ELISA and cellular viability of ALMC-2 cells pretreated with 10 µM of the indicated small molecule ER proteostasis regulators. Cells treated with 500 nM Tg are shown as a control. Error bars show standard error for n>6 replicates. *p<0.05, p<0.01, p<0.001.

FIG. 6C. Quantification of ALLC immunopurifications from ALMC-2 cells after treatment with the indicated ER proteostasis regulator (10 µM; 16 h) and in situ cross-linking. The relative recovery of GRP94 and BiP in each sample normalized to the recovered ALLC is shown. Error bars show standard error for n=4 replicates. *p<0.05; **p<0.01.

FIG. 6D. Graph showing relative media levels of IgG measured by ELISA and cellular viability of KAS-6/1 cells treated with 10 µM of the indicated small molecule ER proteostasis regulators. Cells treated with 500 nM Tg are shown as a control. Error bars show standard error for n=3 replicates. *p<0.05, p<0.01, p<0.001.

FIG. 6E. Blue Native-PAGE/Immunoblot of conditioned media prepared on ALMC-2 cells pretreated with the indicated ER proteostasis regulator (10 µM; 16 h). After pretreatment, media were exchanged and the volume adjusted to account for decreases in cell viability with several compounds. After conditioning for 8 h, the media were collected and then heated to 55° C. for 8 h to induce ALLC aggregation. An SDS-PAGE/immunoblot of the same samples is shown as a control.

FIG. 6F. Quantification of the total and aggregate ALLC amounts in the immunoblots as shown in FIG. 6E. Error bars show standard error for n>3 replicates. *p<0.05, p<0.01, *p<0.001.

FIG. 7—Synthesis and structure-activity relationships (SAR) of 147 and derivatives.

FIG. 7A. Synthetic scheme to access compound 147 and structural analogs.

FIG. 7B and FIG. 7D. Structures of synthesized 147 analogs.

FIG. 7C and FIG. 7E. Plots showing ERSE-FLuc activation in HEK293T-Rex cells stably expressing ERSE-FLuc treated with vehicle, Tg (1 µM), 147, resynthesized 147*, or synthesized analogs of 147 (147a-m, all 10 µM). Luminescence is shown as fold-increase relative to vehicle. Error bars show standard deviation from n=3 replicates.

FIG. 8—Synthesis and structure-activity relationships (SAR) of 147 and 263 derivatives.

DETAILED DESCRIPTION

Cell-Based High-Throughput Screen to Identify Small Molecule ER Proteostasis Regulators We employed a transcriptional reporter that quantifies activation of the ATF6 arm of the UPR in HEK293T-Rex cells. This reporter contains a fragment of the UPR-inducible BiP promoter, including three ER stress-responsive elements (ERSEs), driving expression of firefly luciferase (ERSE-FLuc; FIG. 1a)[34]. We previously employed this reporter for a small-scale screen using the 1280 member compound Library of Pharmacologic Active Compounds (LoPAC) to find small molecules that activate the UPR[8]. After stable transfection of the reporter into HEK293T-Rex cells, we isolated a single clone exhibiting dose-dependent activation of the ERSE-FLuc reporter upon treatment with the ER stressors Tg or Tm (FIG. 1b,c). Optimization and miniaturization of this assay to 1536-well format was performed at the Scripps Research Institute Molecule Screening Center (SRIMSC). The Z' for the miniaturized assay was 0.65 using Tg as the positive control, demonstrating that this assay is sufficiently robust to identify novel small molecule activators of the UPR in large compound libraries. A 17,000 compound pilot screen using the Scripps Drug Discovery Library (SDDL) identified 239 small molecules that activated the ERSE-FLuc reporter >18% of the Tg control, revealing a hit rate of 1.36%.

We next performed a HTS utilizing the complete 644, 951-molecule SDDL at SRIMSC. The performance of this assay was consistent across all experimental plates (Z'=0.58±0.05) and exhibited a robust signal to noise ratio (signal/background=6.21±0.73). Small molecule activation of ERSE-FLuc was normalized to Tg (assigned to be 100% activation), allowing comparisons between screening plates. This screen identified 13,799 molecules that activated the ERSE-FLuc reporter >25.1%. These hits were then compared to results from a previous screen of the SDDL that identified small molecules that activate the heat shock response[35]. Since we were focused on identifying molecules that selectively activate UPR signaling pathways, molecules that activated both the ERSE-FLuc reporter and the heat shock response reporter were no longer considered.

Figure 1E:
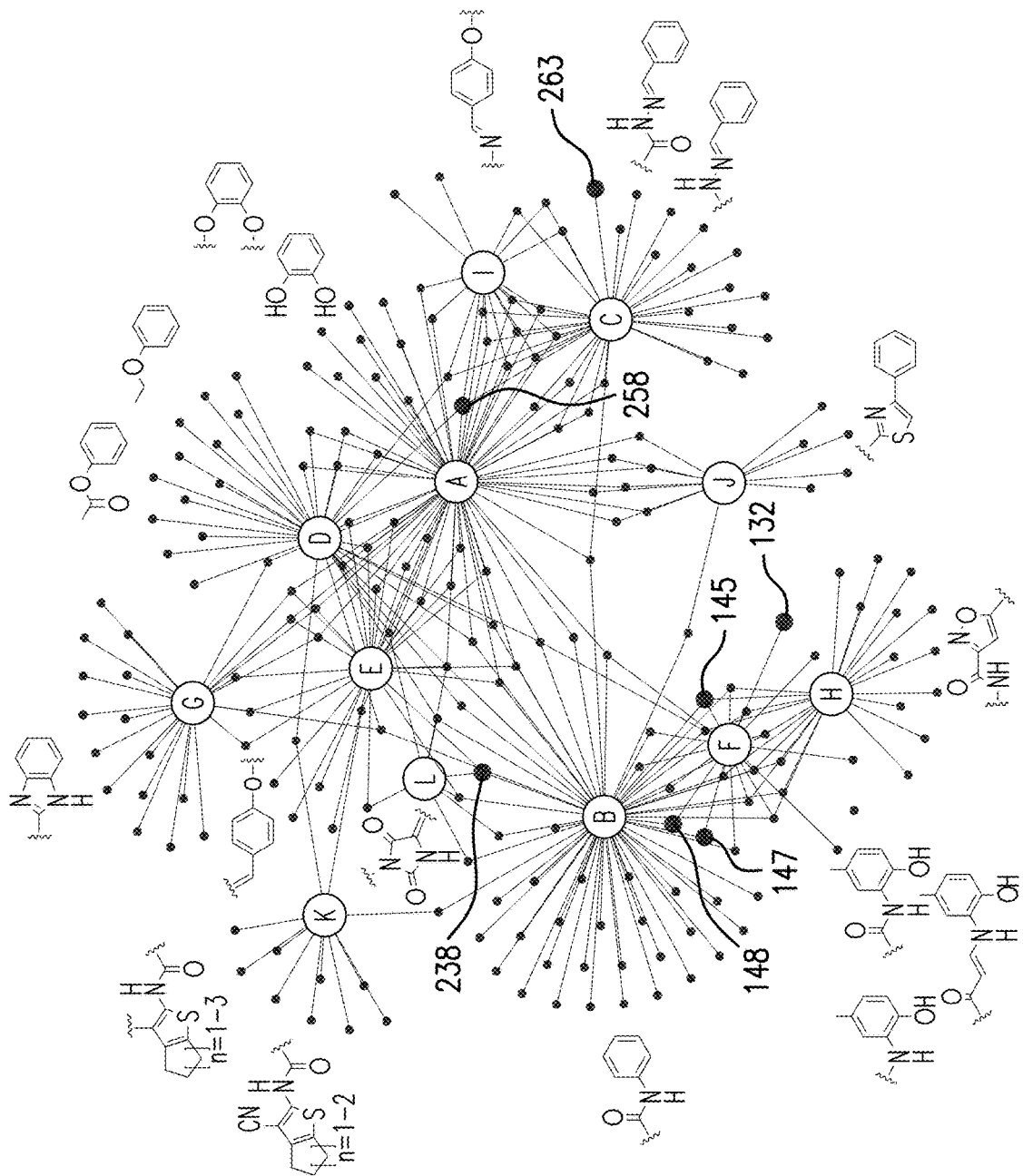
FIG. 1E. Network plot depicting the 12 overrepresented structural moieties (A-K) identified by performing a hierarchical maximum common substructure search of the top 281 small molecule ER proteostasis regulators. The 8 prioritized small molecule ER proteostasis regulators are shown.

Confirmation screening of the remaining 13,750 compounds identified 12,376 molecules that activated the ERSE-FLuc reporter 3 standard deviations above the DMSO control (hit cutoff 5.7% activation)—a 90% hit confirmation (FIG. 1d). To decrease the number of compounds for follow-up, we increased the cutoff stringency to that used in the primary screen (25.1% activation), which narrowed the list of ERSE-FLuc activators to 281 compounds (FIG. 1d). This list includes the ER stressors Tg and Tm, which were present in the SDDL. All 281 confirmed hits were subjected to quality control at SRIMSC to confirm identity and purity using liquid chromatography/mass spectrometry. A maximum common substructure search identified 12 chemical substructures that were highly represented in these 281 ERSE-FLuc activators (FIG. 1e). These include catechols (64/281), anilides (61/281) and benzylidine hydrazines (33/281).

ER Proteostasis Regulators Activate the ATF6 Arm of the UPR

Figure 2A:
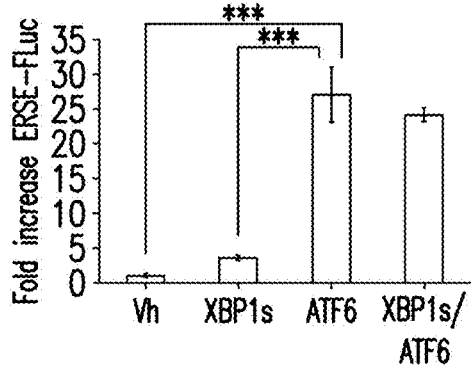
FIG. 2—Small molecule ER proteostasis regulators activate the ATF6 arm of the UPR FIG. 2A. Activation of ERSE-FLuc in HEK293$^{DAX}$ cells stably expressing trimethoprim (TMP)-regulated DHFR-ATF6 and doxycycline (dox) inducible XBP1s. Dox (1 µM; 12 h) was added to selectively activate XBP1s and TMP (10 µM; 12 h) was added to activate DHFR-ATF6. Co-addition of dox (1 µM) and TMP (10 µM) for 12 h was added to activate both XBP1s and ATF6. Error bars show standard error for n=3. **$p<0.001$.
FIG. 2B. Schematic of the XBP1-RLuc splicing reporter used to monitor activation of the IRE1/XBP1s arm of the UPR in HEK293T-Rex cells treated with small molecule ER proteostasis regulators.
FIG. 2C. Scatter plot of ERSE-FLuc activation and XBP1-RLuc activation for our top 281 small molecule ER proteostasis regulators (6.8 µM; 18 h) in HEK293T-Rex cells stably expressing ERSE-FLuc or XBP1-RLuc. Activation for each axis is shown as the percent signal relative to Tg treatment (500 nM; 18 h). Prioritized ER proteostasis regulators described in Table 1 are shown in gray. Error bars show standard deviation for n=3.
FIG. 2D. BIP mRNA measured by qPCR in ATF6$^{+/+}$ and ATF6$^{-/-}$ MEFs treated with the indicated small molecule ER proteostasis regulators (10 µM; 6 h). Error bars show standard error for n>3. *$p<0.05$; $p<0.01$; $p<0.001$.
FIG. 2E. Activation of ATF6 as measured by nuclear localization of GFP-ATF6. U2OS-GFP-ATF6 cells were treated with the top 8 small molecule ER proteostasis regulators (10 µM; 5 h) or Tg (100 nM; 5 h) and subcellular localization of GFP was assessed by confocal microscopy. The nuclear:ER ratio of GFP signal corresponding to activation of GFP-ATF6 was calculated by comparing vehicle to Tg treatment. Error bars show standard error for n=3 replicates. Dotted line shows mean plus three standard deviations from vehicle treated controls (28.65%). **$p<0.001$ using one way ANOVA followed by Tukey's Multiple comparison test (compared to vehicle).
FIG. 2F. Attenuation of ERSE-FLuc activation through inhibition of site-1 protease (S1P). HEK293T-Rex cells stably expressing ERSE-FLuc were treated with the top 8 small molecule ER proteostasis regulators (10 µM; 18 h). The S1P inhibitor PF-429242 (10 µM; 18 h) was co-added to the indicated cells. Cells treated with Tg (500 nM; 18 h) are shown as a control. Error bars show standard error for n=3. **$p<0.001$.

ATF6-mediated remodeling of the ER PN reduces secretion and/or aggregation of destabilized misfolding-prone proteins associated with human disease[21-26]. Thus, we were interested in identifying small molecules that activate the ATF6 arm of the UPR. The ERSE-FLuc reporter uses a promoter region from the ATF6-inducible gene BiP[21], indicating that this reporter may be preferentially sensitive to ATF6 activation versus other UPR-associated transcription factors, such as XBP1s. We tested this prediction in HEK293$^{DAX}$ cells (FIG. 2a)—a HEK293T-Rex derived cell line that expresses tet-inducible XBP1s and a trimethoprim (TMP)-regulated dihydrofolate reductase (DHFR)-ATF6 fusion[21]. In these cells, the addition of doxycycline (dox) induces XBP1s transcription while the addition of TMP stabilizes the active DHFR-ATF6 transcription factor. As predicted, the ERSE-FLuc reporter is preferentially activated by TMP-dependent DHFR-ATF6 activation (FIG. 2a). The selectivity of the ERSE-FLuc reporter for ATF6 over XBP1s suggests that the 281 ER proteostasis regulators identified through our primary screen may preferentially activate the ATF6 transcriptional program.

Figure 2B:
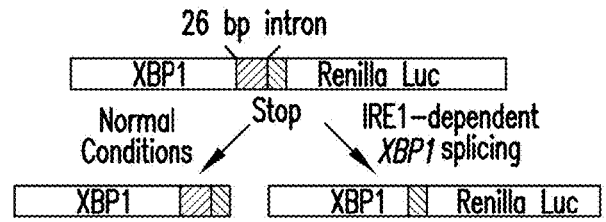

To evaluate the selectivity of our screening hits for ATF6, we employed an alternative luciferase reporter to measure activation of the IRE1/XBP1s arm of the UPR. This reporter contains Renilla luciferase (RLuc) expressed out of frame downstream of the XBP1 splice site, preventing RLuc translation in the absence of stress (FIG. 2b)[36,37]. In response to IRE1 activation, the 26-nt XBP1 intron is removed, producing a frame shift that allows for RLuc translation and activity. Robust dose-dependent activation of the XBP1-RLuc reporter upon addition of the ER stressors Tg and Tm was confirmed in HEK293T-Rex cells stably expressing the XBP1-RLuc reporter, producing a Z' score of 0.75 for Tg.

Figure 2C:
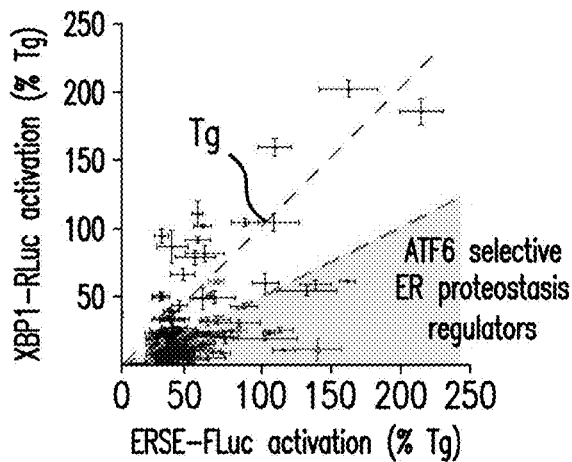

We compared the activation of the XBP1-RLuc reporter with that observed for the ERSE-FLuc reporter for the 281 confirmed screening hits. For this analysis, we normalized small molecule-dependent activation of these reporters to that observed with Tg (defined as 100% activation) to allow direct comparisons for reporter activation. Importantly, Tg, which was included in the 281 molecules hits used in this experiment, robustly activates both the ATF6-selective ERSE-Fluc reporter and the IRE1/XBP1s selective XBP1-Rluc reporter (FIG. 2c). Importantly, the majority of molecules (200/281) activate the ATF6-selective ERSE-FLuc reporter at least 2-fold better than the IRE1/XBP1s selective XBP1-RLuc reporter (FIG. 2c), suggesting that the high-throughput screen identified preferential ATF6 activators.

To further evaluate the ability of these molecules to preferentially activate ATF6, multiplex gene expression (MGE) profiling in HEK293T-Rex cells was performed to measure small molecule-dependent increases in the mRNA of target genes regulated by the ATF6, IRE1/XBP1s, and PERK UPR signaling pathways. In this effort we also monitored genes regulated by other stress-responsive signaling pathways, including the heat shock response (HSR), the oxidative stress response (Nrf2), and inflammatory signaling (NFκB). This analysis identified 18 molecules, including the ER stressors Tg and Tm, that robustly activated genes regulated downstream of ATF6, IRE1/XBP1s and PERK indicating that these molecules are global UPR activators. Seventy-nine compounds grouped into clusters exhibiting preferential activation of ATF6-regulated genes, relative to IRE1/XBP1s- and PERK-regulated genes. These molecules did not induce expression of stress-responsive genes regulated by other stress-responsive signaling pathways.

Based on the above results, we selected 8 small molecule ER proteostasis regulators for extensive characterization (Table 1). These molecules were chosen based on their ability to preferentially activate the ERSE-FLuc reporter and ATF6 regulated genes, their fold-increase in ERSE-FLuc activation, and their structural characteristics to ensure that structurally diverse compounds were represented. These 8 molecules demonstrated maximum toxicity of <10-43% that of doxorubicin in HEK293T-Rex cells, with all molecules having cytotoxic concentration 50% ($CC_{50}$) >17 µM (the highest tested concentration), indicating that these molecules were generally non-toxic. The toxicity observed in these cancer cell lines is likely higher than will be observed in human tissues.

ER Proteostasis Regulators Require ATF6 Processing for Function

Figure 2D:
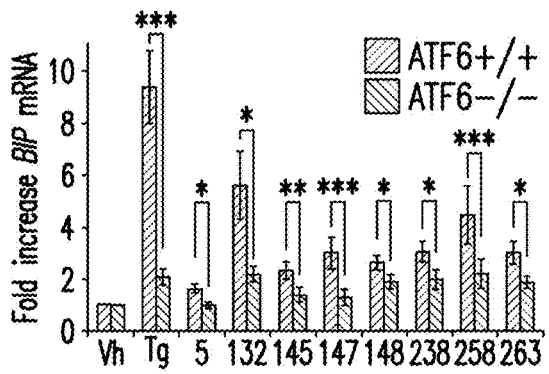

We next evaluated whether the 8 prioritized ER proteostasis regulators depended on ATF6 for function. Small-molecule dependent induction of the ATF6 target gene BiP was evaluated in ATF6$^{+/+}$ and ATF6$^{-/-}$ mouse embryonic fibroblast (MEFs)[38]. BiP was induced in ATF6$^{+/+}$ MEFs treated with the small molecule ER proteostasis regulators to varying extents (FIG. 2d). Increased BiP expression was significantly reduced in the ATF6$^{-/-}$ MEFs, indicating that these small molecules depend on ATF6 for BiP induction (FIG. 2d). Importantly, we did not observe significant levels of XBP1 splicing or eIF2α phosphorylation in cells treated with our top ER proteostasis regulators, indicating that these molecules do not significantly activate the IRE1/XBP1s or PERK arms of the UPR.

Figure 2E:
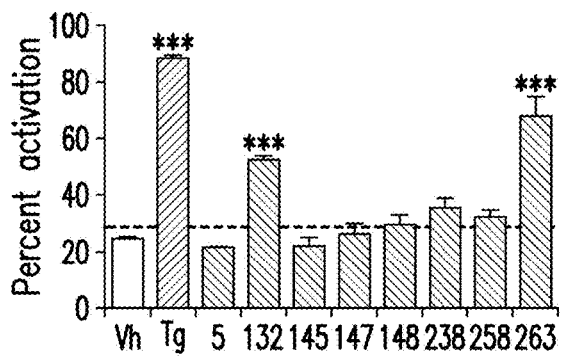

ATF6 activation involves trafficking of the full-length ATF6 protein to the Golgi. Here, ATF6 is processed by S1P and S2P to release the cytosolic bZIP active transcription factor, facilitating nuclear localization[18]. To evaluate the influence of the 8 ER proteostasis regulators on ATF6 processing, we measured ATF6 nuclear translocation using a fluorescence-based high-content imaging assay that quantifies nuclear-localized ATF6-GFP relative to ER-localized ATF6-GFP. Treatment with two small molecules, 132 and 263, significantly increased the nuclear fraction of ATF6-GFP, reflecting increased ATF6 nuclear translocation (FIG. 2e). Compounds 132 and 263 also showed increased accumulation of the 50 kDa ATF6 fragment that results from S1P/S2P proteolysis in the Golgi, as shown by immunoblotting. While other molecules did not give a significant increase in ATF6-GFP nuclear localization or accumulation of the 50 kDa ATF6 fragment, it cannot be excluded that they also induce ATF6 nuclear translocation, albeit to a lower extent that falls outside the dynamic range or sensitivity of these assays.

Figure 2F:
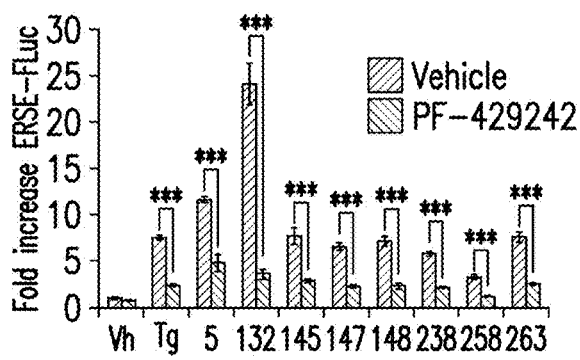

To further evaluate how ER proteostasis regulator function depends on ATF6 processing, we tested whether activation of the ERSE-FLuc reporter is sensitive to S1P inhibition. Addition of the S1P inhibitor PF-429242 impeded Tg-mediated ERSE-FLuc activation, reflecting the dependence of ATF6 activation on proteolytic processing by S1P (FIG. 2f)[39]. PF-429242 also inhibited the activation of ERSE-FLuc in cells treated with all 8 ER proteostasis regulators (FIG. 2f), demonstrating that small-molecule-dependent ERSE-FLuc activation requires S1P function. Collectively, the ATF6 knockout, nuclear localization and S1P inhibition results indicate that the ER proteostasis regulators activate endogenous ATF6.

mRNA-Seq Defines Transcriptional Remodeling of ER Proteostasis Pathways by Small Molecule Activators To define how the initially prioritized small molecules affect the ER PN and the global transcriptome, we performed mRNA-seq transcriptional profiling on HEK293T-Rex cells treated with the small molecule ER proteostasis regulators 132, 263 and 147. These compounds are structurally diverse and exhibit variable levels of activity and selectivity in our reporter assays and MGE profiling experiments (Table 1). As a control, mRNA-seq analysis was also performed on cells treated with the global ER stressor Tg and on HEK293$^{DAX}$ cells following TMP-dependent DHFR-ATF6 activation (chemical genetic activation). Select mRNA-seq data for ER and cytosolic PN genes is shown in Table 2.

Of the three compounds tested, 132 induced the most alterations in mRNA levels (FIG. 3a), including significant upregulation of ER proteostasis genes such as BiP, GRP94 and SEL1L (FIG. 3a, red). Alternatively, 263 and 147 induced more modest changes in mRNA levels (FIGS. 3b,c), consistent with their lower activation of the ERSE-FLuc reporter (Table 1, FIG. 2f) and lower induction of BiP transcripts (FIG. 2d). Despite the lower fold changes, ER proteostasis factors were enriched in genes induced by treatment with 263 and 147 (FIGS. 3b,c, red). In addition to mRNA-Seq transcriptional profiling, we evaluated the protein expression changes induced by treatment with 132, 263 and 147 in HEK293T-Rex cells using quantitative mass-spectrometry based proteomic profiling. Protein expression changes after each compound treatment correlated with transcript changes observed by mRNA-Seq, confirming the induction of ER proteostasis factors at the protein level. Furthermore, the extent of protein expression changes followed the same trend as the transcript changes: induction was highest with compound 132, and less strong with compounds 263 and 147. Lastly, we confirmed by quantitative Western blotting that the compounds induced several ATF6-regulated ER PN components (BiP, GRP94, PDIA4).

We next compared the transcriptional remodeling induced by these three small molecule ER proteostasis regulators to that induced by the global UPR activator Tg to define the selectivity of these compounds for UPR activation relative to other alterations of the transcriptome. Gene changes induced by Tg and 132 showed a linear relationship, suggesting that 132 globally activates the UPR (FIG. 3d; slope=1). In contrast, compounds 263 and 147 did not globally increase expression of Tg-regulated genes, but these molecules did induce expression of select ER proteostasis genes albeit to lower extents relative to Tg or 132 (Table 2, FIGS. 3e,f; slope <1). Three non-ER proteostasis genes—HSPA1A, HSPA1B, and HMOX1—were induced by all of the ER proteostasis regulators, but not Tg (FIGS. 3d-f). HSPA1A and HSPA1B are transcriptional targets of the heat-shock response (HSR)-associated transcription factor HSF1[40] and HMOX1 is a transcriptional target of the oxidative stress response[41]. Comparing the transcriptional profile previously observed for HSF1 activation[40] to that observed for 132, 147, and 263 showed no significant correlation, indicating that these molecules do not induce HSF1 or activate the HSR. Similarly, we did not observe increased expression of oxidative stress markers, indicating that these molecules do not globally activate the oxidative stress response. Taken together, these results show that our small molecule ER proteostasis regulators preferentially influence the expression of UPR target genes.

Figure 4A:
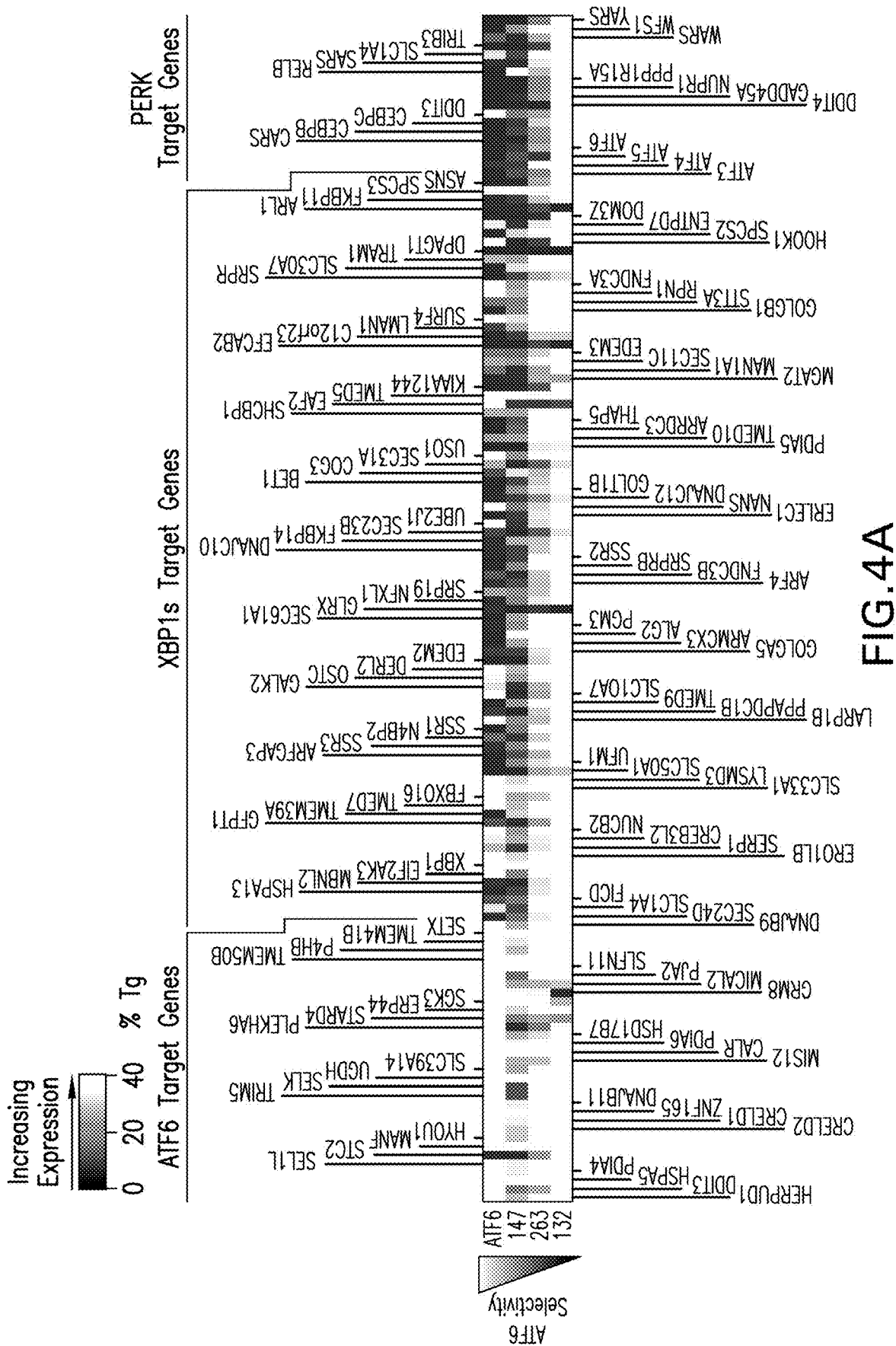
FIG. 4—Small molecule ER proteostasis regulators preferentially activate the ATF6 transcriptional program FIG. 4A. Heat map showing the upregulation of ATF6, XBP1s or PERK target genes in our mRNA-seq analysis of HEK293T-Rex cells treated with Tg (500 nM), 132 (10 µM), 147 (10 µM) or 263 (10 µM). Genes used in this analysis were selected from published reports indicating their selectivity for ATF6, XBP1s or PERK[21,42]. The induction of each gene was normalized to the respective induction observed with the global UPR activator Tg and reported as % Tg induction. The expression of these target genes in the mRNA-seq analysis of TMP-dependent DHFR-ATF6 activation in HEK293$^{DAX}$ cells is also shown.
FIG. 4B-E. Box plots showing the relative activation of ATF6, XBP1s, and PERK genesets in HEK293$^{DAX}$ cells following TMP-dependent DHFR.ATF6 activation (FIG. 4B) or HEK293T-Rex cells treated with 147 (FIG. 4C), 263 (FIG. 4D) or 132 (FIG. 4E) from the data shown in FIG. 4A. Differences in activation of the ATF6 geneset relative to the XBP1s or PERK genesets were confirmed by one-way ANOVA and the p-values of unpaired t-tests are shown.
FIG. 4F-G. Plot showing the relative activation of the ERSE-Fluc and XBP1-Rluc reporters in HEK293T-Rex cells treated with the indicated concentration of 147 (FIG. 4F) or 263 (FIG. 4G) for 15 h. Error bars represent standard error for n=3 replicates.
Figure 4B:
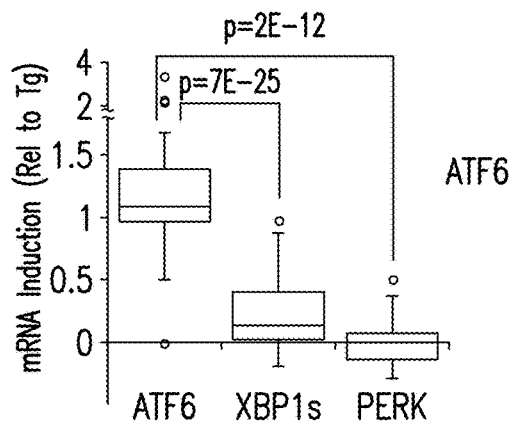
Figure 4C:
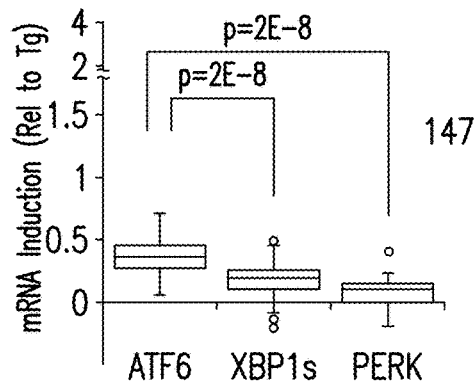
Figure 4D:
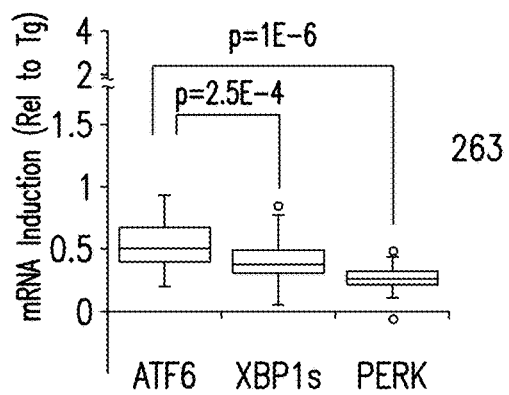

We next evaluated the selectivity of 132, 147, and 263 for inducing transcriptional programs downstream of the UPR stress sensors ATF6, IRE1 and PERK. For this analysis, we defined genesets of >15 UPR target genes that are preferentially activated downstream of each UPR signaling pathway or arm of the UPR. These genes were selected for their preferential induction by stress-independent activation of XBP1s, ATF6 or PERK in previously published transcriptional profiles[21,42]. The induction of these genes by small molecule ER proteostasis regulators was then normalized to the Tg-dependent induction, allowing for direct comparisons of the transcriptional activity across the three genesets. As expected, this approach demonstrates that stress-independent DHFR-ATF6 activation selectively induces the ATF6 transcriptional geneset relative to the IRE1/XBP1s or PERK genesets (FIGS. 4a,b).

Figure 4E:
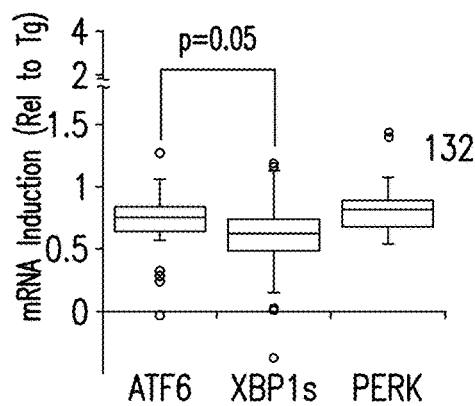

Compounds 147 and to a lesser extent also 263 preferentially activate the ATF6 geneset relative to IRE1/XBP1s or PERK (FIGS. 4a,c,d), albeit to levels lower than that observed for ER stress-induced UPR activation, showing 45% and 50% activation relative to Tg, respectively. In contrast, compound 132 shows a higher induction of the ATF6 geneset (75% relative to Tg; FIG. 4e) but it significantly induced both the IRE1/XBP1s and PERK genesets, although modest selectivity for ATF6 gene expression relative to XBP1s can be observed (FIGS. 4a,e). An analogous geneset analysis of the proteomics data similarly displayed preferential activation of ATF6 targets at the protein level by 147, whose selectivity is greater than that of 263, and both exceeding that of 132. These results show that small molecule ER proteostasis regulators 147 and to a lesser extent 263 preferentially activate the ATF6 transcriptional arm of the UPR, while compound 132 is a global activator of all three arms of the UPR, but not other stress-responsive signaling pathways.

Figure 4F:
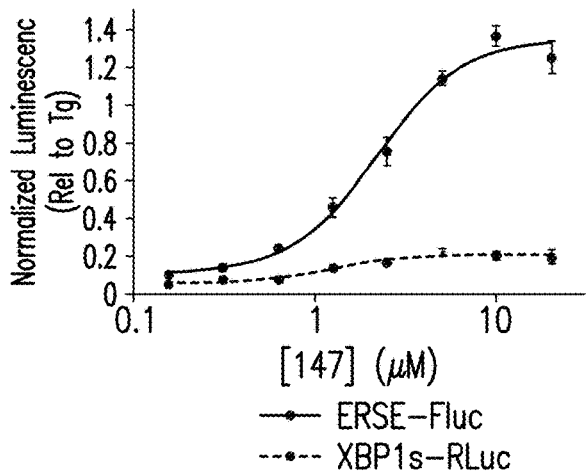
Figure 4G:
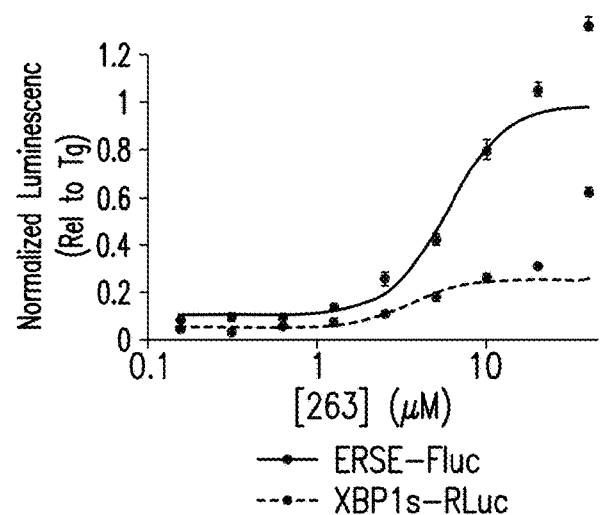

Preferential activation of ATF6 target genes by 147 and 263 could result from a mild level of ER stress that could be increased through addition of higher ER proteostasis regulator concentrations or longer duration of the treatment. We therefore monitored the activation of the ATF6-selective ERSE-Fluc reporter in HEK293 cells treated with increasing concentrations of 147, 263 and 132 (FIGS. 4f,g). No compound showed significant increases in ERSE-Fluc reporter activation at concentrations >10 µM—the concentration used for mRNA-seq. Similarly, increasing the concentration of these molecules did not significantly increase activation of the IRE1/XBP1s-selective XBP1-RLuc reporter (FIGS. 4f,g). Similar results were observed by qPCR. Furthermore, we observe a maximal BiP induction at 6 h in cells treated with 132, 147 or 263 over a 24 h timecourse and no time-dependent increases in expression of the XBP1s target Sec24D. These results indicate that increasing the concentration or duration of treatment with small molecule ER proteostasis regulators does not alter the preferential activation of the ATF6 transcriptional program.

Collectively, our results show that small molecule ER proteostasis regulators such as 147 and 263 selectively activate an ATF6-selective reporter (relative to an IRE1/XBP1s reporter, FIG. 2c), require endogenous ATF6 for increased BiP expression (FIG. 2d), are sensitive to S1P inhibition (FIG. 2f), and preferentially induce ATF6-dependent remodeling of the ER PN (FIG. 4a-e). These results demonstrate that these top molecules preferentially activate the ATF6 arm of the UPR relative to the IRE1/XBP1 and PERK arms of the UPR.

ER Proteostasis Regulators Reduce Secretion of Amyloidogenic TTR42$^{5T}$ from Liver-Derived HepG2 Cells TMP-mediated DHFR-ATF6 activation (chemical genetic activation) preferentially reduces secretion of destabilized, amyloidogenic TTR variants from liver-derived HepG2 cells[21,25]. Therefore, we examined whether small-molecule ER proteostasis regulators similarly reduced secretion of the destabilized, amyloidogenic A25T TTR variant (TTR$^{A25T}$) from HepG2 cells. For these experiments, we initially confirmed that compounds 132, 147, and 263 induced expression of the ATF6-target gene BiP in HepG2 cells using qPCR. We also showed that these molecules do not significantly influence HepG2 viability when added at 10 µM, although higher concentrations (100 µM) do reduce HepG2 viability.

We then measured secretion of flag-tagged TTR$^{A25T}$ ($^{FT}$TTR$^{A25T}$) and flag-tagged TTR$^{WT}$ ($^{FT}$TTR$^{WT}$) from HepG2 cells stably expressing TMP-regulated DHFR-ATF6 (HepG2$^{ATF6}$)[25] following pretreatment with the global ER stressor Tg or our small molecule ER proteostasis regulators. $^{FT}$TTR$^{A25T}$ and $^{FT}$TTR$^{WT}$ secretion was monitored by [$^{35}$S] metabolic labeling (FIG. 5a). As reported previously[21,25], the fraction of $^{FT}$TTR$^{A25T}$ secreted from vehicle-treated cells was less than that observed for $^{FT}$TTR$^{WT}$, reflecting the destabilization of this TTR variant (FIG. 5b). Pretreatment with Tg reduced secretion of both $^{FT}$TTR$^{A25T}$ and $^{FT}$TTR$^{WT}$, indicating that Tg-induced ER stress impairs TTR secretion from these cells (FIG. 5b,c). Alternatively, pretreatment with the two compounds that preferentially activate the ATF6 arm of the UPR, 147 and 263, reduced $^{FT}$TTR$^{A25T}$ secretion by 45%, but did not significantly influence secretion of $^{FT}$TTR$^{WT}$ (FIG. 5b,c). The reduction in $^{FT}$TTR$^{A25T}$ secretion induced by these molecules corresponds with increased degradation of $^{FT}$TTR$^{A25T}$ (FIG. 5d). Notably, this preferential reduction in secretion and increased degradation for $^{FT}$TTR$^{A25T}$ induced by small molecule ER proteostasis regulators 147 and 263 is analogous to that observed for TMP-dependent DHFR-ATF6 activation (chemical genetic activation) in these cells[25]. Alternatively, the small molecule ER proteostasis regulator 132, which globally activates UPR signaling pathways, did not significantly influence secretion or degradation for $^{FT}$TTR$^{A25T}$ or $^{FT}$TTR$^{WT}$ in these HepG2$^{ATF6}$ cells (FIG. 5b,c).

We next sought to establish that the small molecule ER proteostasis-regulator dependent reductions in $^{FT}$TTR$^{A25T}$ secretion were dependent on ATF6. We shRNA-depleted ATF6 from HEK293 cells and measured $^{FT}$TTR$^{A25T}$ secretion using the same [$^{35}$S] metabolic labeling experiments described above. We confirmed ATF6 knockdown by qPCR. Unfortunately, depletion of ATF6 in these cells reduced $^{FT}$TTR$^{A25T}$ secretion by >40% in the absence of small molecule ER proteostasis regulators. Similarly, overexpression of dominant negative ATF6 lacking the transactivation domain (ATF6$^{DN}$)[43] reduced $^{FT}$TTR$^{A25T}$ secretion from HepG2 cells by >20% in the absence of small molecule treatment. The reduced secretion of $^{FT}$TTR$^{A25T}$ observed in these experiments demonstrates that the loss of basal ATF6 activity disrupts ER proteostasis and function, precluding us from using these approaches to explicitly define the contributions of ATF6 activation on the small molecule ER proteostasis regulator-dependent reductions in $^{FT}$TTR$^{A25T}$ secretion. Importantly, our results do show that small molecule ER proteostasis regulators phenocopy stress-independent ATF6 activation in their ability to preferentially reduce secretion and increase degradation of $^{FT}$TTR$^{A25T}$ in liver-derived HepG2$^{ATF6}$ cells[21,25].

We next monitored the secretion of the endogenous secretory proteome from HepG2$^{ATF6}$ cells using metabolic labeling. Cells were pretreated for 15 h with Tg, TMP (to activate DHFR-ATF6) or ER proteostasis regulators before being labeled with [$^{35}$S] for 30 min. Secretion of [$^{35}$S]-labeled protein into the media was then measured following a 4 h chase (FIG. 5e). As expected, Tg treatment significantly impaired the recovery of [$^{35}$S]-labeled proteins in conditioned media, consistent with this ER stressor attenuating protein translation and globally disrupting protein secretion. Alternatively, pretreating cells with TMP-dependent DHFR-ATF6 activation or compounds 132, 147 or 263 did not influence the accumulation of [$^{35}$S]-labeled protein in media. Although alterations in the secretion of low abundance individual proteins cannot be conclusively ruled out, these results indicate that the ER proteostasis regulators do not globally disrupt secretion of the endogenous proteome.

ER Proteostasis Regulators Decrease Secretion and Extracellular Aggregation of Amyloidogenic Light Chains Lastly, we tested whether the ER proteostasis regulators reduce the secretion of destabilized, amyloidogenic immunoglobulin LCs that undergo proteotoxic extracellular aggregation in association with AL. Stress-independent TMP-mediated DHFR-ATF6 activation (chemical genetic activation) reduces secretion and extracellular aggregation of a destabilized, amyloidogenic LC (ALLC) without affecting secretion of a stable, non-amyloidogenic LC[26]. We evaluated whether the ER proteostasis regulators similarly reduce secretion of the same ALLC protein from an AL patient-derived plasma cell line (ALMC-2)[44].

We confirmed that 4 of the 8 prioritized ER proteostasis regulators (132, 145, 147 and 148) induced expression of the ATF6 target gene BiP in ALMC-2 cells (FIG. 6a). We then quantified secretion of ALLC from ALMC-2 plasma cells after pretreatment with these ER proteostasis regulators. The same 4 ER proteostasis regulators that induced BiP reduced ALLC secretion by >50% (FIG. 6b). We then evaluated the dose dependent reduction in ALLC secretion for 132 and our most selective ATF6 activator 147, demonstrating EC$_{50}$ values of ~1 µM. Comparison of the reduction in ALLC secretion versus BiP induction shows a striking correlation, suggesting that the reduction in ALLC secretion is dependent on the small molecule induced transcriptional ER PN remodeling. Compound 132—the global UPR activator—showed a 45% reduction in cell viability indicating that the reduced ALLC secretion is at least partially a result of cell death (FIG. 6b). Alternatively, preferential ATF6 activators, such as 147, do not significantly affect cell viability, but still reduce ALLC secretion by 60%.

We next monitored ALLC secretion from ALMC-2 cells after cycloheximide administration to determine partitioning between secretion and degradation in the absence of new protein synthesis. Treatment with 147 caused a ~30% reduction in ALLC secretion while not leading to increased protein degradation, instead resulting in intracellular accumulation. These results mirror our previous observations on the effect of stress-independent ATF6 activation on reducing ALLC secretion and increasing intracellular retention[26]. To exclude the possibility that the reduced ALLC secretion is the result of impaired protein synthesis, we confirmed by ELISA that ALLC intracellular protein levels were unchanged after treatment with 147.

To evaluate whether the reduced ALLC secretion was mediated by ATF6-dependent ER PN remodeling, we used the [$^{35}$S] metabolic labeling approach to monitor $^{FT}$ALLC secretion in HEK293T cells after genetically disrupting ATF6. Both shRNA depletion of ATF6 and overexpression of the dominant-negative ATF6$^{DN}$ (described above) led to a reduction in ALLC secretion >40% in the absence of small-molecule treatment, similarly to what was observed for $^{FT}$TTR$^{A25T}$. This indicates that any disruption in basal ATF6 levels reduces ALLC secretion, precluding us from further defining the contribution of ATF6 activation from ER proteostasis regulator treatment on the reduced secretion of ALLC.

Instead, to demonstrate that preferential ATF6-mediated PN remodeling is likely responsible for the reduced ALLC secretion from plasma cells, we used cross-linking in living cells and a co-immunopurification protocol to define alterations in the interaction between ALLC and ATF6-regulated chaperones such as BiP and GRP94 after small molecule ER proteostasis regulator treatment. Previous results showed that chemical genetic ATF6 activation led to ALLC ER retention through increased interactions with these ATF6-regulated chaperones[26]. Pretreatment with 132 and 147, which both induce BiP expression (FIG. 6a) and reduce ALLC secretion (FIG. 6b) in ALMC-2 cells, increased the ALLC interaction with BiP and GRP94 (FIG. 6c). In contrast, these associations remained unchanged after pretreatment with 263 (FIG. 6c)—a molecule that does not significantly induce BiP (FIG. 6a) and only minimally affects ALLC secretion (FIG. 6b). These results suggest that small molecule-dependent reductions in ALLC secretion result from a mechanism involving altered interactions between ALLC and ATF6-regulated ER PN components.

To demonstrate that the ER proteostasis regulators do not generally compromise immunoglobulin secretion from plasma cells, we measured the secretion of fully-assembled IgGs from the control KAS-6/1 plasma cell line, which was isolated from a multiple myeloma patient that did not present with AL[45]. In contrast to Tg treatment, none of the ER proteostasis regulators were cytotoxic or dramatically affected IgG secretion (FIG. 6d), indicating that these molecules preferentially reduce secretion of ALLC relative to IgGs and do not induce general plasma cell toxicity.

Finally, we evaluated whether small molecule-dependent reductions in ALLC secretion attenuate the formation of extracellular soluble aggregates. We measured soluble ALLC aggregates in conditioned media prepared on ALMC-2 cells after heating to 55° C. for 8 h using Blue-Native PAGE and immunoblotting, as previously described[26]. Total ALLC protein levels were also determined by SDS-PAGE and immunoblotting. Five out of the 8 ER proteostasis regulators, including all 4 compounds that induce BiP expression in ALMC-2 cells, decreased extracellular ALLC aggregate concentrations >50% (FIG. 6e-f). This indicates that the reduction in ALLC secretion mediated by ER proteostasis regulators leads to an attenuation of extracellular LC aggregation.

Adapting subcellular proteostasis through modulation of stress-responsive signaling pathways is a promising strategy to restore mutant protein folding or enhance mutant protein degradation[12,14,15,46,47]. Here, we identify first-in-class small molecule ER proteostasis regulators that preferentially activate the ATF6 arm of the UPR. These small molecules provide a new experimental approach for probing the involvement of ATF6 in regulating ER function. Moreover, the availability of these compounds allows assessment of their therapeutic potential to correct pathologic imbalances in ER proteostasis associated with protein misfolding diseases in cell and animal models.

ATF6 is activated through a mechanism distinct to that utilized by the two other arms of the UPR. In response to ER stress, ATF6 traffics to the Golgi where it is proteolytically processed by S1P and S2P[18], releasing the active ATF6 bZIP transcription factor into the cytosol and facilitating its translocation to the nucleus where it can induce the ATF6 transcriptional program. The molecular mechanism(s) responsible for initiating ATF6 trafficking to the Golgi is poorly understood. Dissociation of the ER HSP70 chaperone BiP from the ATF6 luminal domain has been proposed to promote ATF6 trafficking[48]. Alternatively, reduction of ATF6 luminal domain disulfides has been suggested to induce monomerization of ATF6 oligomers resulting in a conformation competent for Golgi trafficking[49].

Small molecules identified in our screen, such as 147 and 263, appear to exploit the distinct mechanism(s) of ATF6 activation to enable preferential activation of the ATF6 arm of the UPR. It seems unlikely that these small molecule ER proteostasis regulators induce a mild ER stress that is sufficient for activating ATF6, but not IRE1/XBP1s or PERK arms of the UPR, based on our results showing that increasing the doses or duration of 147 or 263 treatment does not induce global UPR activation. ATF6 is not known to contain any allosteric small molecule binding sites, such as that previously identified on IRE1[50]. Thus, it is likely that our small molecule ER proteostasis regulators induce ATF6 activity through the binding of proteins that regulate ATF6 activation, such as BiP or PDIs[48,49]. Interestingly, our top ER proteostasis regulators (e.g., 147 and 263) appear to preferentially induce ATF6 activation through distinct mechanisms, based on varying levels of BiP induction observed in different cell types (e.g., 263 induces BiP in HepG2 cells, but not in ALMC-2 cells). This capacity to activate ATF6 in a cell type specific fashion could potentially be harnessed to develop compounds that induce tissue selective ER proteostasis remodeling. Thus, as we continue to optimize the potency of these small molecule ER proteostasis regulators to explore potential mechanisms of stress-independent ATF6 activation, new insights into the molecular pathways that regulate ATF6 activity will likely emerge.

One mechanism by which the ATF6 transcriptional program influences ER function is through increasing the stringency of ER protein quality control[14]. Stress-independent ATF6 activation preferentially attenuates the secretion and subsequent proteotoxic aggregation of destabilized, disease-associated proteins through enhanced degradation and/or ER retention without effecting the secretion of the endogenous proteome[21-26]. Our ATF6 selective small molecule activators strictly phenocopy the ability of stress-independent, chemical genetic ATF6 activation to preferentially reduce secretion of destabilized, disease-associated variants of amyloidogenic proteins such as TTR and immunoglobulin LC[21,25,26]. Our ability to preferentially activate ATF6 using small molecule ER proteostasis regulators such as 147 suggests that these molecules could similarly phenocopy the ATF6-dependent reductions in the trafficking and intracellular aggregation of destabilized, aggregation-prone proteins associated with other gain-of-toxicity protein misfolding diseases (e.g., A1AT-Z aggregation in liver disease and rhodopsin aggregation in retinal degeneration[22-24]) discussed in more detail below. Unfortunately, ATF6 depletion or inactivation decreases secretion of destabilized, amyloidogenic TTR and LC variants, precluding us from explicitly defining the contributions of ATF6 activation in reducing destabilized protein secretion. As we continue to define the mechanism(s) by which our small molecules preferentially activate ATF6, we will identify alternative strategies to disrupt small molecule-dependent ATF6 activation, revealing new opportunities to demonstrate the importance of ATF6-dependent ER proteostasis remodeling in the small molecule-dependent, preferential reduction in destabilized protein secretion.

The potential toxic consequences of long-term UPR activation are a possible limitation of adapting ER proteostasis to ameliorate secretory protein misfolding and/or aggregation. While some small molecule ER proteostasis regulators identified in our HTS show mild toxicity in HEK293T-Rex, HepG2, and ALMC-2 cells, a subset of compounds, especially compounds with highly preferential ATF6 activation (e.g., 147), show no significant toxicity across multiple cell models. This lack of toxicity likely reflects the capacity for these molecules to preferentially activate the ATF6 arm of the UPR, limiting apoptotic signaling downstream of IRE1 and PERK[28,29]. The moderate levels of ATF6 activation obtained using our small molecule ER proteostasis regulators are also likely lower than the threshold required to induce pathologic imbalances in ER function. For example, high levels of ATF6 activation induce hepatic steatosis in zebrafish, but lower levels do not[51]. Finally, the structural simplicity of the small molecules identified in our screen (e.g., 147) provides a significant amount of chemical space that can be explored through structure-activity relationships to optimize dosing regimens using in vivo models and limit any potential mechanism based toxicity associated with small molecule ER proteostasis regulation.

ATF6 was believed to be an undruggable arm of the UPR due to the lack of known ATF6 small molecule binding sites and our poor understanding of the mechanism of ATF6 activation. Here, we show that the ATF6 transcriptional program can be preferentially activated over the other two arms of the UPR and over other stress responsive signaling pathways using small molecules. The establishment of ER proteostasis regulators such as 147 provides a unique opportunity to define the underlying molecular mechanism(s) of ATF6 activation. These molecules also afford a valuable resource to define their therapeutic potential to correct pathologic imbalances in ER proteostasis in cellular and animal models of protein misfolding diseases. As we continue to develop our top small molecule ER proteostasis regulators through medicinal chemistry, we will establish second generation molecules with improved activity and toxicity profiles that hopefully can be translated to correct pathologic imbalances in ER proteostasis associated with human diseases such as the systemic amyloidoses.

The references for the following section of text are to be found in the Disclosure, below, entitled "Therapeutic Potential for ATF6 Activation".

Therapeutic Potential of ATF6 Activation Afforded by Our Small Molecule ER Proteostasis Regulators Imbalances in ER proteostasis are implicated in the onset and pathology of etiologically diverse human diseases including gain-of-proteotoxicity diseases linked to misfolding and/or aggregation, and loss-of-function protein misfolding diseases wherein excessive degradation occurs instead of folding and trafficking. These diseases involve nearly all organ systems, and include cardiovascular diseases, cancer, metabolic disorders, neurodegenerative maladies, hematologic disorders, and eye diseases. Interestingly, recent evidence has made it clear that adapting ER proteostasis through arm selective activation of UPR signaling pathways, such as ATF6, is a therapeutic strategy that could be broadly-applied to correct pathologic imbalances in ER function associated with these different diseases[1]. Thus, the small molecule ER proteostasis regulators that preferentially activate the ATF6 arm of the UPR identified in this patent application have substantial therapeutic potential to intervene in multiple categories of human disease. Below, we describe the evidence showing that arm selective UPR activation and more specifically ATF6 activation can be therapeutically useful for ameliorating human diseases, justifying our claims that our top small molecule ER proteostasis regulators can be applied to ameliorate pathologic imbalances in ER proteostasis and function associated with these disorders.

Gain-of-Proteotoxicity Protein Misfolding Diseases

Amyloid diseases are a class of >30 gain-of-proteotoxicity disorders causatively associated with the aberrant secretion, misfolding and/or subsequent misassembly (aggregation) of proteins in extracellular environments[2]. These diseases include Alzheimer's disease, Creutzfeldt-Jakob disease and related prion diseases, Light Chain Amyloidosis, and the TTR-related amyloidoses. It is clear that the aberrant secretion of amyloidogenic proteins in a subset of these maladies results from these misfolding-prone protein's ability to escape ER quality control[3,4]. This has led to the idea that increasing ER quality control stringency (i.e., the capacity for cells to identify misfolded, aggregation prone proteins and target them for degradation) offers a potentially broadly-applicable therapeutic strategy to reduce secretion of destabilized, misfolding-prone amyloidogenic proteins and prevent proteotoxic aggregation in extracellular environments or intracellular environments by reuptake[3,4].

One mechanism to increase ER quality control is through activation of UPR signaling arms such as the arm regulated by ATF6. Stress-independent ATF6 activation has been shown to attenuate the secretion and subsequent extracellular aggregation of destabilized, amyloidogenic proteins including transthyretin (TTR) variants and immunoglobulin light chains involved in the TTR amyloid diseases and Light Chain Amyloidosis, respectively[5-7]. Importantly, stress-independent ATF6 activation does not influence secretion of stable, wild-type TTR, fully assembled IgGs, stable, non-amyloidogenic LCs or the endogenous secretory proteome, indicating that ATF6 activation selectively reduces secretion of destabilized, amyloidogenic proteins[5-7]. Interestingly, the reduced secretion of amyloidogenic proteins corresponds with their increased interactions with ATF6-regulated ER proteostasis factors (e.g., chaperones, co-chaperones, degradation factors, etc.), demonstrating increased scrutiny of these proteins by ER quality control pathways[5-7]. These results clearly demonstrate that ATF6 activation increases ER quality control stringency for destabilized, amyloidogenic proteins, indicating that this approach could be broadly applied to ameliorate proteotoxic aggregation of amyloidogenic proteins involved in other diverse human diseases including Alzheimer's disease and human prion diseases.

Apart from increasing ER quality control stringency, ATF6 activation has also been shown to directly increase secretion of the UPR-regulated secreted chaperone ERdj3 to extracellular environments[8]. Secreted ERdj3 functions to attenuate aggregation of amyloidogenic proteins such as Aβ—a predominant peptide that aggregates in association with Alzheimer's disease. Furthermore, secreted ERdj3 has been shown to attenuate proteotoxicity induced by misfolded conformations of prion protein involved in Creutzfeldt-Jakob disease and related prion diseases[8]. These results show that ATF6 activation can directly influence extracellular proteotoxic aggregation of amyloidogenic proteins by increasing extracellular proteostasis capacity[8]—a mechanism distinct from increasing ER quality control stringency.

The above results show that ATF6 activation offers a unique opportunity to attenuate proteotoxic extracellular aggregation of amyloidogenic proteins through two distinct mechanisms: 1) increasing ER quality control stringency and 2) increasing extracellular proteostasis capacity by increasing secretion of the extracellular chaperone ERdj3[3,4]. This indicates that small molecule ER proteostasis regulators that preferentially activate ATF6 offer a unique opportunity to broadly treat amyloid diseases. Consistent with this prediction, our top small molecule ER proteostasis regulators 147 and 263 phenocopy the ability of stress-independent ATF6 activation to selectively reduce secretion of destabilized, amyloidogenic TTR and LC variants without impacting secretion of stable, non-amyloidogenic variants of these proteins or the global secreted proteome. This clearly demonstrates the therapeutic potential for our small molecule ER proteostasis regulators to attenuate proteotoxic extracellular aggregation associated with human amyloid diseases including Alzheimer's disease, Creutzfeldt-Jakob disease and related prion diseases, Light Chain Amyloidosis, the TTR amyloidosis and other amyloid diseases, e.g. gelsolin and lysozyme amyloidoses.

Intracellular Protein Aggregation Diseases (Gain-of-Proteotoxicity Protein Misfolding Diseases)

The intracellular aggregation of secretory proteins is also implicated in the onset and pathology of other gain-of-proteotoxicity diseases, including alpha-1-antitrypsin (A1AT) associated liver disease and retinal degeneration where destabilized A1AT variants and rhodopsin variants form proteotoxic intracellular aggregates[3,4]. Interestingly, genetic activation of ATF6 has been shown to attenuate the proteotoxic intracellular aggregation of the aggregation-prone A1AT-Z variant and disease-associated rhodopsin mutants, indicating that ATF6 activation offers a unique therapeutic approach to attenuate intracellular aggregation of proteotoxic proteins[9,10]. This demonstrates that our small molecule ER proteostasis regulators also have potential to ameliorate pathologic intracellular aggregation of disease-associated proteins.

Loss-of-Function Protein Misfolding Diseases (e.g., Cystic Fibrosis, Lysosomal Storage Diseases, Etc)

Unlike gain-of-proteotoxicity protein misfolding and/or aggregation diseases, many loss of function protein misfolding diseases result from the premature degradation of destabilized protein variants in the ER lumen before they are secreted. This premature degradation prevents their trafficking to downstream secretory environments, lowering their concentrations in functional compartments or in the extracellular space, lowering their native activity. In these diseases, the lack of protein function is predominantly responsible for pathology. Loss of function protein misfolding diseases include Cystic Fibrosis and related chanelopathies, nephrogenic diabetes insipidus, pain, and numerous lysosomal storage diseases, such as Gaucher disease and Fabry's disease, as well as the collagenopathies, including osteogenesis imperfect.

Importantly, the protein variants prematurely-degraded in loss of function protein misfolding diseases are often functional if they are allowed to traffic to their downstream secretory environments. This suggests that preventing premature degradation of these proteins offers a unique opportunity to increase their concentrations in downstream secretory environments, thus restoring their function. One potential strategy to achieve this goal is through remodeling of the ER proteostasis network. Consistent with this prediction, altering the activity of ER proteostasis pathways promotes the folding and trafficking of destabilized variants of glucocerebrosidase involved in Gaucher disease[11-15]. Similar results were also observed with mutants of beta hexominidase A (HexA) associated with Tay Sachs disease[16] and aminobutyric acid Type A GABA receptors associated with epilepsy[17,18]. This indicates that adapting ER proteostasis through additional mechanism such as arm selective UPR activation also offers a potential therapeutic opportunity to attenuate the premature degradation and promote the trafficking of disease-associated proteins involved in loss-of-function protein misfolding disorders[1]. Since our small molecule ER proteostasis regulators promote ER proteostasis through ATF6-mediated adaptation of ER proteostasis pathway activity, it is likely that our molecules will be able to correct the folding defects associated with loss-of-function protein misfolding diseases.

Cardiovascular Disease

ER stress and UPR activation is directly implicated in many cardiovascular disorders including ischemic-reperfusion injury, cardiac hypertrophy and failure, and atherosclerosis[19-23]. Significant evidence indicates that ATF6 activation is a potential therapeutic strategy to ameliorate pathologic heart dysfunction associated with these diseases. Activation of ATF6 is well-established to exert cardioprotective effects against ischemia-reperfusion injury in both in vitro and in vivo models[20,24-26]. Increasing the activity of ATF6 regulated genes including BiP, MANF, or DERL3 also protects cardiomyocytes from ER stress induced dysfunction and apoptosis associated with I/R injury[27-29]. ATF6 activation has also been shown to be protective in mouse models of pressure overload hypertrophy by balancing adaptive responses to growth stimuli[19,30]. Similarly, increasing the activity of ATF6-regulated genes such as RCAN1 in transgenic mouse hearts attenuates pressure overload induced cardiac hypertrophy by inhibiting CaN/NFAT signaling[19,31,32]. The above highlighted results demonstrate the therapeutic potential for small molecule ER proteostasis regulators that preferentially activate the ATF6 arm of the UPR to alleviate cardiac ER stress and promote cardiac function in response to pathologic cardiovascular disease.

Diabetes and Metabolic Disorders

ER stress in pancreatic beta cells is directly implicated in the onset and pathogenesis of Type II diabetes (T2D)[33-35]. In this disease, there is a loss of pancreatic beta cell mass that results from prolonged activation of the UPR and subsequent terminal UPR signaling to apoptosis. Interestingly, exogenous ATF6 activation has potential to ameliorate the chronic ER stress associated with pancreatic beta cell loss. In response to ER stress, the UPR initially activates an adaptive, protective transcriptional program that promotes ER proteostasis. This adaptive response is mediated by the UPR-regulated transcription factors XBP1s and ATF6. Chronic ER stress leads to further UPR activation to a pro-apoptotic signaling pathway that induces apoptosis predominantly through the PERK arm of the UPR. Thus, one strategy to ameliorate ER stress induced beta cell apoptosis is by increasing the duration of adaptive UPR signaling afforded by transcription factors such as ATF6[33,34]. Consistent with this model, mutations in ATF6 that disrupt ATF6 function predispose individuals to T2D[36]. Overexpression of the ATF6-regulated chaperone BiP in mouse pancreatic beta cells also attenuates high fat diet induced obesity, glucose intolerance, hyperinsulinemia, and insulin resistance in vivo[37]. Similarly, overexpression of ATF6-regulated chaperones such as BiP and PDI in pancreatic beta cell models highly expressing the amyloidogenic islet amyloid polypeptide (IAPP)—a protein that aggregates into amyloid fibrils in 90% of T2D patient islets—also attenuates IAPP aggregate-induced ER stress and increases insulin secretion in INS1 pancreatic beta cells[38]. Furthermore, ATF6 regulates the expression of other genes shown to be protective against ER-stress induced pancreatic beta cell death such as DNAJC3[39,40] and WFS1[41,42]. Apart from T2D, ATF6 activation could also beneficial in protecting beta cells in autoimmune Type I diabetes (T1D). Recent evidence shows that the addition of the chemical chaperone TUDCA attenuates diabetes incidence through a mechanism dependent on ATF6 in 2 different T1D animal models[43].

Apart from protecting beta cells in diabetes, ATF6 activation can also attenuate other diabetic phenotypes such as the cardiac hypertrophy associated with the high morbidity and mortality rates in the diabetic population[44]. Overexpression of a dominant negative ATF6 in mice induces dilated cardiomyopathy and cardiac dysfunction[25], indicating that ATF6 activation is protective in the diabetic heart. This suggests that exogenous ATF6 activation could be cardioprotective and ameliorate cardiac defects in diabetes patients. Exogenous ATF6 activation could also attenuate the ER-stress associated hepatic accumulation of fatty acids involved in diabetic hepatic steatosis[34,35]. Similarly, ATF6 activation could alleviate ER stress-induced phenotypes in other tissues such as adipocytes and skeletal muscle associated with diabetes[34].

ATF6 activation also has the potential to ameliorate ER stress induced phenotypes associated with other types of metabolic diseases including obesity, non-alcoholic fatty liver disease and inflammatory bowel disease (IBD)[35,46]. Hepatic ATF6 attenuates gluconeogenesis in the liver and hepatic ATF6 overexpression in obese mice reduces blood glucose and improves glucose tolerance[47]. Furthermore, ATF6 is protective against hepatic steatosis induced by acute ER stress or high fat diet[48]. Consistent with this model, overexpression of the ATF6-regulated chaperone BiP reduces liver lipogenesis[49]. Furthermore, ATF6 activation appears to be protective against dextran sodium sulfate-induced colitis, indicating ATF6 activation could be a therapeutic strategy to intervene in IBD[50].

The evidence discussed above clearly demonstrates that ATF6 activation in disease-associated, metabolically-challenged hepatic, pancreatic, adiopocyte or muscle tissues could be an extremely powerful strategy to ameliorate pathologies associated with metabolic disorders such as diabetes, obesity, IBD and hepatic steatosis. Our ability to induce preferential ATF6 activation using small molecule ER proteostasis regulators strongly indicates that these molecules represent a new potential therapeutic strategy to ameliorate disease pathology in diabetic patients.

Eye Disease

Recently, genetic studies have shown that mutations in ATF6 are causatively associated with eye diseases including achromatopsia and photoreceptor degeneration[51-53]. Interestingly, disease-associated ATF6 mutations are found throughout the ATF6 structure and can disrupt ATF6 activity through a number of mechanisms such as impaired trafficking to the Golgi[53]. The ability for our small molecules to promote ATF6 activation independent of ER stress indicates that the addition of our top molecules provide a new potential therapeutic opportunity to promote ATF6 activation and attenuate pathologic imbalances in ATF6 signaling that lead to these eye disorders.

Tables

TABLE 1

Prioritized ER proteostasis regulators

| Name | Structure | MW | Polar Surface Area | AlogP | Structural moieties (FIG. 1E) | % ERSE-FLuc activation* | % XBP1-RLuc activation* | Promiscuity** |
|---|---|---|---|---|---|---|---|---|
| 5 | 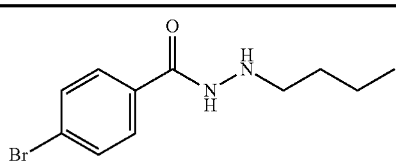 | 271.2 | 41.13 | 2.62 | — | 60.9 ± 6.0 | 9.1 ± 0.7 | 1 out of 31 |
| 132 | 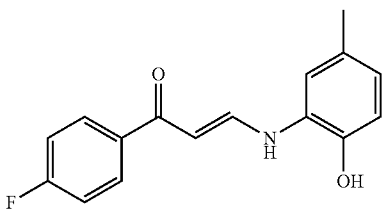 [SMILES: Cc1ccc(O)c(N/C=C/C(=O)c2ccc(F)cc2)c1] | 283.3 | 58.56 | 3.27 | F | 140.1 ± 17.4 | 10.3 ± 7.9 | 2 out of 32 |
| 145 | 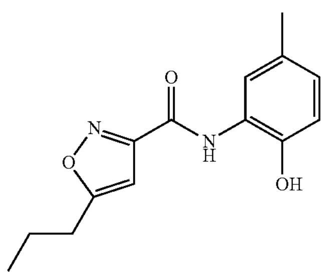 [SMILES: CCCc1cc(C(=O)Nc2cc(C)ccc2O)no1] | 260.3 | 75.36 | 3.01 | F, H | 83.4 ± 6.3 | 24.5 ± 4.7 | 1 out of 31 |
| 147 | 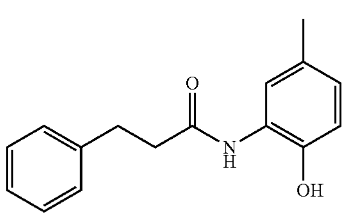 [SMILES: Cc1ccc(O)c(NC(=O)CCc2ccccc2)c1] | 255.3 | 49.33 | 3.35 | B, F | 63.2 ± 0.6 | 17.5 ± 1.9 | 1 out of 32 |
| 148 | 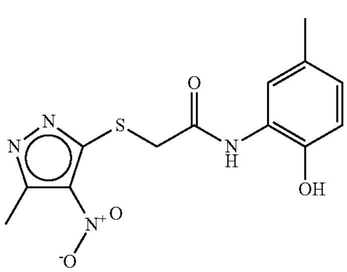 | 322.3 | 149.12 | 2.00 | B, F | 52.5 ± 14.3 | 16.6 ± 2.4 | 3 out of 31 |

TABLE 1-continued

Prioritized ER proteostasis regulators

| Name | Structure | MW | Polar Surface Area | AlogP | Structural moieties (FIG. 1E) | % ERSE-FLuc activation* | % XBP1-RLuc activation* | Promiscuity** |
|---|---|---|---|---|---|---|---|---|
| 238 | 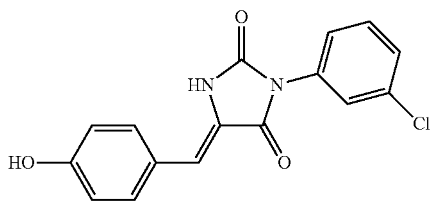 [SMILES: O=C1N/C(=C\c2ccc(O)cc2)C(=O)N1c1cccc(Cl)c1] | 314.7 | 69.64 | 2.94 | B, L | 68.2 ± 5.7 | 61.1 ± 0.1.5 | 2 out of 31 |
| 258 | 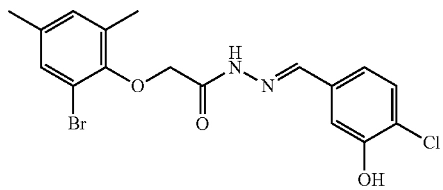 [SMILES: Cc1cc(C)c(OCC(=O)N/N=C/c2ccc(Cl)c(O)c2)c(Br)c1] | 393.2 | 91.15 | 3.76 | C, D | 28.6 ± 6.1 | 32.6 ± 1.0 | 1 out of 31 |
| 263 | 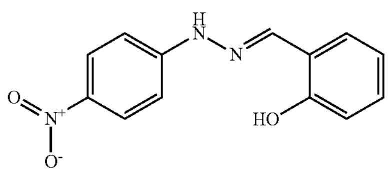 [SMILES: O=[N+]([O-])c1ccc(N/N=C/c2ccccc2O)cc1] | 257.2 | 90.44 | 3.10 | C | 20.7 ± 2.3 | 2.4 ± 1.0 | 1 out of 31 |

*% Tg activation from triplicate confirmation screen at 6.8 μM
**Number of screening assays in which the compound was found active

TABLE 2

Select mRNA-Seq fold changes (relative to Vh) for ER and cytosolic proteostasis genes

| Gene Name | Function | Tg | 132 | 147 | 263 | ATF6 |
|---|---|---|---|---|---|---|
| | | ATF6-Selective Genes | | | | |
| BiP | ER HSP70 Chaperone | 11.6 | 9.1 | 3.3 | 5.7 | 10.6 |
| GRP94 | ER HSP90 Chaperone | 4.2 | 3.5 | 1.8 | 2.5 | 6.0 |
| SEL1L | ER Degradation Factor | 7.6 | 4.9 | 2.2 | 2.7 | 8.7 |
| | | XBP1s-Selective Genes | | | | |
| SEC24D | COPII Subunit | 6.6 | 3.1 | 1.4 | 2.1 | 1.1 |
| HSPA13 | ER HSP70-like Protein | 4.2 | 2.6 | 1.2 | 1.7 | 1.0 |
| DNAJC10 | ER HSP40 Co-chaperone | 2.1 | 1.4 | 1.1 | 1.3 | 1.1 |
| | | XBP1s- or ATF6-Target Genes | | | | |
| HYOU1 | Nucleotide Exchange Factor | 6.1 | 3.6 | 1.8 | 2.7 | 4.8 |
| ERdj3 | ER HSP40 Co-chaperone | 4.0 | 2.9 | 1.7 | 2.4 | 3.9 |
| p58IPK | ER HSP40 Co-chaperone | 3.9 | 3.7 | 1.8 | 2.9 | 3.3 |
| | | PERK Target genes | | | | |
| DDIT3 | CHOP; Transcription Factor | 13.2 | 10.6 | 1.7 | 2.0 | 3.6 |
| TrIB3 | Transcription Factor | 8.2 | 5.8 | 1.0 | 1.3 | 1.0 |
| ASNS | Asparagine Synthetase | 4.2 | 2.7 | 1.0 | 1.5 | 1.0 |
| | | HSF1 Target Genes | | | | |
| DNAJB1 | Cytosolic HSP40 Co-chaperone | 0.5 | 3.0 | 1.6 | 1.4 | 1.3 |
| HSPA8 | Cytosolic HSP70 | 0.3 | 1.5 | 1.3 | 1.3 | 0.9 |
| HSPA1A | Cytosolic HSP70 | 0.3 | 9.3 | 3.2 | 2.5 | 1.3 |

Structure-Activity Relationship Study on the 2-Amino-p-Cresol Amide Small Molecule ER Proteostasis Regulators Identifies Critical Substructures Required for ATF6 Activation.

Many of the small molecule ER proteostasis regulators found to preferentially activate the ATF6 reporter in our primary screen, molecules surviving counter screening and further scrutiny, contained a 2-amino-p-cresol substructure (cluster F in FIG. 1e). This particular substructure was substantially over-represented in many of our top hits from the ATF6 reporter screen and comprises one of our top molecules (e.g., 147) implying that 2-amino-p-cresol could be critical for the activity of these small molecules.

We first devised a synthetic strategy to synthesize compounds similar to 147, and structurally related derivatives, to begin to establish a structure-activity relationship. Briefly, commercially available carboxylic acid Z was activated to the acyl halide, followed by coupling with commercially available 2-amino-p-cresol T to give synthetic compound 147 (FIG. 7a). This flexible synthetic approach allowed us to prepare a series of 147 analogs in a similar fashion (147a-m, FIG. 7a,b,d) to explore the involvement of the 2-amino-p-cresol moiety and the structural requirements for the activity of these molecules. We then monitored the activation of the ERSE-FLuc ATF6 reporter in HEK293T-Rex cells treated with these molecules (FIG. 7c,e).

Importantly, the resynthesized hit from the library, compound 147 demonstrated identical, preferential activation of the ERSE-FLuc reporter to that observed using the purchased hit compound, further confirming the activity of this molecule (FIG. 7c). We next wanted to explore whether the 2-amino-p-cresol substructure in its entirety is necessary for activity by testing analogs 147a-147f (FIG. 7b), in which either the phenol or methyl group is deleted (147a,b), the phenol is converted to a fluorine or the methyl is converted to a CF3 group (147c,d) or the phenol is relocated on the aromatic ring (147e,f). In all cases, ATF6 activation was eliminated as discerned by the ERSE-FLuc reporter by the disruption or modification of this key 2-amino-p-cresol pharmacophore (FIG. 7c). Collectively, these structure-activity relationships confirm the importance of the 2-amino-p-cresol moiety for ATF6 activation.

We next evaluated whether the 2-amino-p-cresol moiety alone was sufficient to activate the ATF6 arm of the UPR as measured by the ERSE-FLuc reporter using a series of 147 analogs featuring variable linking substructures between the two aryl rings (147g-j, FIG. 7d). Notably, either decreasing or increasing the distance between the 2-amino-p-cresol and the remaining or second aryl ring by adding or removing $CH_2$ groups (147g-i) or modifying the linker by introducing unsaturation (147j) substantially reduced ATF6 activation as discerned by the ERSE-FLuc reporter (FIG. 7e). These results clearly show that the presence of a 2-amino-p-cresol moiety is not sufficient to activate ATF6, as activity is also sensitive to spacing and orientation of both phenyl rings present in the parent molecule. We further examined perturbing the electronics of the second aryl ring by testing a series of brominated derivatives (147k-m, FIG. 7d,e). While substituting a bromine for a H in the para or meta position significantly reduced ERSE-FLuc reporter activity, an ortho-bromine was compatible with ATF6 activation (FIG. 7e). This result implies that there is room to optimize the electronics and other features of the second aryl ring, which is also reflected by the substantial diversity in that part of the molecule as observed by other top hits in our screen (Table 1).

Figure 8A:
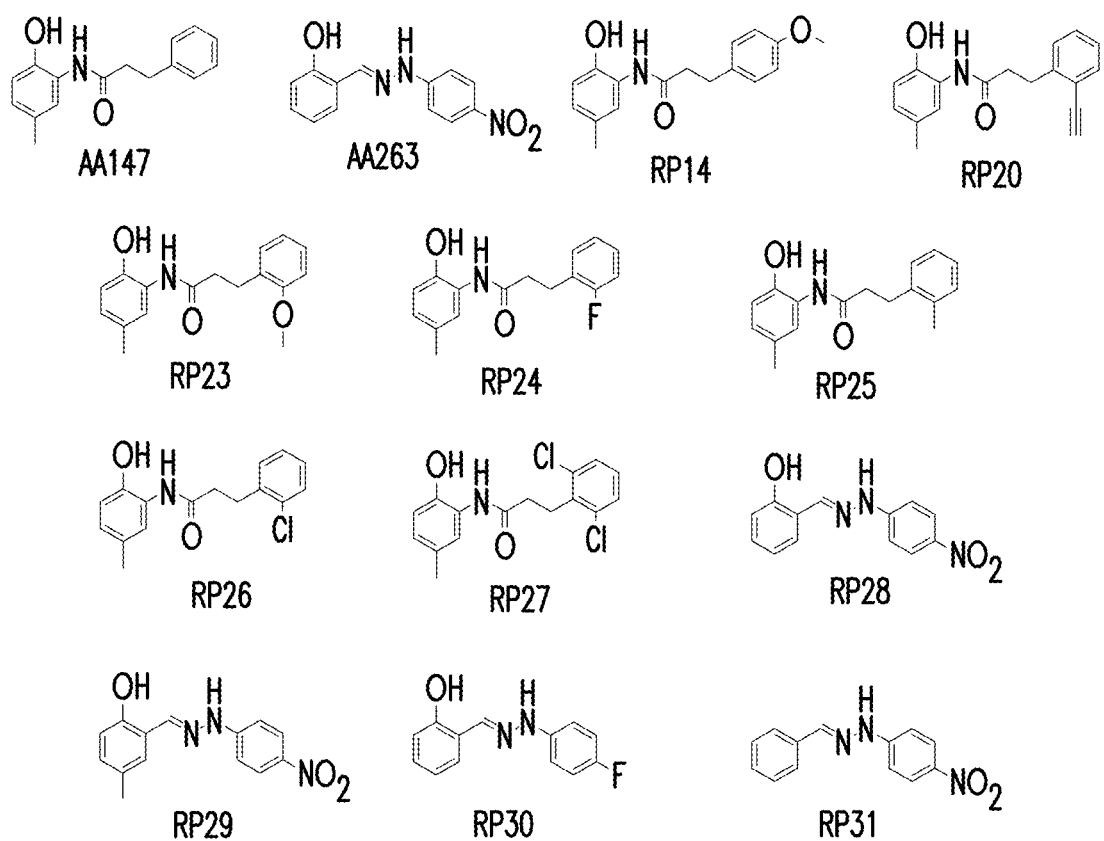
FIG. 8A. Structures of synthesized 147 and 263 analogs.

We evaluated several more modifications to the second phenyl ring distal to the 2-amino-p-cresol aryl ring to optimize its electronics. Interestingly electron withdrawing groups located in the ortho-position (RP24 and RP26, FIGS. 8a,b) seem to increase the compounds propensity to activate the ATF6 arm of the UPR as discerned by the ERSE reporter relative to 147, however, a doubly ortho-chlorinated analogue (RP27) decreases activity relative to the chemically synthesized 147 (FIG. 8a,b). This is in contrast to electron donating groups located on the phenyl ring, which slightly decrease or do not change reporter activity relative to 147 (RP8, RP14, RP23, RP25, FIG. 8a,b) Furthermore, we developed an alkyne probe (RP20, FIG. 8a,b) that can be conjugated to biotin or fluophores to attempt to affinity purify interacting proteins including the target of these small molecules.

Figure 8B:
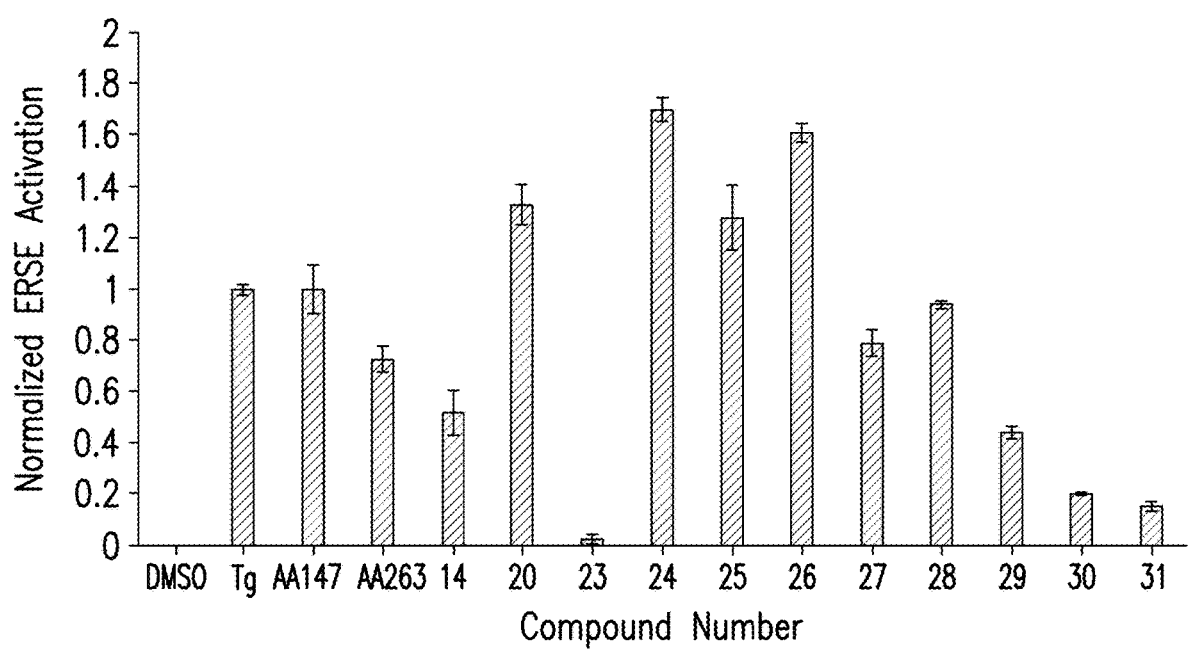
FIG. 8B. Plots showing ERSE-FLuc activation in HEK293T-Rex cells stably expressing ERSE-FLuc treated with vehicle, Tg (1 µM), or synthesized analogs of 147 (14-31 all 10 µM). Luminescence is shown normalized to thapsigargin. Error bars show standard deviation from n=3 replicates.
Figure 8C:
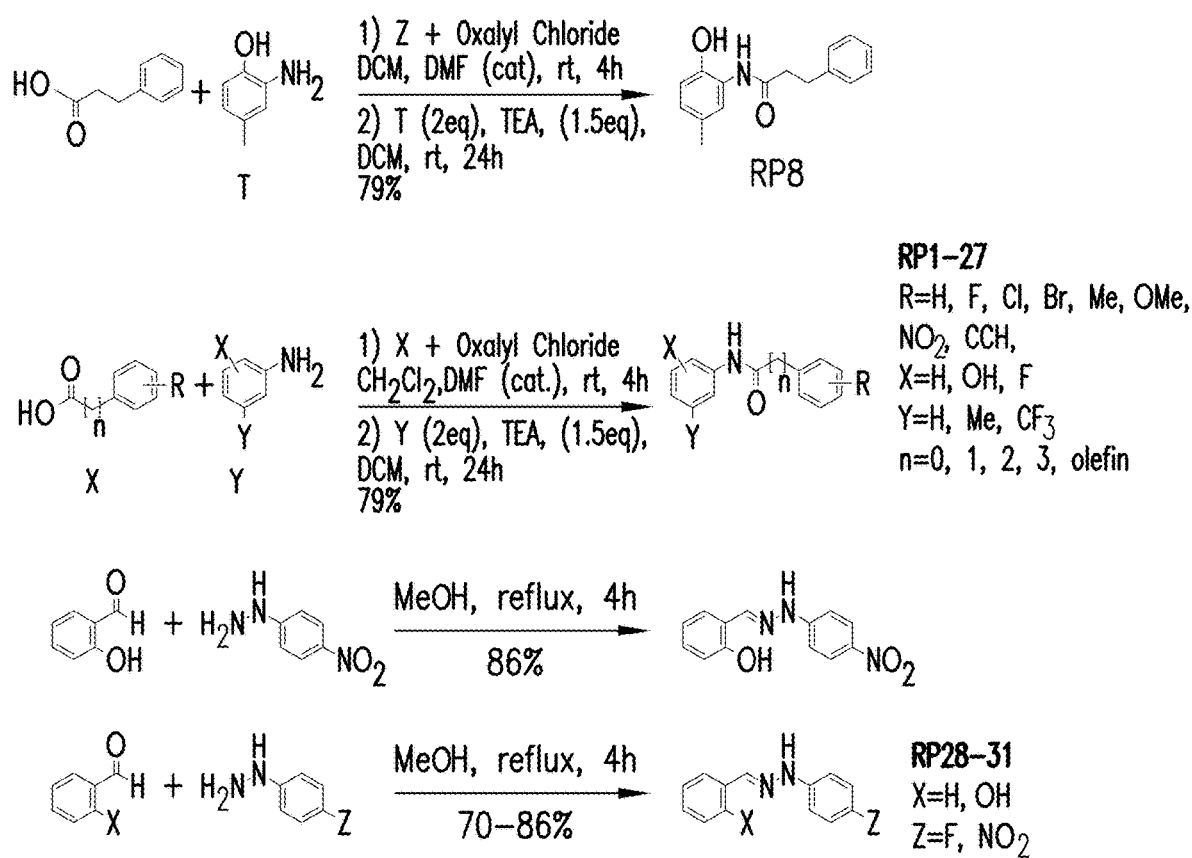
FIG. 8C. Synthetic overview for making analogs of 147 and 263.
Figure 9B:
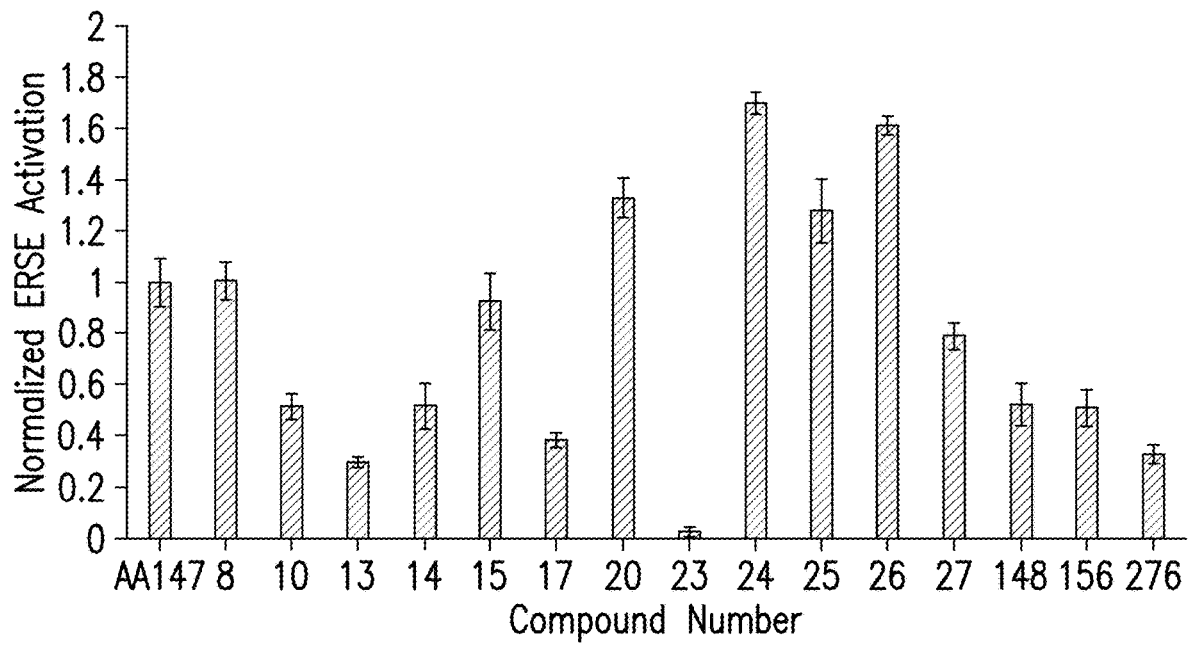
FIG. 9 depicts (FIG. 9A) structures of compounds formula (I), (FIG. 9B) and (FIG. 9C) show bar graphs of bioactivities of those compounds. This figure is a summary of all of the SAR data on derivatives of compounds 147 and 263, combining the ERSE-FLuc reporter activation data from FIG. 7 and FIG. 8 for ease of comparison. The graphs display activation of the ERSE-Fluc reporter in HEK293T-Rex cells after treatment with the respective compound (10 µM) for 16 h. Luminescence is shown normalized to thapsigargin treatment. Error bars represent standard error from n=3 replicates.
Figure 9C:
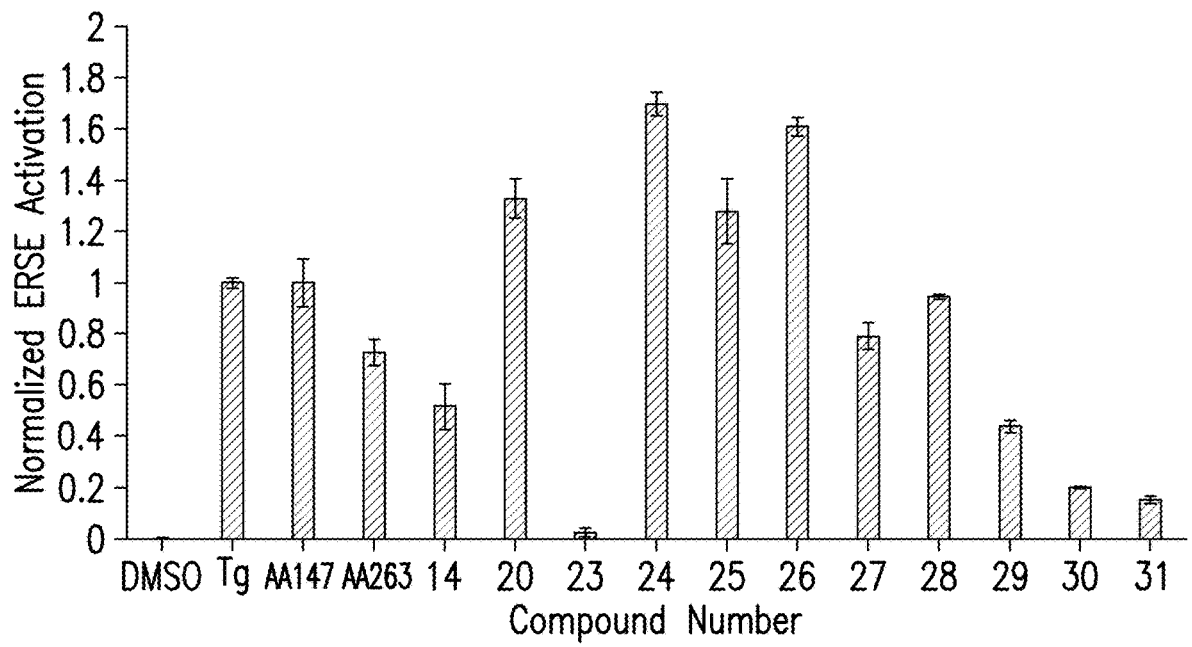
Figure 10A:
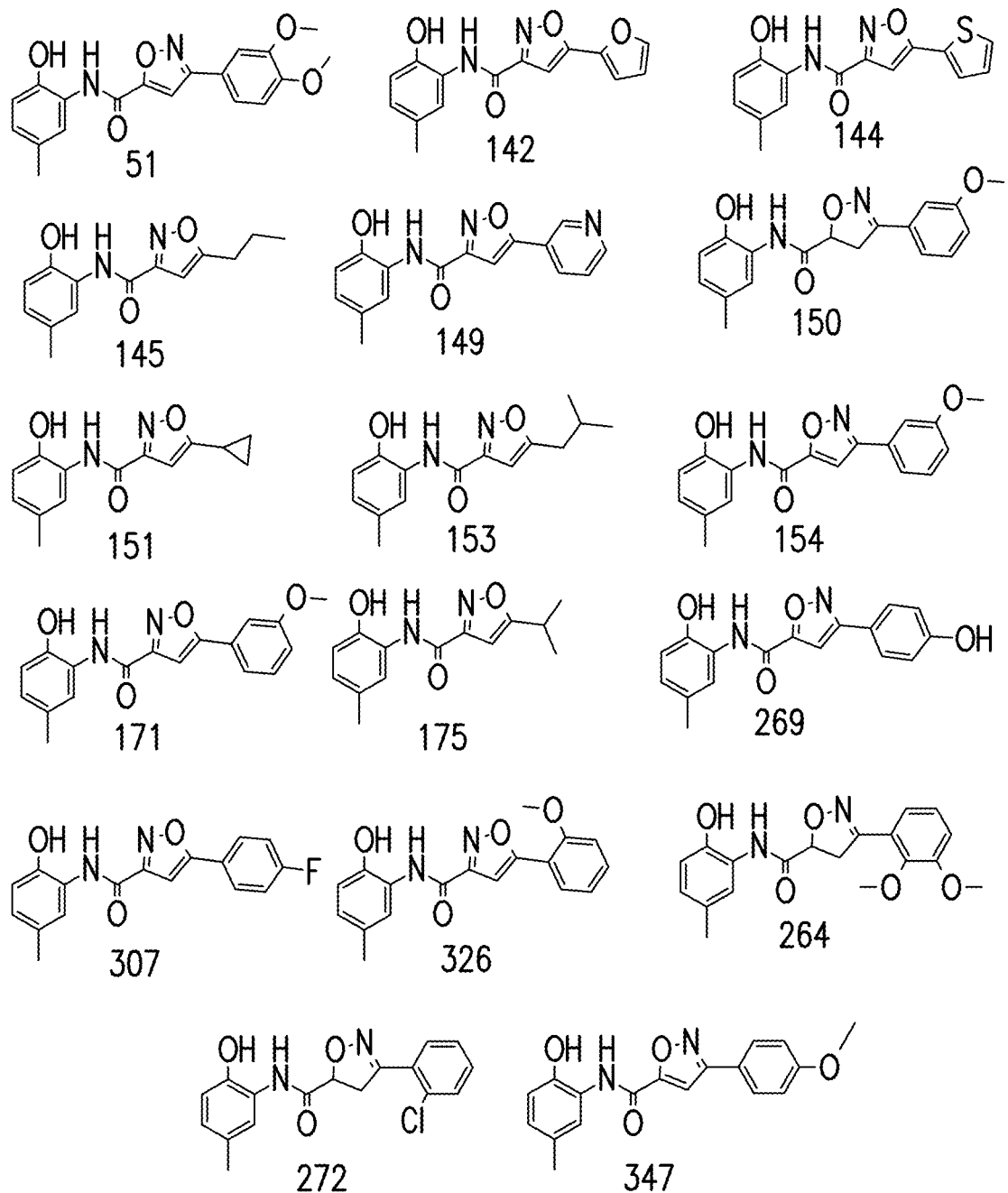
FIG. 10 depicts (FIG. 10A) structures of compounds formula (IIA) and (IIB), (FIG. 10B) a bar graph of bioactivities of those compounds, presented analogously to data of FIG. 9.
Figure 10B:
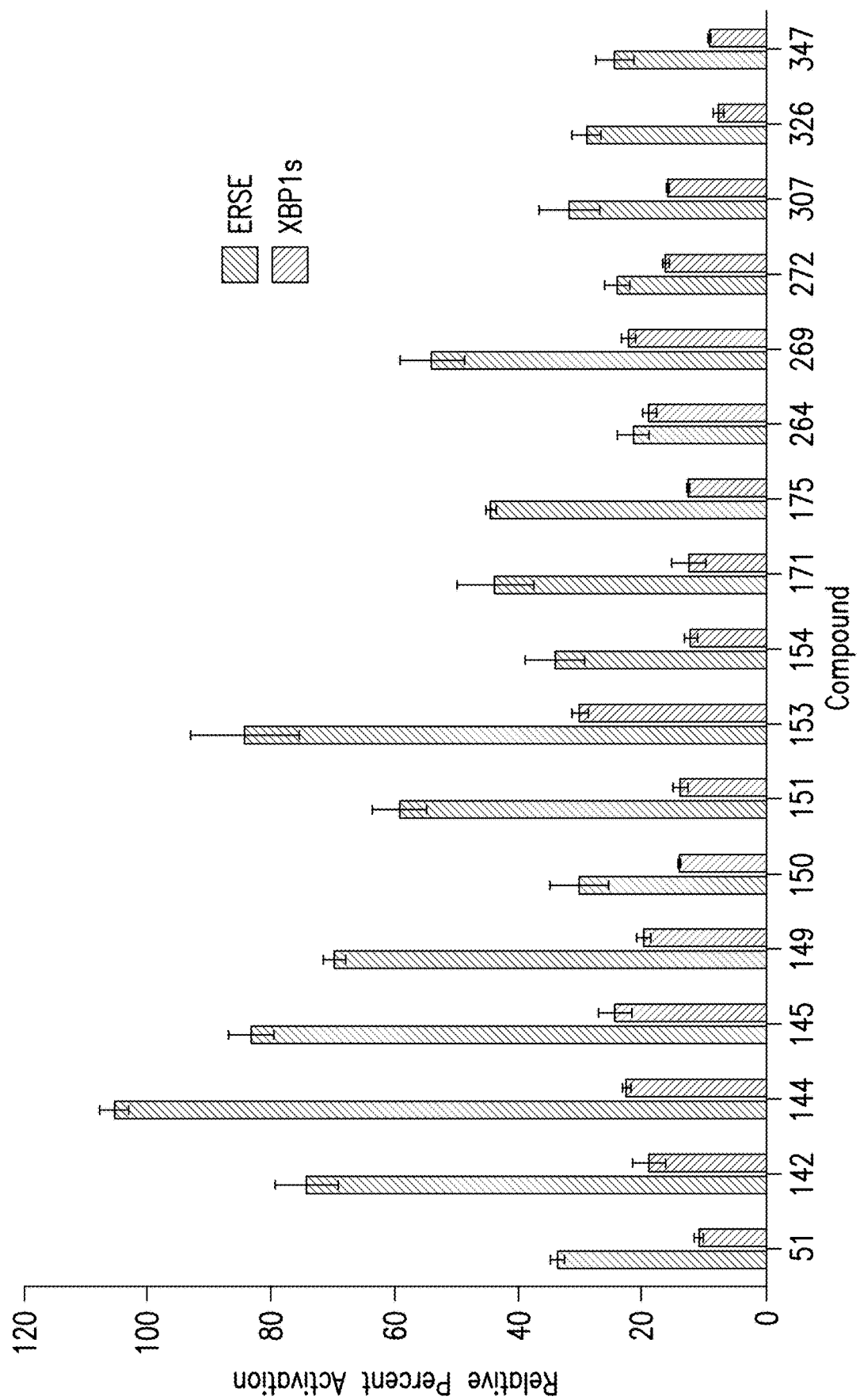
Figure 11A:
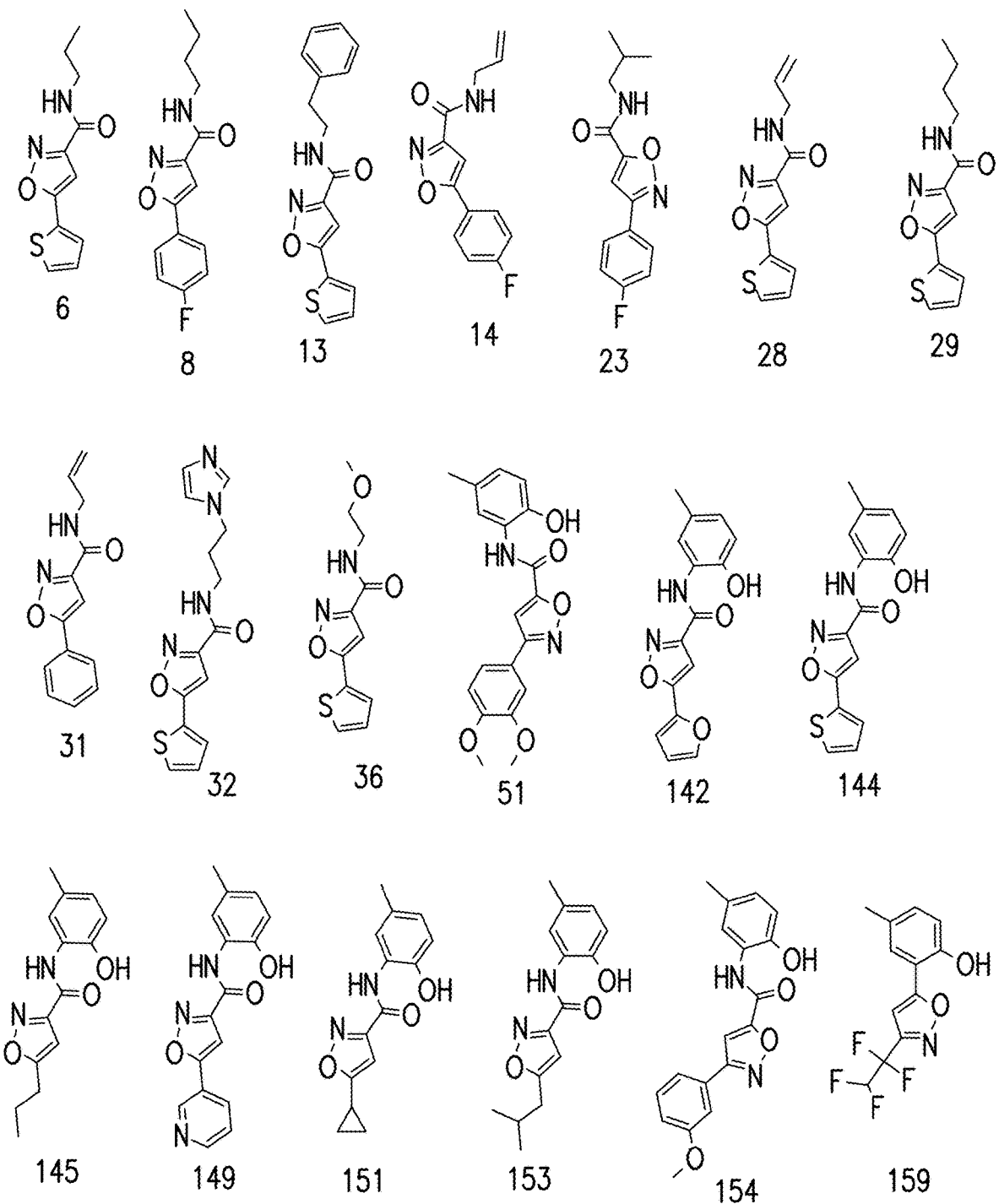
FIG. 11 depicts (FIG. 11A and FIG. 11B) structures of compounds formula (IIIA) and (IIIB), and (FIG. 11C) a bar graph of bioactivities of those compounds, presented analogously to data of FIG. 9.
Figure 11B:
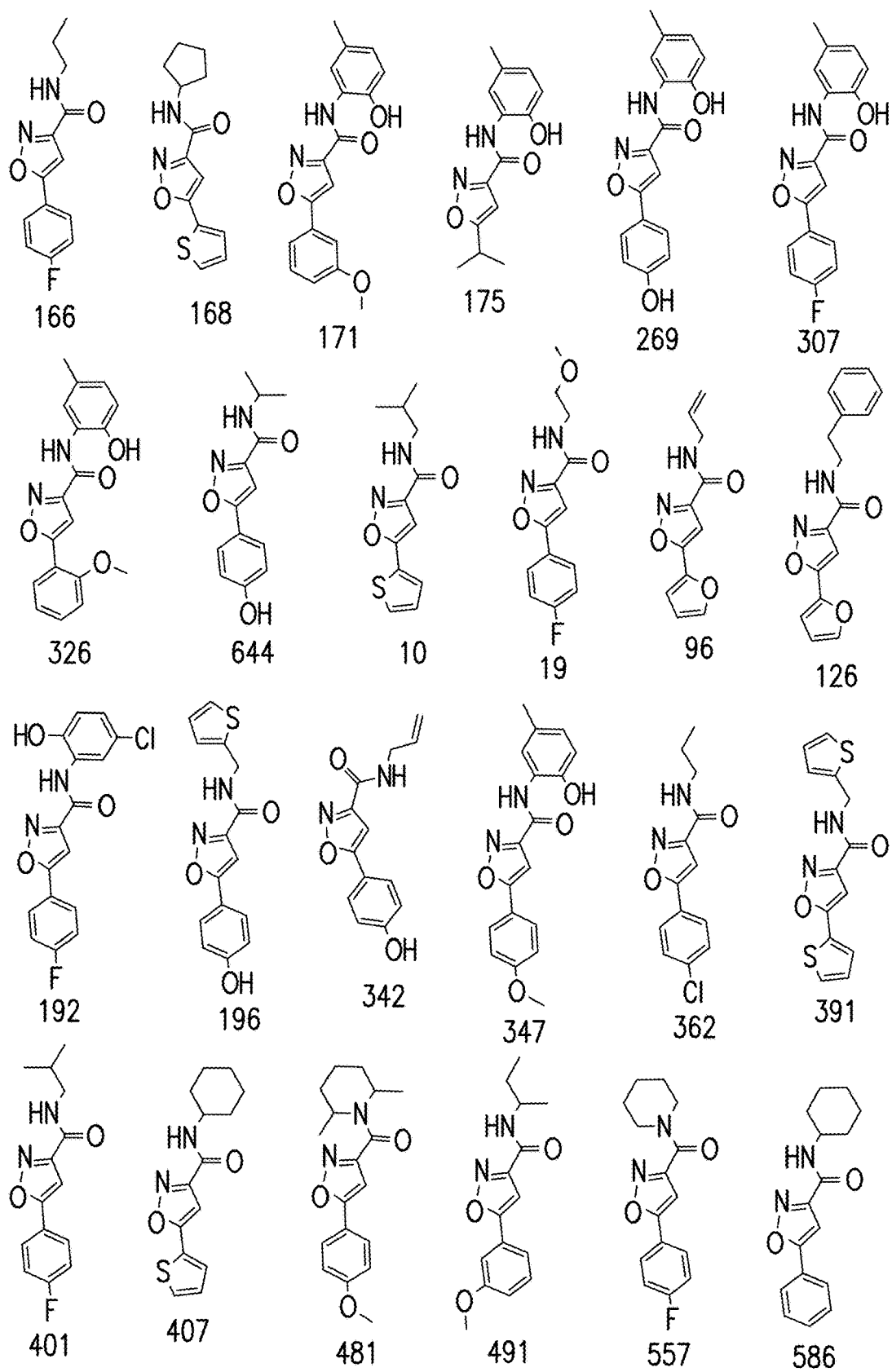
Figure 11C:
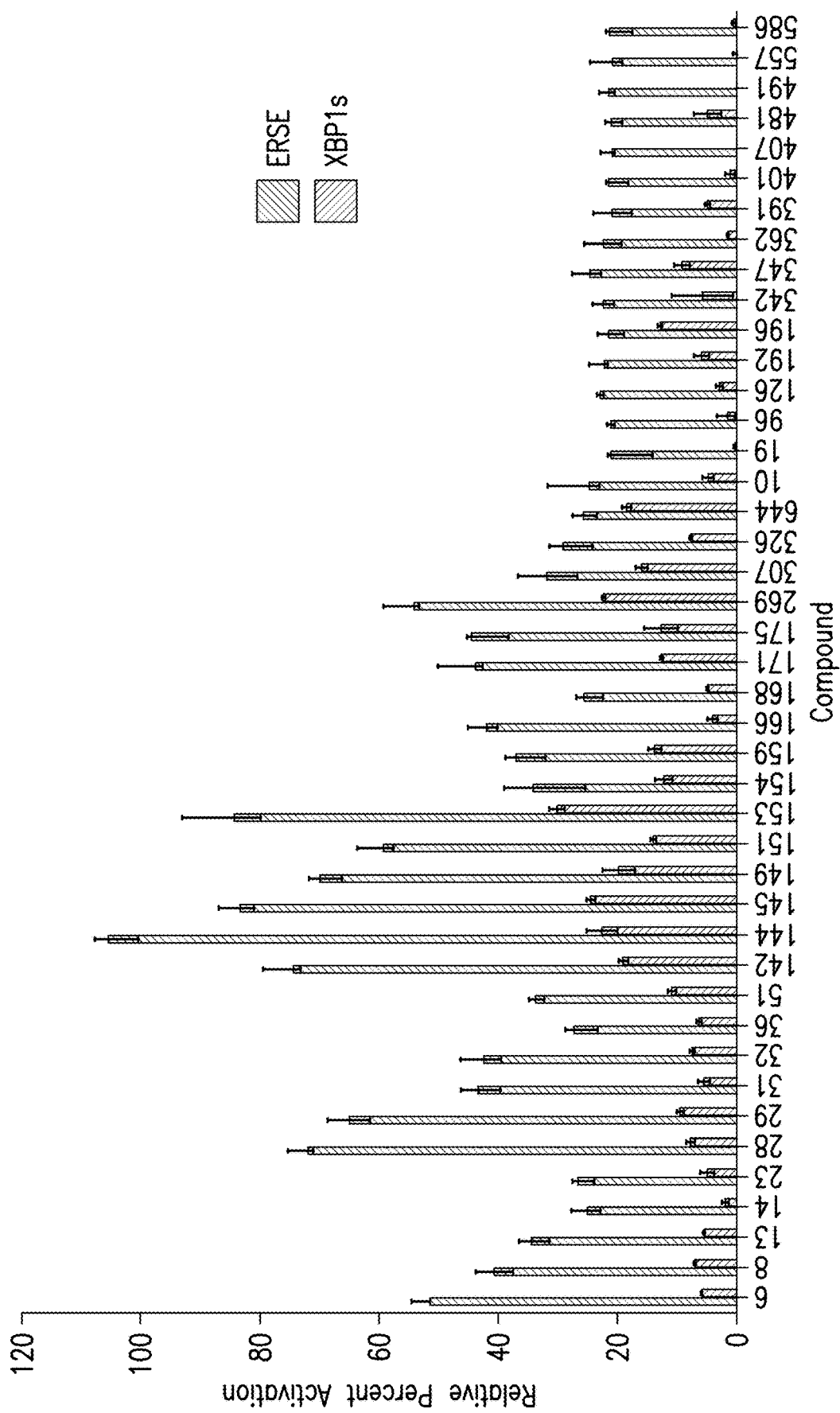
Figure 12A:
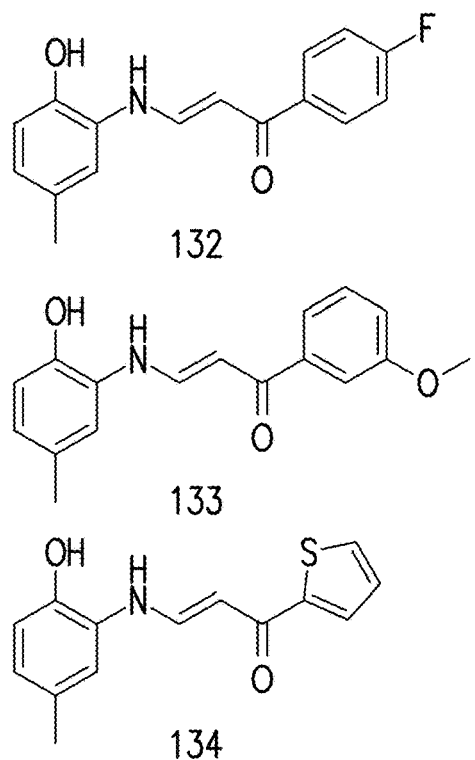
FIG. 12 depicts (FIG. 12A) structures of compounds formula (IV), and (FIG. 12B) a bar graph of bioactivities of those compounds, presented analogously to data of FIG. 9.
Figure 12B:
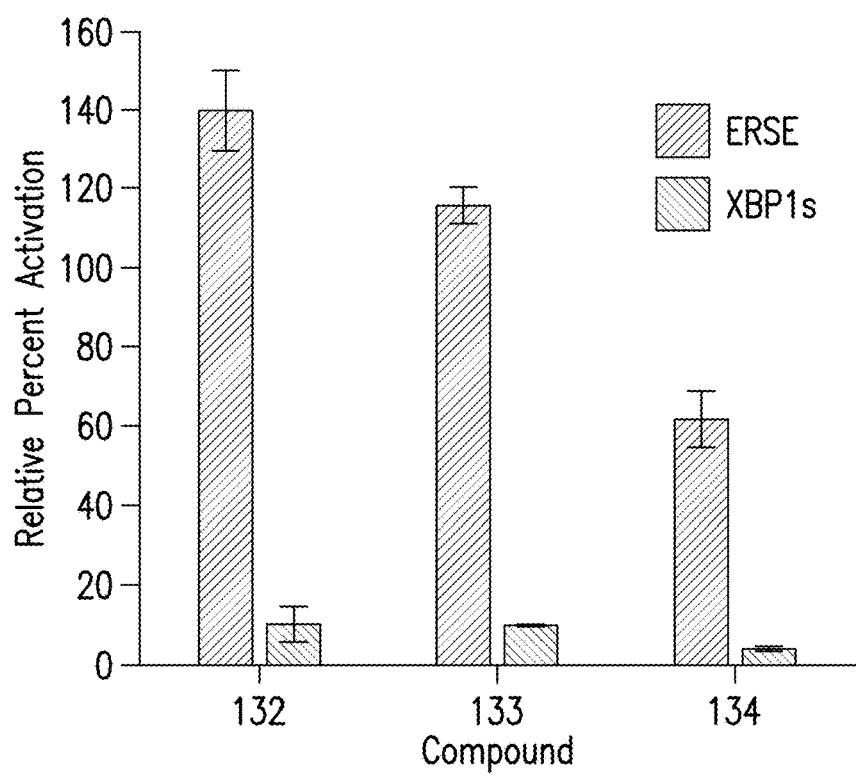
Figure 13A:
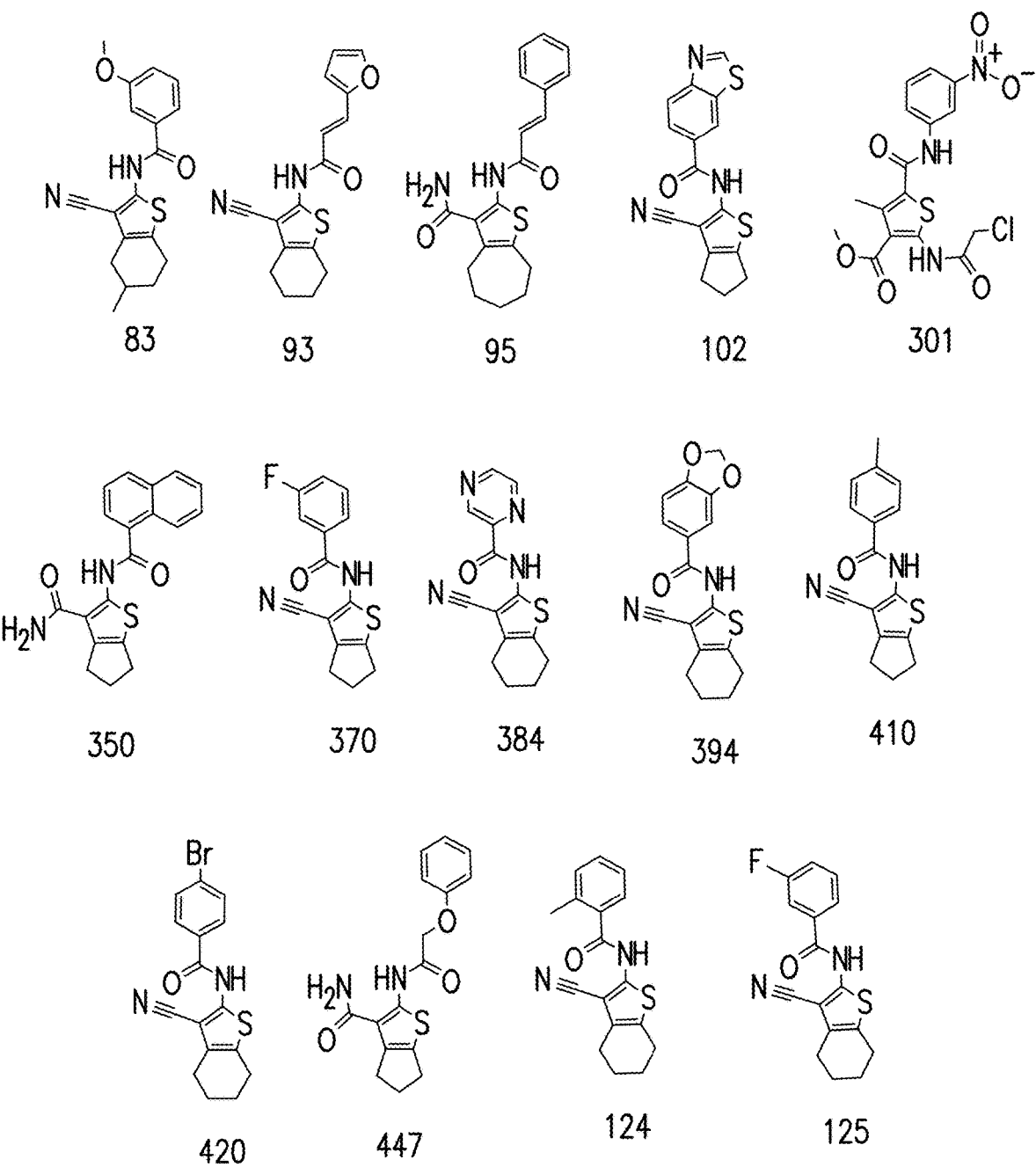
FIG. 13 depicts (FIG. 13A) structures of compounds formula (V), and (FIG. 13B) a bar graph of bioactivities of those compounds, presented analogously to data of FIG. 9.
Figure 13B:
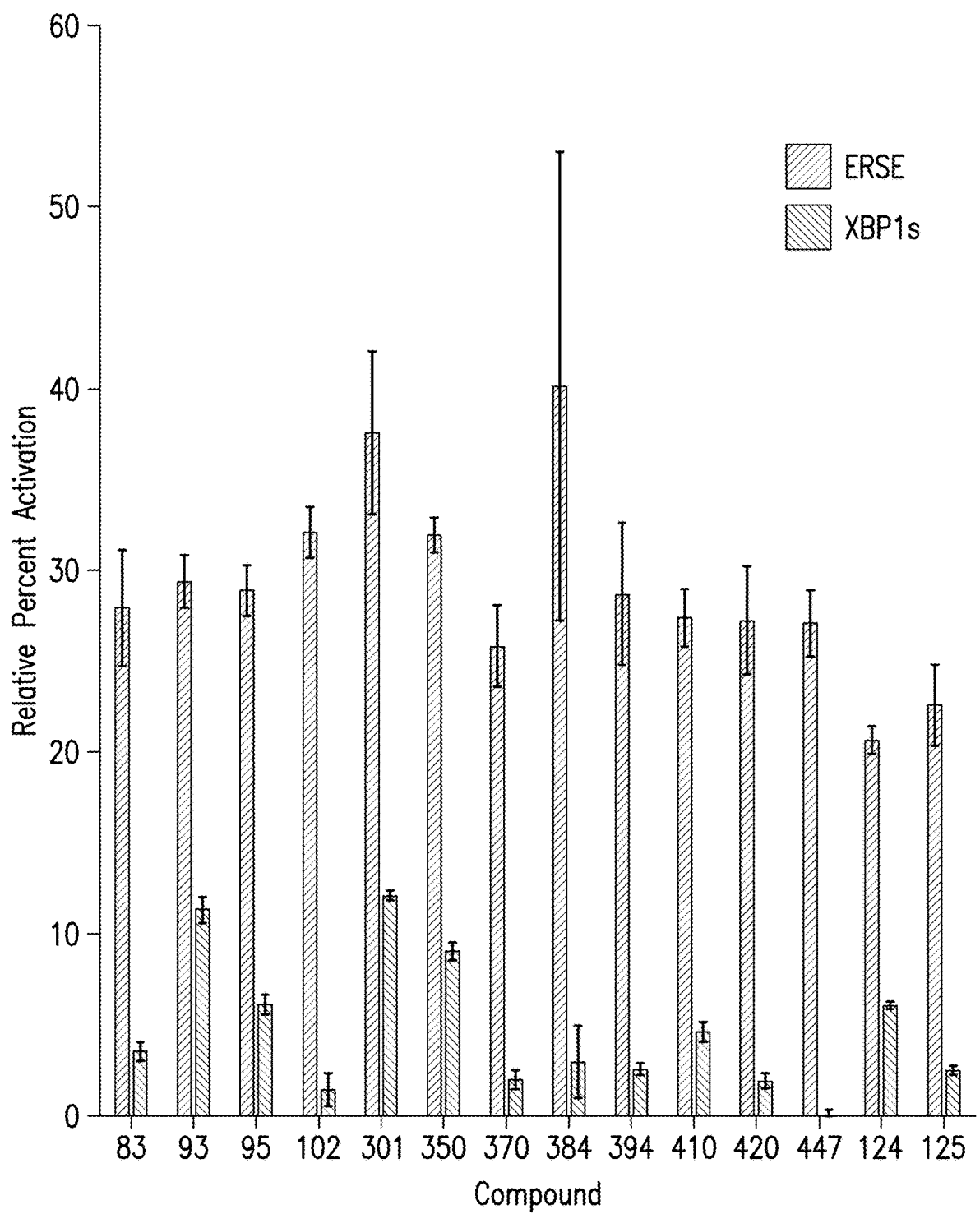
Figure 14A:
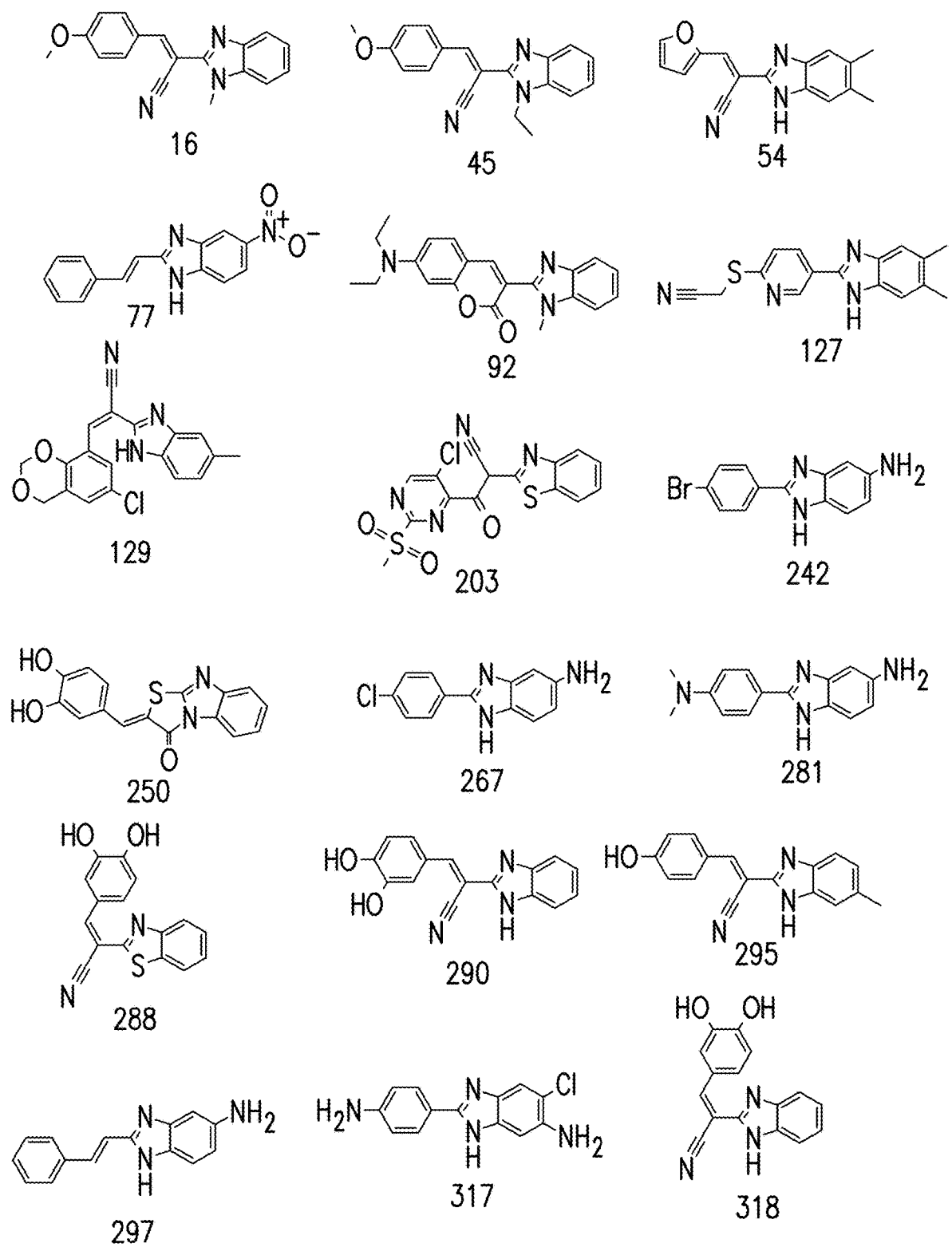
FIG. 14 depicts (FIG. 14A, FIG. 14B, FIG. 14C) structures of compounds formula (VIA) and (VIB) and (VIC), and (FIG. 14D) a bar graph of bioactivities of those compounds, presented analogously to data of FIG. 9.
Figure 14B:
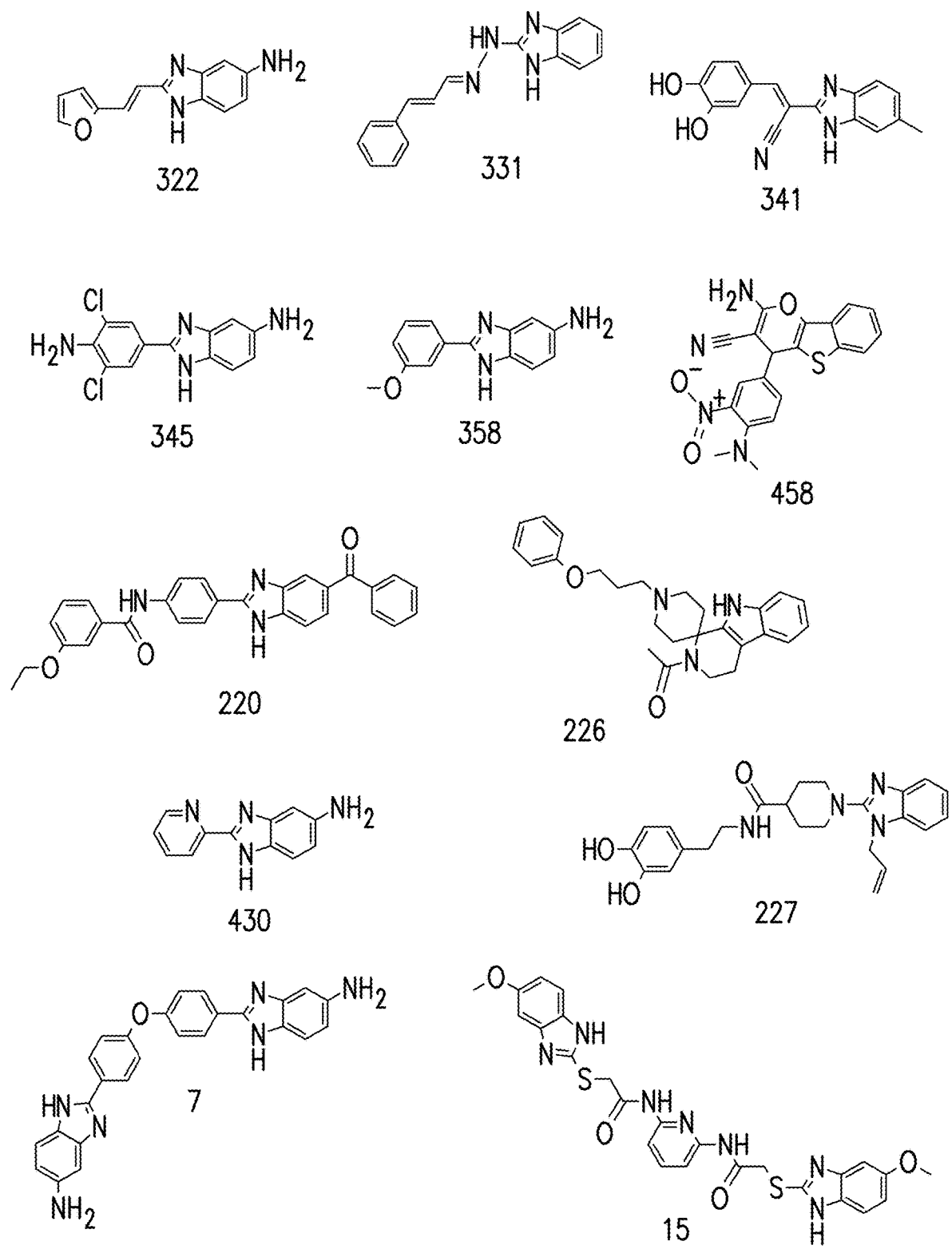
Figure 14C:
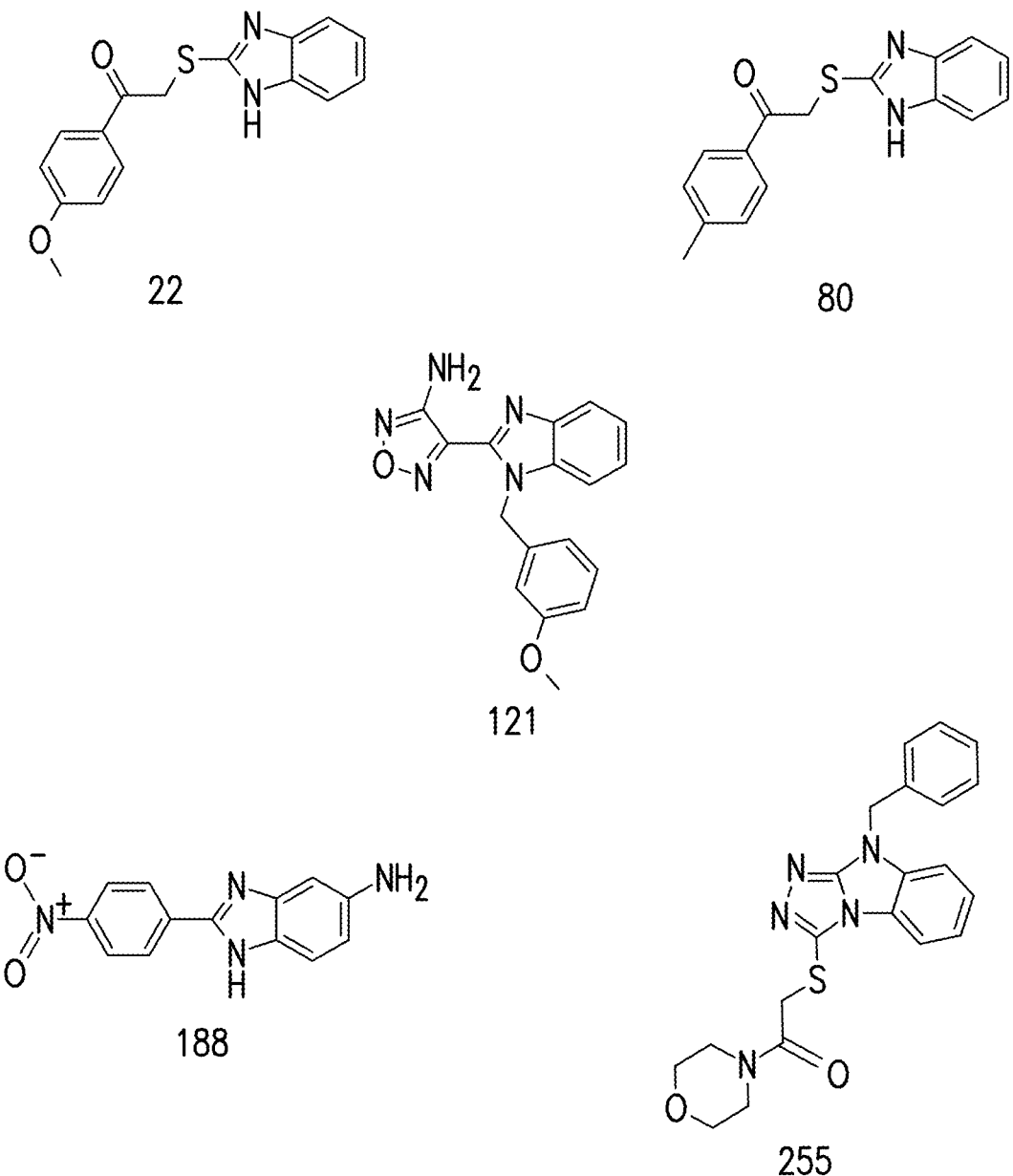
Figure 14D:
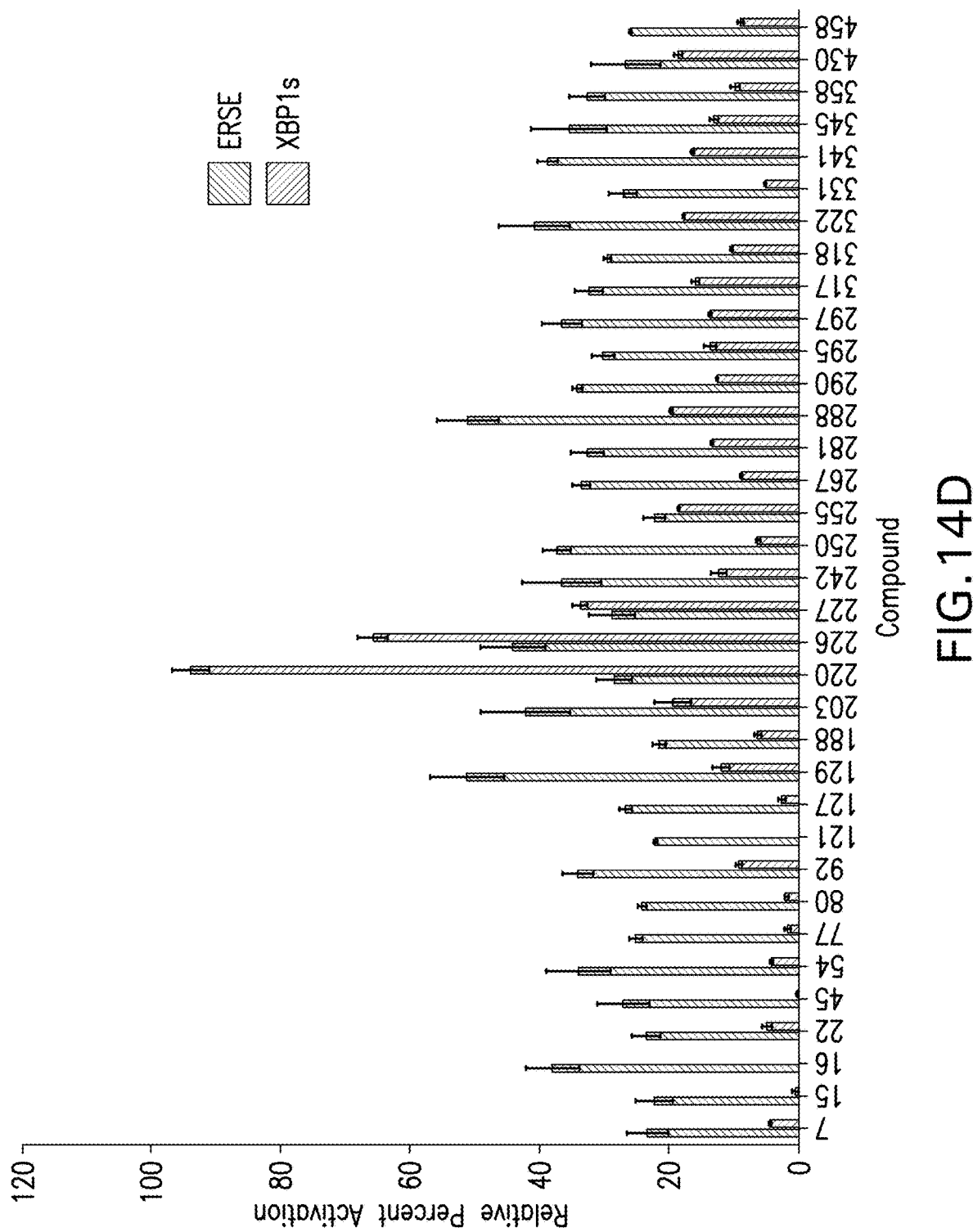
Figure 15A:
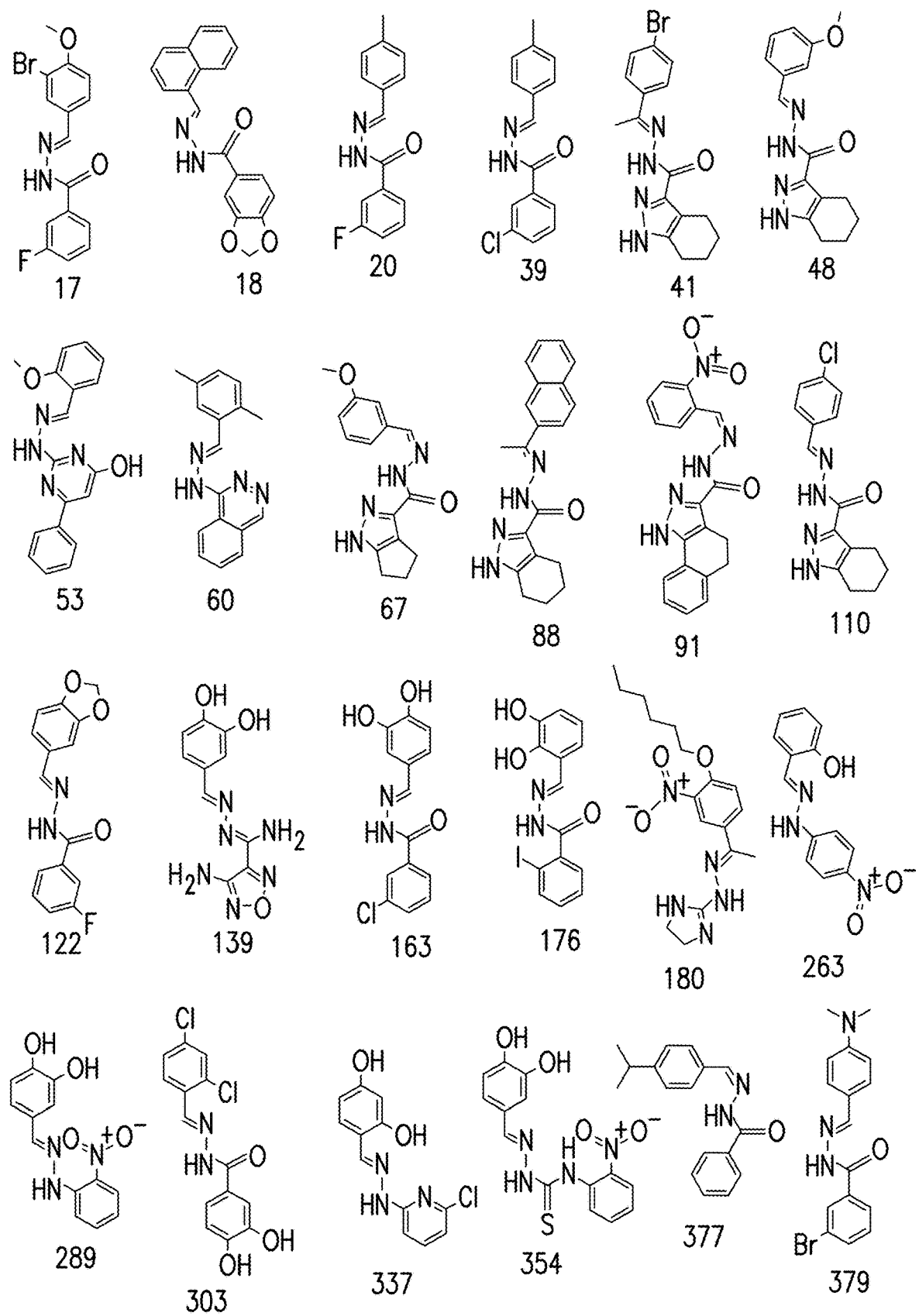
FIG. 15 depicts (FIG. 15A, FIG. 15B) structures of compounds formula (VII), and (FIG. 15C) a bar graph of bioactivities of those compounds, presented analogously to data of FIG. 9.
Figure 15B:
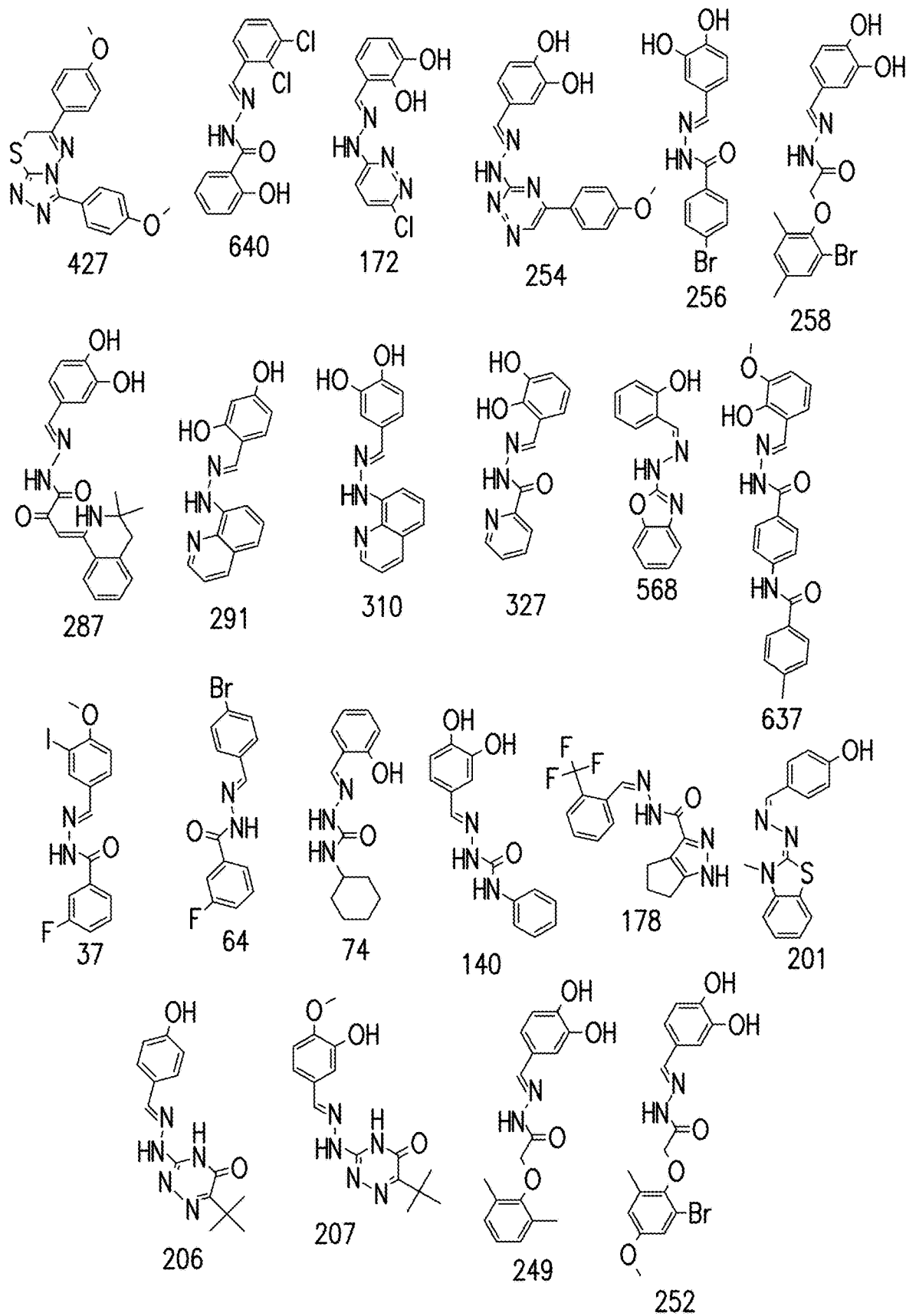
Figure 15C:
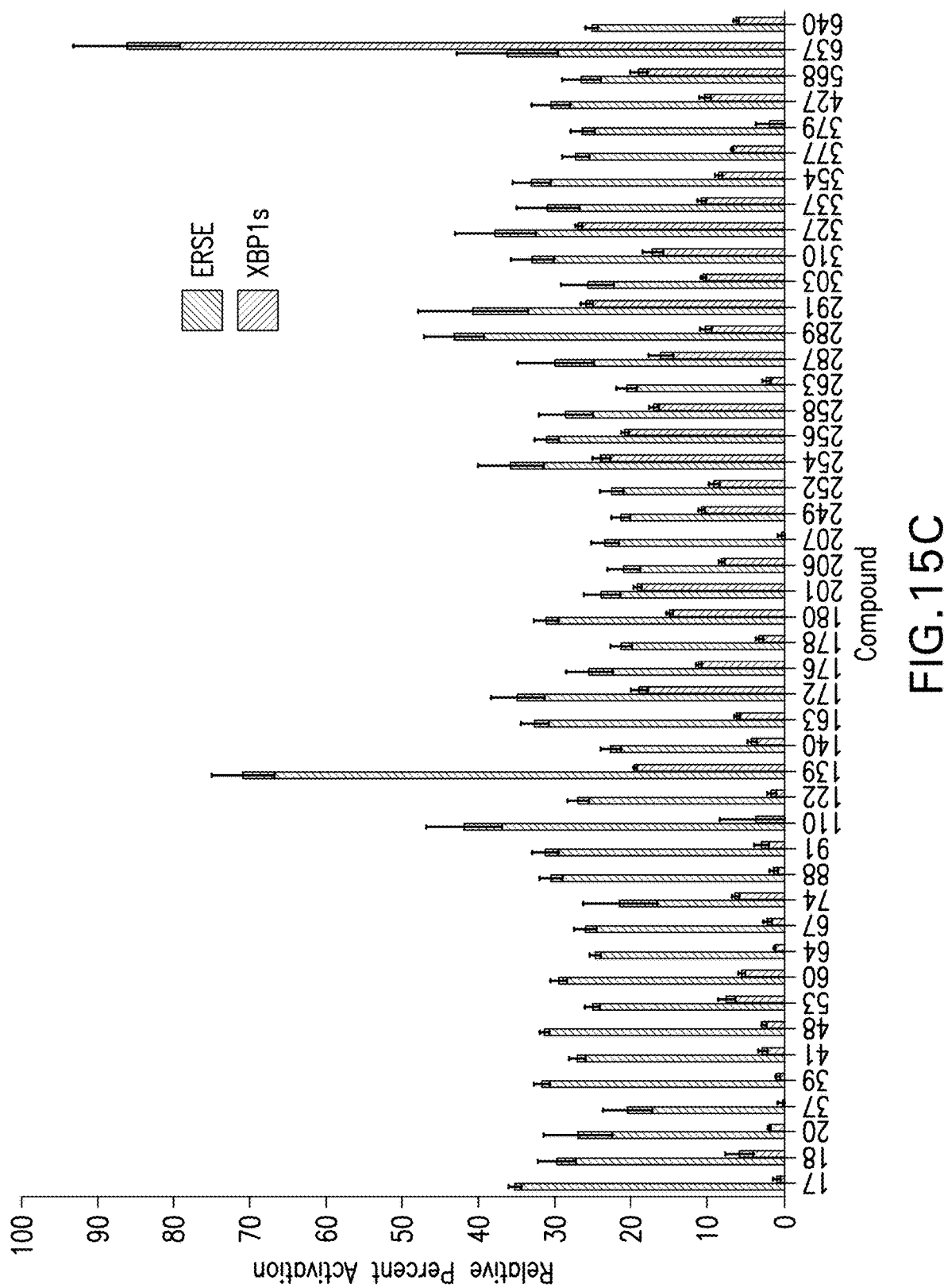
Figure 16A:
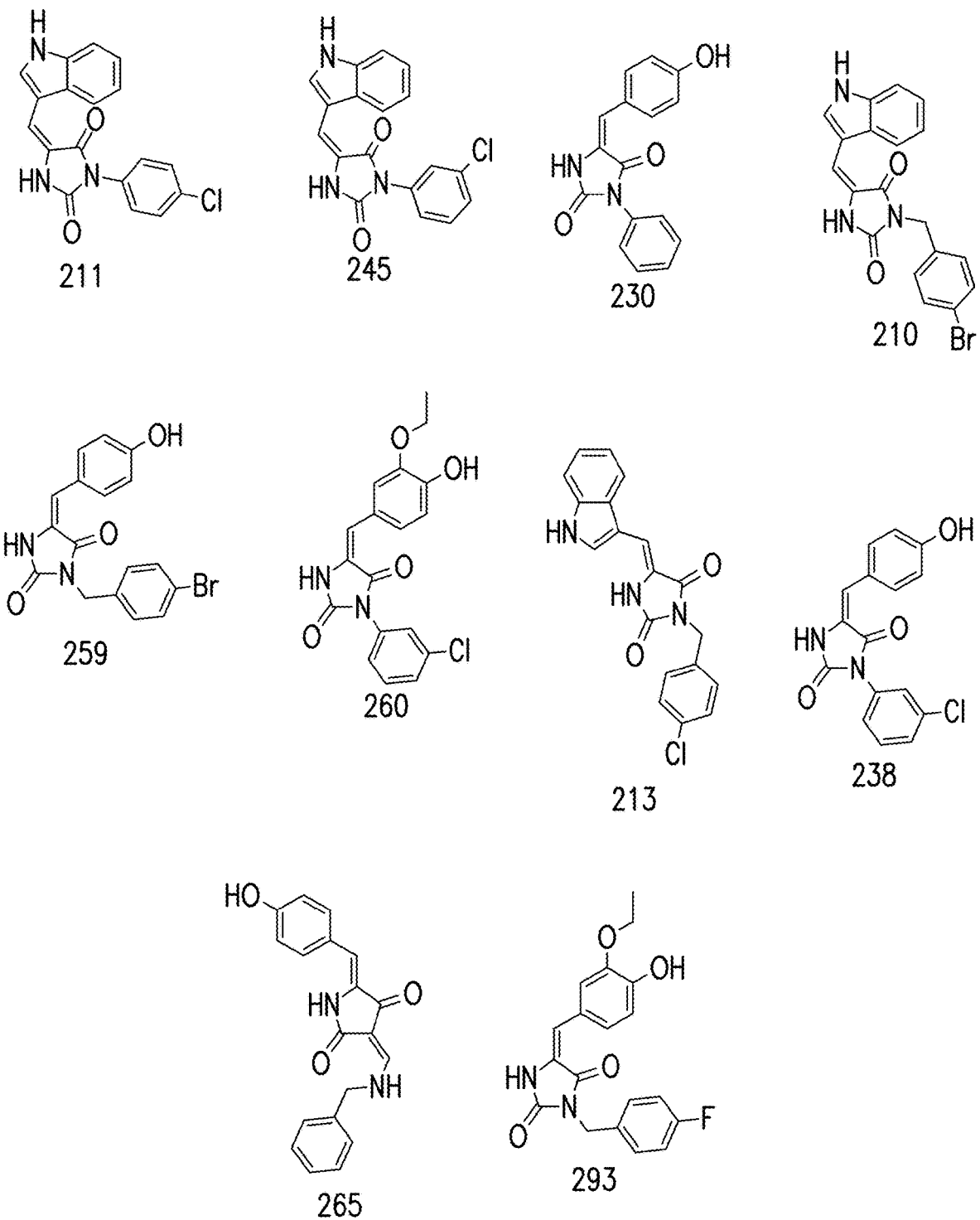
FIG. 16 depicts (FIG. 16A) structures of compounds of formula (VIII), and (FIG. 16B) a bar graph of bioactivities of those compounds, presented analogously to data of FIG. 9.
Figure 16B:
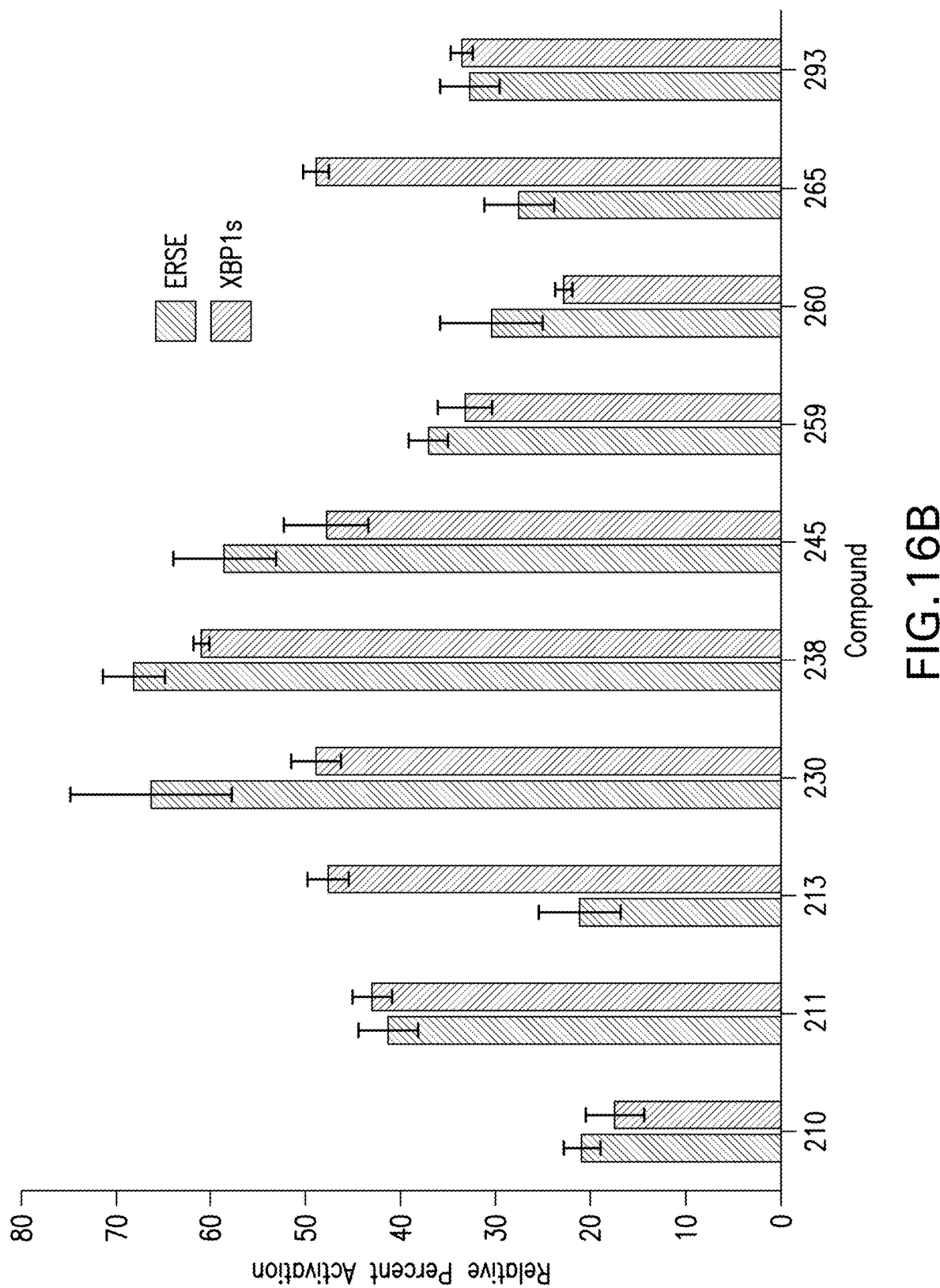
Figure 17B:
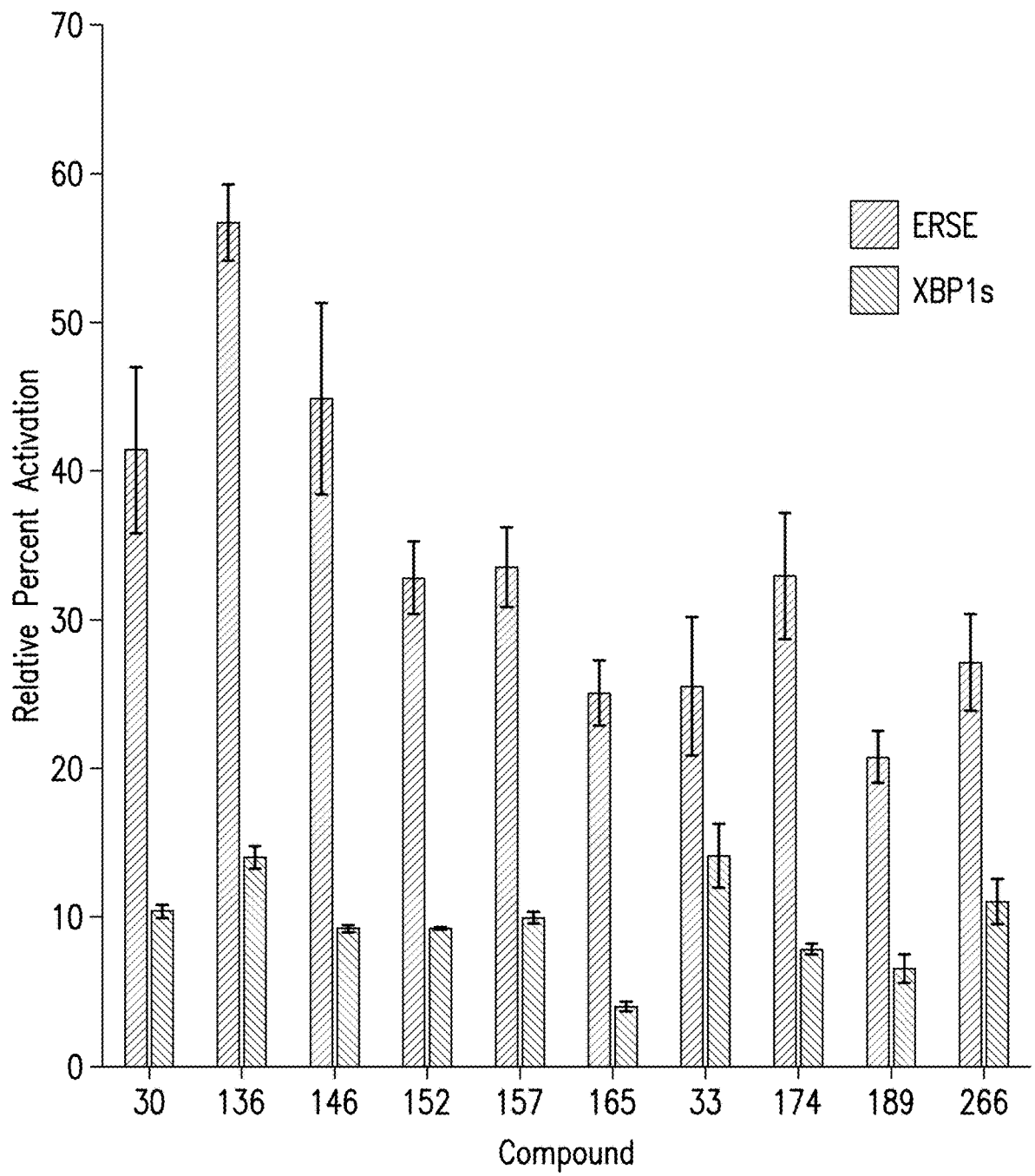
FIG. 17 depicts (FIG. 17A) structures of compounds of formula (IX), and (FIG. 17B) a bar graph of bioactivities of those compounds, presented analogously to data of FIG. 9.

We have begun structure-activity relationship studies on 263 as well. We first synthesized molecule 263 (RP28, FIG. 8a,c) which showed slightly increase reporter activity relative to 263 (FIG. 8b), likely due to partial hydrolysis of purchased 263 upon storage. We employed a synthetic strategy to synthesize compounds similar to 263 by refluxing the hydrazine with the desired aldehyde in methanol. We also synthesized a few derivatives of AA263 demonstrating that the ortho-hydroxy of 263 is essential for activity (RP31, FIG. 8a,b). We also modulated the ring with the ortho-hydroxy group by placing a p-methyl (RP29), which slightly decreased activity (FIG. 8a,b). Finally, we replaced the p-nitro group with a p-fluro (RP30), which also decreased activity (FIG. 8a,b).

Collectively, these preliminary structure activity relationships demonstrate the importance of the 2-amino-p-cresol substructure for activation of the ATF6 arm of the UPR by compound 147 and structurally related analogs and demonstrate that the presence of this substructure, while required, is not alone sufficient for ERSE-FLuc activation. These results show that there is a significant opportunity to continue to optimize the selectivity and potency of these small molecule ER proteostasis regulators through continued medicinal chemistry efforts.

Accordingly, the present invention provides, in various embodiments, a method of treatment of a protein misfolding disease in a patient afflicted therewith, comprising administering to the patient an effective amount of:

(1) a compound of formula (I)

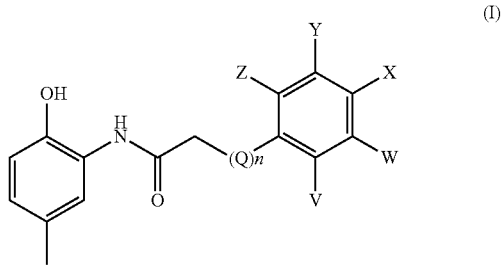

wherein Q is S, O, $CH_2$, CHF, or $CF_2$, n=1, 2, 3, or 4, when Q is $CH_2$, CHF, or CF2; n=1 when Q is S or O, and V, W, X, Y and Z are each independently hydrogen, halogen, alkyl, alkenyl, alkynyl, or alkoxy; or a pharmaceutically acceptable salt thereof;

or (2) a compound of formula (IIA)

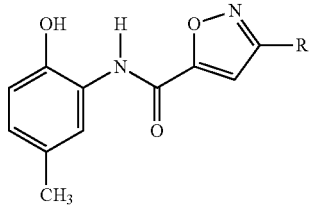

or (IIB)

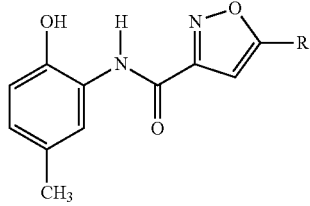

wherein R is alkyl, alkenyl, alkynyl, cycloalkyl, or cycloalkenyl, or is a 5- or 6-membered aryl or heteroaryl; wherein non-hydrogen R group can be unsubstituted or substituted; or a pharmaceutically acceptable salt thereof;

or (3) a compound of formula (IIIA)

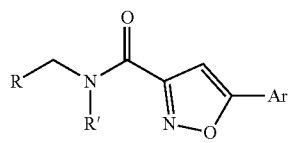

or of formula (IIIB)

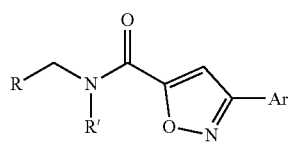

wherein R is unsubstituted or substituted alkyl, alkenyl, cycloalkyl, cycloalkyenyl, aryl, arylalkyl, heteroaryl, or heteroarylalkyl; Ar is aryl or heteroaryl, wherein any aryl or heteroaryl of Ar can be unsubstituted or substituted with halo, alkoxy, or hydroxyl; or R and R' together can form a substituted or unsubstituted 5- or 6-membered cycloalkyl or heterocycloalkyl; or a pharmaceutically acceptable salt thereof;

or (4) a compound of formula (IV)

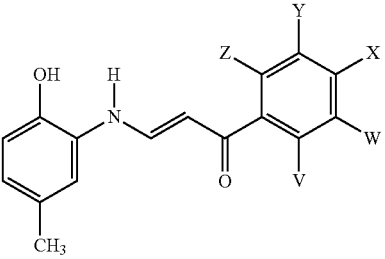

wherein V, W, X, Y, and Z are each independently H, halo, alkyl, alkenyl, or alkoxy; and wherein the ring bearing W can be a phenyl, or can be a 2-thienyl ring or an analogous 5 membered heteroaromatic ring wherein only groups V, W, and X are present; or a pharmaceutically acceptable salt thereof;

or (5) a compound of formula (V)

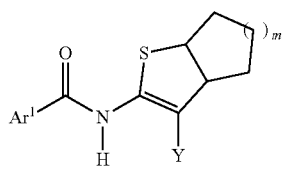

wherein m=1, 2, or 3; Y is cyano or carboxamido; and $Ar^1$ is any one of

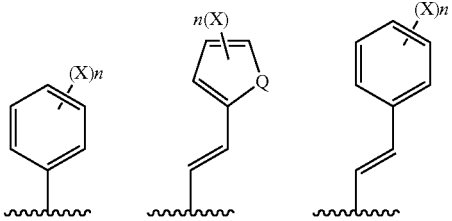

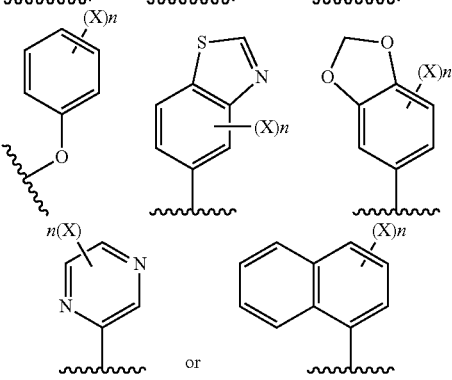

wherein Q is O or S, X is halo, alkyl, alkenyl, alkynyl, or alkoxy, and n=0, 1, 2, or 3; and a wavy line indicates a point of bonding or attachment; or a pharmaceutically acceptable salt thereof;

or, (6) a compound of formula (VIA)

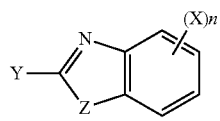
(VIA)

wherein each X is independently H, hydroxyl, halo, amine, nitro, (C1-C4)alkyl, (C2-C4) alkynyl, (C1-C4) alkyl ester, or (C1-C4)alkoxy, (C2-C4) alkenyl, (C1-C4) fluoroalkyl, benzoyl, mesyl; and n=0, 1, 2, or 3;

Z is NR, CR2 or S, each R is independently H, (C1-C4) alkyl, (C2-C4) alkenyl, (C2-C4)alkynyl, benzyl, (C1-C4) alkyl ester, (C1-C4)alkoxy, or (C1-C4) fluoroalkyl;

a wavy line indicates a point of bonding or attachment of Y, which is any one of,

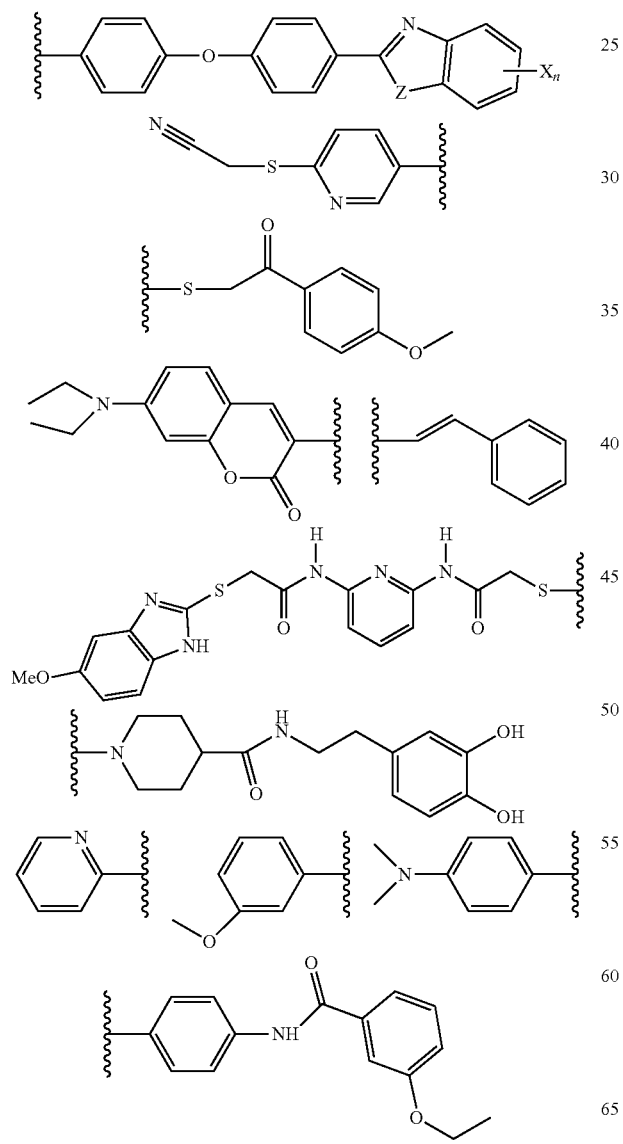

-continued

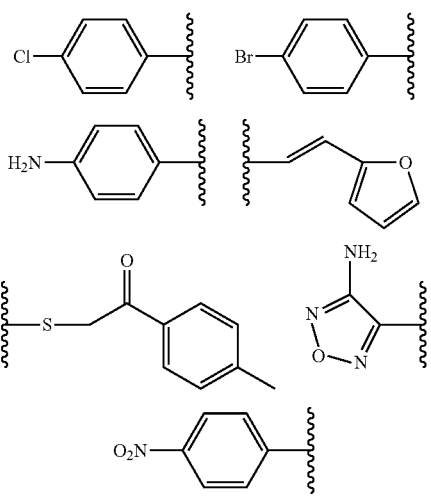

or of formula (VIB)

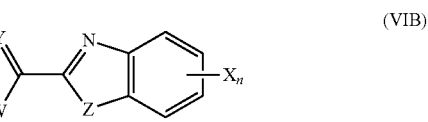
(VIB)

wherein each X is independently H, hydroxyl, halo, amine, nitro, (C1-C4)alkyl, (C2-C4) alkynyl, (C1-C4) alkyl ester, or (C1-C4)alkoxy, (C2-C4) alkenyl, (C1-C4) fluoroalkyl, mesyl; and n=0, 1, 2, or 3;

Z is NR, CR2 or S, each R is independently H, (C1-C4) alkyl, (C2-C4) alkenyl, (C2-C4)alkynyl, (C1-C4) alkyl ester, (C1-C4)alkoxy, or (C1-C4) fluoroalkyl;

a wavy line indicates a point of bonding or attachment of Y and W, which is any one of,

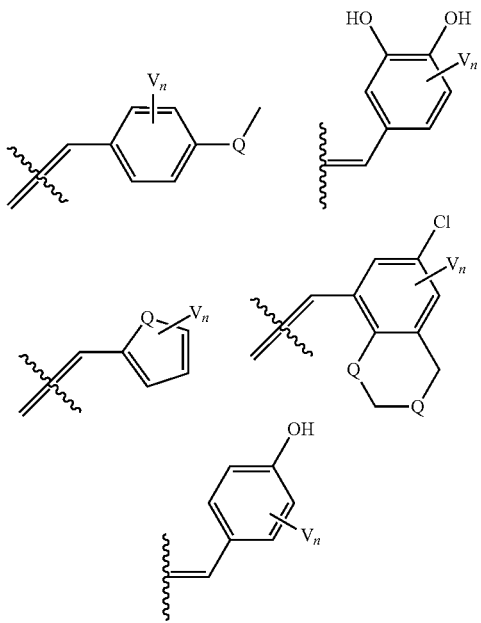

-continued

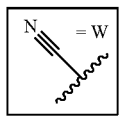

wherein Q is O or S; each V is independently H, hydroxyl, halo, amine, nitro, (C1-C4)alkyl, (C2-C4)alkynyl, (C1-C4) alkyl ester, or (C1-C4)alkoxy, (C2-C4) alkenyl, (C1-C4) fluoroalkyl, mesyl; and n=0, 1, 2, or 3, or a pharmaceutically acceptable salt thereof;
or
or of formula (VIC)

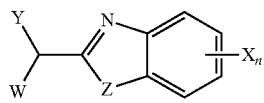

(VIC)

wherein each X is independently H, hydroxyl, halo, amine, nitro, (C1-C4)alkyl, (C2-C4) alkynyl, (C1-C4) alkyl ester, or (C1-C4)alkoxy, (C2-C4) alkenyl, (C1-C4) fluoroalkyl, mesyl; and n=0, 1, 2, or 3;

Z is NR, CR2 or S, each R is independently H, (C1-C4) alkyl, (C2-C4) alkenyl, (C2-C4)alkynyl, (C1-C4) alkyl ester, (C1-C4)alkoxy, or (C1-C4) fluoroalkyl;

a wavy line indicates a point of bonding or attachment of Y and W, which is any one of,

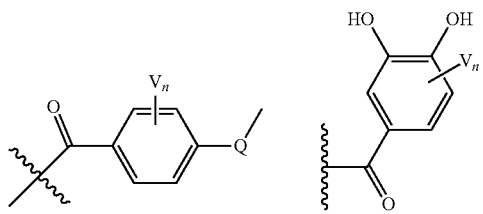

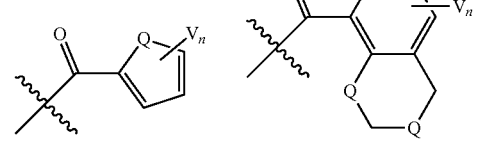

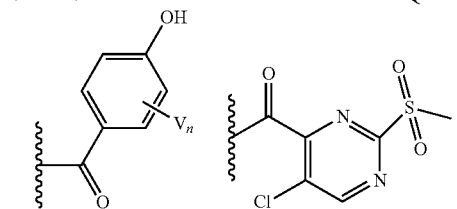

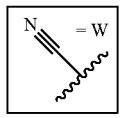

wherein Q is O or S; each V is independently H, hydroxyl, halo, amine, nitro, (C1-C4)alkyl, (C2-C4)alkynyl, (C1-C4) alkyl ester, or (C1-C4)alkoxy, (C2-C4) alkenyl, (C1-C4) fluoroalkyl, mesyl; and n=0, 1, 2, or 3, or a pharmaceutically acceptable salt thereof;

or
(7) a compound of formula (VIIA)

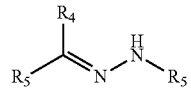

(VIIA)

or a compound of formula (VIIB)

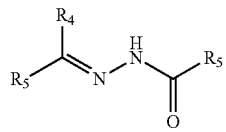

(VIIB)

or a compound of formula (VIIC)

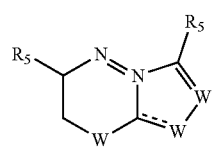

(VIIC)

wherein Q is O or S; W=C,N,S,O; $R^4$ is H, OH, halo or (C1-C4)alkyl, or (C1-C4) alkoxy; X is halo, nitro, (C1-C4) alkyl, (C2-C4)alkynyl, (C1-C4) alkyl ester, or (C1-C4) alkoxy, (C2-C4) alkenyl, (C1-C4) fluoroalkyl; m=1, 2, or 3, and n=0, 1, 2, or 3;

$R^5$ is independently at each occurrence any one of:

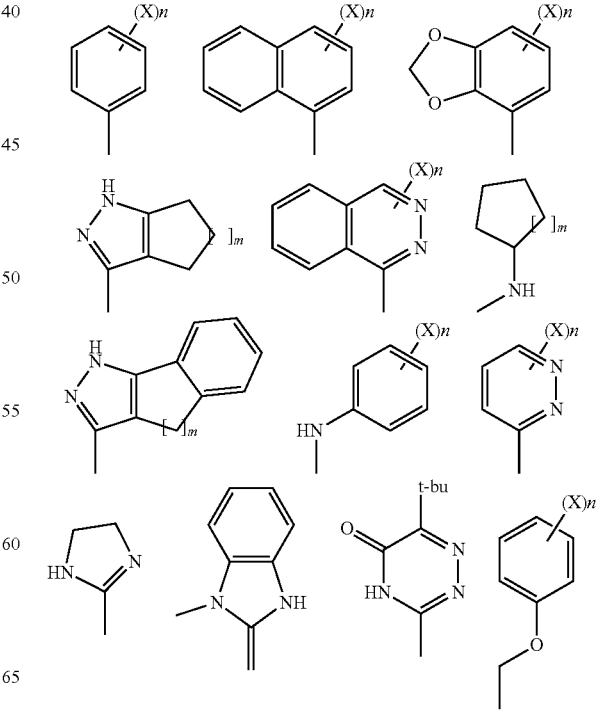

-continued

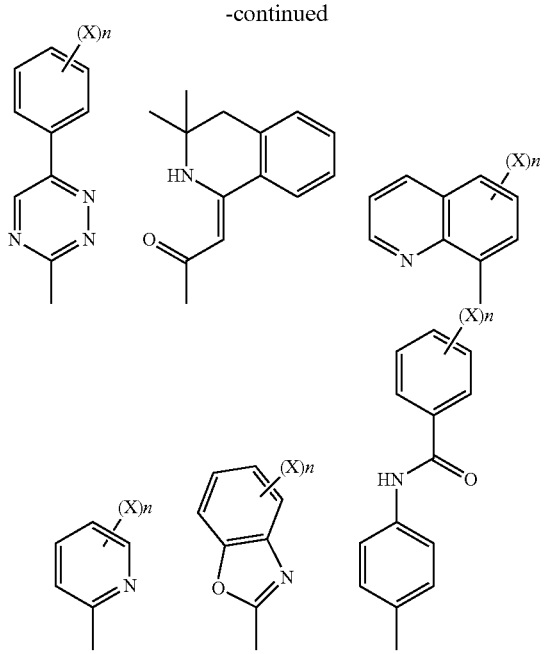

or a pharmaceutically acceptable salt thereof;
or
(8) a compound of formula (VIII)

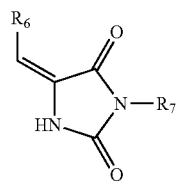
(VIII)

wherein R⁶ is any one of

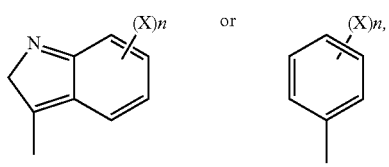

R⁷ is

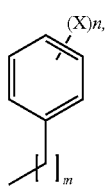

X is H, halo, hydroxyl, nitro, (C1-C4)alkyl, (C2-C4) alkynyl, (C1-C4) alkyl ester, (C1-C4)alkoxy, (C2-C4) alkenyl, or (C1-C4) fluoroalkyl; m=0, 1, or 2, and n=0, 1, 2, or 3; or a pharmaceutically acceptable salt thereof;

or
(9) a compound of formula (IX)

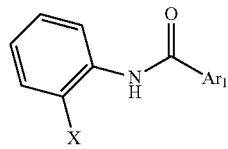
(IX)

wherein X is hydroxyl or amine, and Ar₁ is any one of:

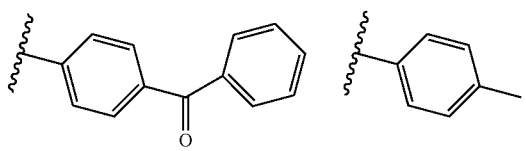

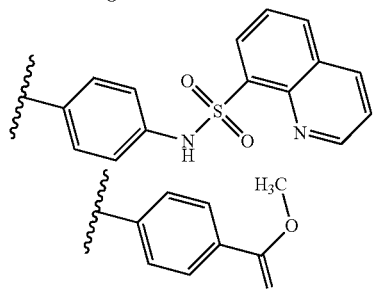

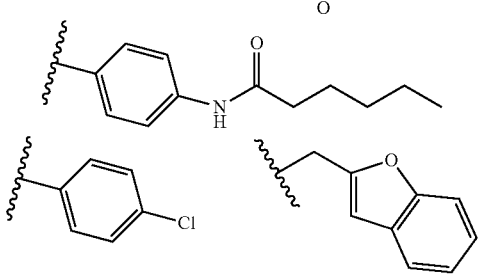

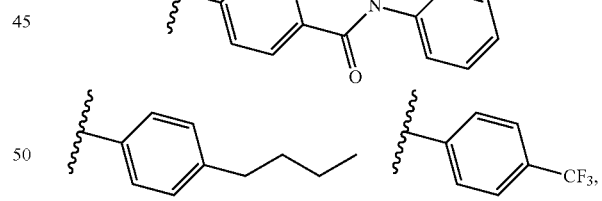

or a pharmaceutically acceptable salt thereof.

In various embodiments, for practice of a method of the invention the compound can be any one of those shown in FIGS. 7-17, according to its generic formula (I) through (IX) as defined herein.

In various embodiments, the protein misfolding disease can comprise a gain-of-proteotoxicity protein aggregation disease. For example, the protein aggregation disease can comprise an amyloid disease including Alzheimer's disease, light chain amyloidosis, or a transthyretin amyloidosis, or retinitis pigmentosa associated with mutant rhodopsin aggregation, or antitrypsin associated liver cancer.

In other embodiments, the protein misfolding disease can comprise a loss-of-function protein misfolding disease. For example, the protein misfolding disease can comprise a lysosomal storage disease, Cystic Fibrosis, antitrypsin associated emphysema or osteogenesis imperfect or related collegenopathies.

In further embodiments, the protein misfolding disease treatable by a method of the invention can be associated with secretory pathway protein homeostasis stresses, including diabetes, metabolic disorders, eye disease, and cardiovascular disease.

In certain embodiments, the disease is ameliorated by selectively activating the activating transcription factor 6 (ATF6) arm of the unfolded protein response (UPR) in the endoplasmic reticulum and/or downstream compartments of a cell in the patient.

In additional embodiments, the invention provides a method of preferentially activating the activating transcription factor 6 (ATF6) arm of the unfolded protein response (UPR) in the endoplasmic reticulum of a cell, comprising contacting the cell with an effective amount or concentration of a compound of
(1) a compound of formula (I)

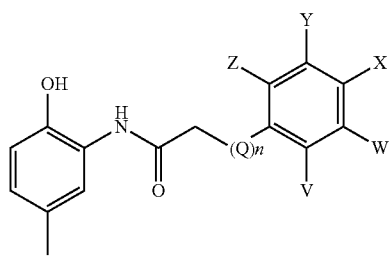

(I)

wherein Q is S, O, CH$_2$, CHF, or CF$_2$, n=1, 2, 3, or 4, when Q is CH$_2$, CHF, or CF$_2$; n=1 when Q is S or O, and V, W, X, Y and Z are each independently hydrogen, halogen, alkyl, alkenyl, alkynyl, or alkoxy; or a pharmaceutically acceptable salt thereof;
or
(2) a compound of formula (IIA)

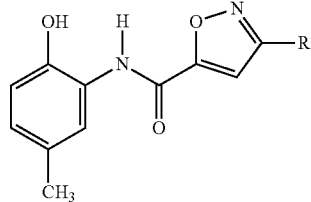

(IIA)

or (IIB)

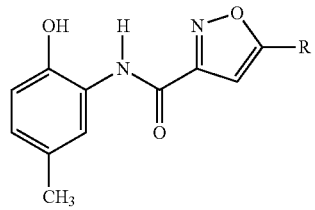

(IIB)

wherein R alkyl, alkenyl, alkynyl, cycloalkyl, or cycloalkenyl, or is a 5- or 6-membered aryl or heteroaryl; wherein non-hydrogen R group can be unsubstituted or substituted; or a pharmaceutically acceptable salt thereof;
or
(3) a compound of formula (IIIA)

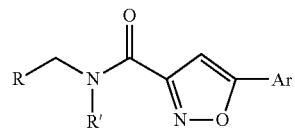

(IIIA)

or of formula (IIIB)

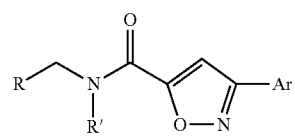

(IIIB)

wherein R is unsubstituted or substituted alkyl, alkenyl, cycloalkyl, cycloalkyenyl, aryl, arylalkyl, heteroaryl, or heteroarylalkyl; Ar is aryl or heteroaryl, wherein any aryl or heteroaryl of Ar can be unsubstituted or substituted with halo, alkoxy, or hydroxyl; or R and R' together can form a substituted or unsubstituted 5- or 6-membered cycloalkyl or heterocycloalkyl; or a pharmaceutically acceptable salt thereof;
or
(4) a compound of formula (IV)

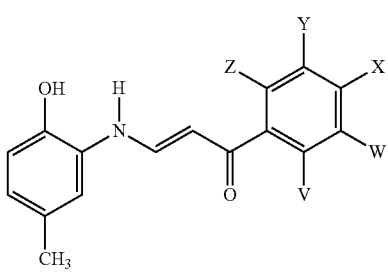

(IV)

wherein V, W, X, Y, and Z are each independently H, halo, alkyl, alkenyl, or alkoxy; and wherein the ring bearing W can be a phenyl, or can be a 2-thienyl ring or an analogous 5 membered heteroaromatic ring wherein only groups V, W, and X are present; or a pharmaceutically acceptable salt thereof;
or
(5) a compound of formula (V)

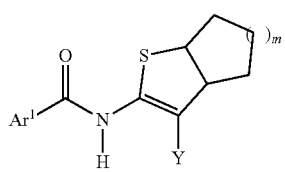

(V)

wherein m=1, 2, or 3; Y is cyano or carboxamido; and Ar¹ is any one of

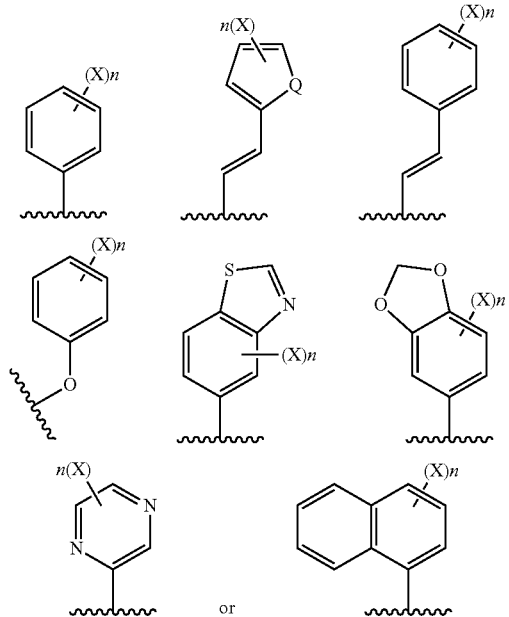

wherein Q is O or S, X is halo, alkyl, alkenyl, alkynyl, or alkoxy, and n=0, 1, 2, or 3; and a wavy line indicates a point of bonding or attachment; or a pharmaceutically acceptable salt thereof;

or, (6) a compound of formula (VIA)

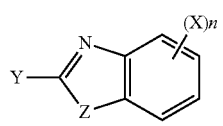

(VIA)

wherein each X is independently H, hydroxyl, halo, amine, nitro, (C1-C4)alkyl, (C2-C4) alkynyl, (C1-C4) alkyl ester, or (C1-C4)alkoxy, (C2-C4) alkenyl, (C1-C4) fluoroalkyl, benzoyl, mesyl; and n=0, 1, 2, or 3;

Z is NR, CR2 or S, each R is independently H, (C1-C4) alkyl, (C2-C4) alkenyl, (C2-C4)alkynyl, benzyl, (C1-C4) alkyl ester, (C1-C4)alkoxy, or (C1-C4) fluoroalkyl;

a wavy line indicates a point of bonding or attachment of Y, which is any one of,

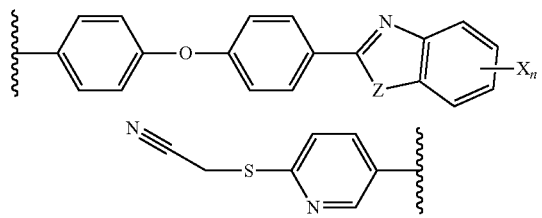

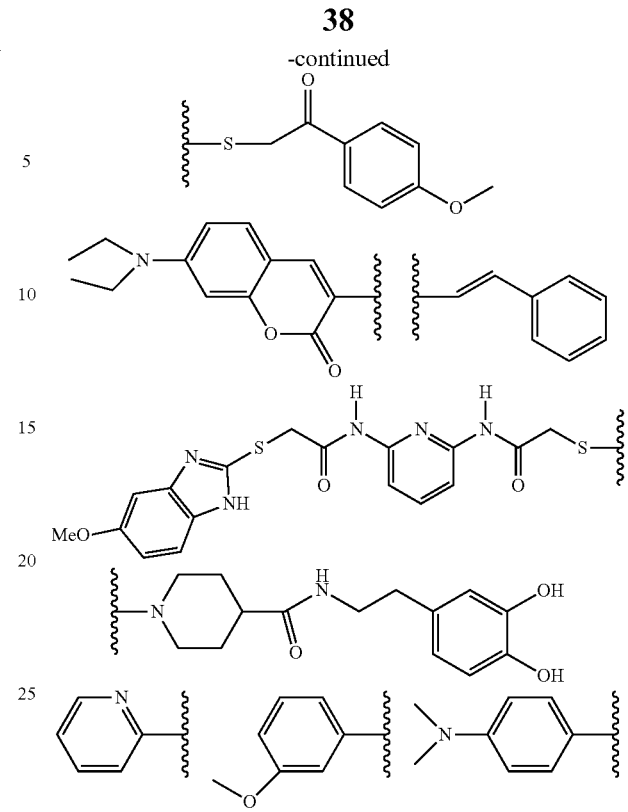

or of formula (VIB)

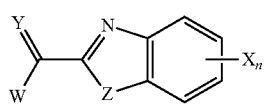

(VIB)

wherein each X is independently H, hydroxyl, halo, amine, nitro, (C1-C4)alkyl, (C2-C4) alkynyl, (C1-C4) alkyl ester, or (C1-C4)alkoxy, (C2-C4) alkenyl, (C1-C4) fluoroalkyl, mesyl; and n=0, 1, 2, or 3;

Z is NR, CR2 or S, each R is independently H, (C1-C4) alkyl, (C2-C4) alkenyl, (C2-C4)alkynyl, (C1-C4) alkyl ester, (C1-C4)alkoxy, or (C1-C4) fluoroalkyl;

a wavy line indicates a point of bonding or attachment of Y and W, which is any one of,

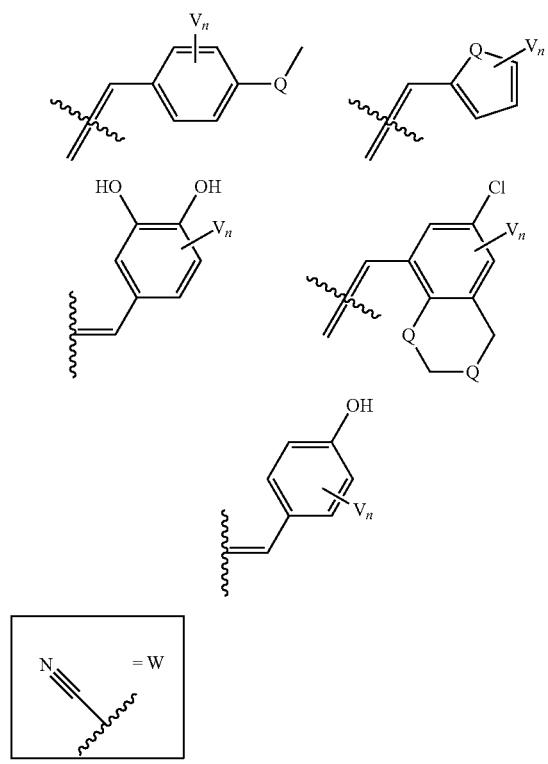

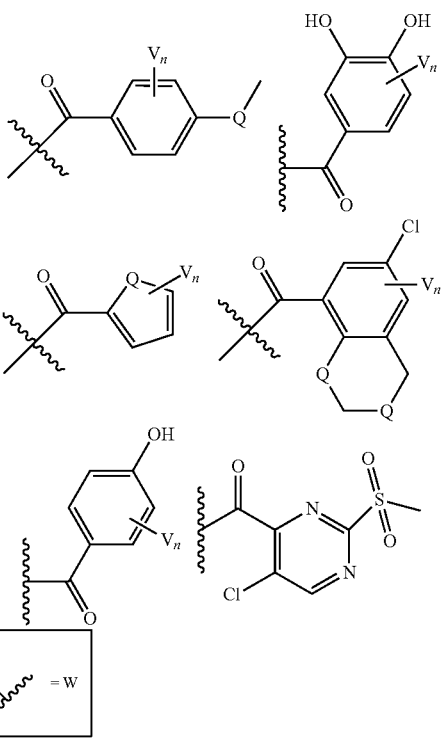

wherein Q is O or S; each V is independently H, hydroxyl, halo, amine, nitro, (C1-C4)alkyl, (C2-C4)alkynyl, (C1-C4) alkyl ester, or (C1-C4)alkoxy, (C2-C4) alkenyl, (C1-C4) fluoroalkyl, mesyl; and n=0, 1, 2, or 3, or a pharmaceutically acceptable salt thereof;

or or of formula (VIC)

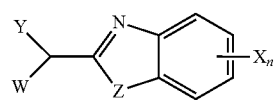 (VIC)

wherein each X is independently H, hydroxyl, halo, amine, nitro, (C1-C4)alkyl, (C2-C4) alkynyl, (C1-C4) alkyl ester, or (C1-C4)alkoxy, (C2-C4) alkenyl, (C1-C4) fluoroalkyl, mesyl; and n=0, 1, 2, or 3;

Z is NR, CR2 or S, each R is independently H, (C1-C4) alkyl, (C2-C4) alkenyl, (C2-C4)alkynyl, (C1-C4) alkyl ester, (C1-C4)alkoxy, or (C1-C4) fluoroalkyl;

a wavy line indicates a point of bonding or attachment of Y and W, which is any one of, wherein Q is O or S; each V is independently H, hydroxyl, halo, amine, nitro, (C1-C4)alkyl, (C2-C4)alkynyl, (C1-C4) alkyl ester, or (C1-C4)alkoxy, (C2-C4) alkenyl, (C1-C4) fluoroalkyl, mesyl; and n=0, 1, 2, or 3, or a pharmaceutically acceptable salt thereof;

or (7) a compound of formula (VIIA)

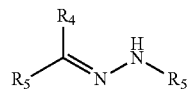 (VIIA)

or a compound of formula (VIIB)

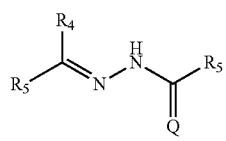 (VIIB)

or a compound of formula (VIIC)

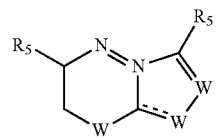 (VIIC)

wherein Q is O or S; W=C,N,S,O; $R^4$ is H, OH, halo or (C1-C4)alkyl, or (C1-C4) alkoxy; X is halo, nitro, (C1-C4)

alkyl, (C2-C4)alkynyl, (C1-C4) alkyl ester, or (C1-C4) alkoxy, (C2-C4) alkenyl, (C1-C4) fluoroalkyl; m=1, 2, or 3, and n=0, 1, 2, or 3;

R⁵ is independently at each occurrence any one of:

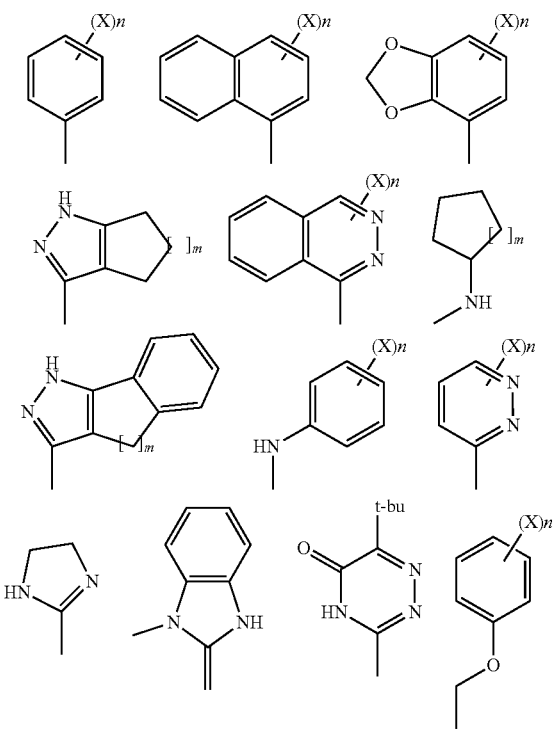

or a pharmaceutically acceptable salt thereof;

or (8) a compound of formula (VIII)

(VIII)

wherein R⁶ is any one of

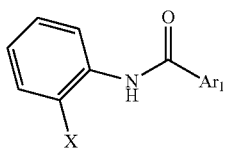

R⁷ is

X is H, halo, hydroxyl, nitro, (C1-C4)alkyl, (C2-C4) alkynyl, (C1-C4) alkyl ester, (C1-C4)alkoxy, (C2-C4) alkenyl, or (C1-C4) fluoroalkyl; m=0, 1, or 2, and n=0, 1, 2, or 3; or a pharmaceutically acceptable salt thereof;

or (9) a compound of formula (IX)

(IX)

wherein X is hydroxyl or amine, and Ar, is any one of:

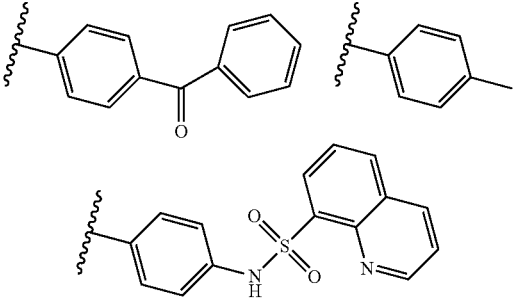

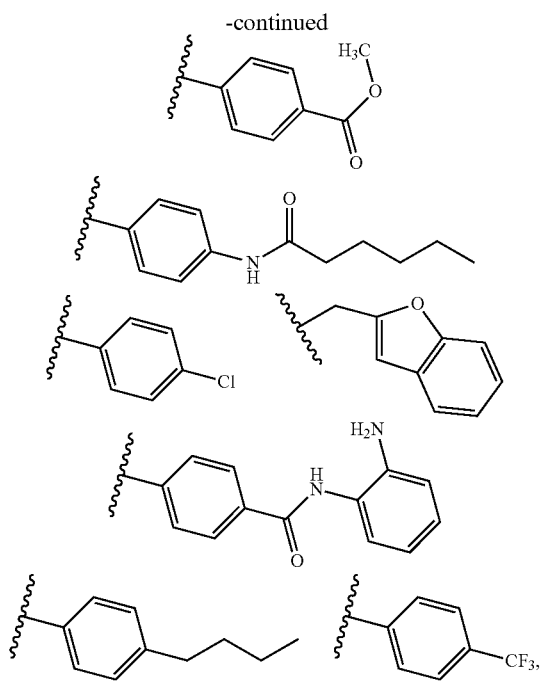

or a pharmaceutically acceptable salt thereof.

In various embodiments, for practice of a method of the invention the compound can be any one of those shown in FIGS. 7-17, according to its generic formula (I) through (IX) as defined herein.

For instance, if it is determined that a disease is ameliorated by activating the activating transcription factor 6 (ATF6) arm of the unfolded protein response (UPR) in the endoplasmic reticulum and/or a downstream compartment of a cell in an animal or a human, by administering an effective amount of the compound of formula (I)-formula (IX) to the patient and observing if the administration produces a therapeutic effect in the patient, a compound can be identified as suitable for treatment of the disease in a patient.

Definitions

The term "disease" or "disorder" or "malcondition" are used interchangeably, and are used to refer to diseases or conditions wherein preferentially activating the activating transcription factor 6 (ATF6) arm of the unfolded protein response (UPR) in the endoplasmic reticulum of a cell plays a role in the biochemical mechanisms involved in the disease or malcondition or symptom(s) thereof such that a therapeutically beneficial effect can be achieved by acting on preferentially activating the activating transcription factor 6 (ATF6) arm of the unfolded protein response (UPR) in the endoplasmic reticulum of a cell, e.g. with an effective amount or concentration of a synthetic ligand of the invention.

The expression "effective amount", when used to describe therapy to an individual suffering from a disorder, refers to the quantity or concentration of a compound of the invention that is effective to inhibit or otherwise act by preferentially activating the activating transcription factor 6 (ATF6) arm of the unfolded protein response (UPR) in the endoplasmic reticulum of a cell in the individual's tissues, wherein such inhibition or other action occurs to an extent sufficient to produce a beneficial therapeutic effect.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents, or provides prophylaxis for, the disorder or condition. In particular, a "therapeutically effective amount" refers to an amount that is effective, at dosages and for periods of time necessary, to achieve the desired therapeutic result. A therapeutically effective amount is also one in which any toxic or detrimental effects of compounds of the invention are outweighed by the therapeutically beneficial effects.

All single enantiomer, diastereomeric, and racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated for practice of methods of the invention herein.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite and is limited by ordinary understanding.

In general, "substituted" refers to an organic group as defined herein in which one or more bonds to a hydrogen atom contained therein are replaced by one or more bonds to a non-hydrogen atom such as, but not limited to, a halogen (e.g., F, Cl, Br, or I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, nitroso groups, N-oxides, hydrazides, azides, and enamines; and other heteroatoms in various other groups. Non-limiting examples of substituents that can be bonded to a substituted carbon (or other) atom include F, Cl, Br, I, OR, CN, NO, $NO_2$, $ONO_2$, azido, $CF_3$, $OCF_3$, R, O (oxo), S (thiono), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, C(S)$N(R)_2$, $(CH_2)_{0-2}N(R)C(O)R$, $(CH_2)_2N(R)N(R)_2$, N(R)N(R)C(O)R, N(R)N(R)C(O)OR, $N(R)N(R)CON(R)_2$, N(R)$SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, C(=NH)$N(R)_2$, C(O)N(OR)R, or C(=NOR)R wherein R can be hydrogen or a carbon-based moiety, and wherein the carbon-based moiety can itself be further substituted; for example, R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl can be further independently mono- or multi-substituted with the substituent, or with some or all of the above-listed functional groups, or with other functional groups; or wherein two R groups bonded to a nitrogen atom or to adjacent nitrogen atoms can together with the nitrogen atom or atoms form a heterocyclyl, which can be further mono- or independently multi-substituted with the substituent, or with some or all of the above-listed functional groups, or with other functional groups.

Alkyl groups include straight chain and branched carbon-based groups having from 1 to about 20 carbon atoms, and typically from 1 to 12 carbons or, in some embodiments, from 1 to 8 carbon atoms, or from 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the substituent groups listed above, for example, amino, hydroxy, cyano, carboxy, nitro, thio, alkoxy, and halogen groups.

Cycloalkyl groups are groups containing one or more carbocyclic ring including, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others. Exemplary alkenyl groups include, but are not limited to, a straight or branched group of 2-6 or 3-4 carbon atoms, referred to herein as C2-.alkenyl, and C$_{3-4}$alkenyl, respectively. Exemplary alkenyl groups include, but are not limited to, vinyl, allyl, butenyl, pentenyl, etc.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

Aryl groups are cyclic aromatic hydrocarbons that do not contain heteroatoms in the ring. An aromatic compound, as is well-known in the art, is a multiply-unsaturated cyclic system that contains 4n+2 π electrons where n is an integer. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclyl groups or the term "heterocyclyl" includes aromatic and non-aromatic ring compounds containing 3 or more ring members, of which one or more ring atom is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members.

Heteroaryl groups are heterocyclic aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure, which is a multiply-unsaturated cyclic system that contains 4n+2 π electrons wherein n is an integer.

The term "alkoxy" or "alkoxyl" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by the same or differing halogen atoms, such as fluorine and/or chlorine atoms. Examples of haloalkyl include trifluoromethyl, 1,1-dichloroethyl, 1,2-dichloroethyl, 1,3-dibromo-3,3-difluoropropyl, perfluorobutyl, and the like.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

A "pharmaceutically acceptable" or "pharmacologically acceptable" salt is a salt formed from an ion that has been approved for human consumption and is generally non-toxic, such as a chloride salt or a sodium salt.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation. The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used.

It is within ordinary skill to evaluate any compound disclosed and claimed herein for effectiveness in preferential activation of the activating transcription factor 6 (ATF6) arm of the unfolded protein response (UPR) in the endoplasmic reticulum of a cell and in the various assays using the procedures described above or found in the scientific literature. Accordingly, the person of ordinary skill can prepare and evaluate any of the claimed compounds without undue experimentation.

Any compound found to be an effective for preferential activation of the activating transcription factor 6 (ATF6) arm of the unfolded protein response (UPR) in the endoplasmic reticulum of a cell can likewise be tested in animal models and in human clinical studies using the skill and experience of the investigator to guide the selection of dosages and treatment regimens.

EXAMPLES

Plasmids

ERSE-Firefly luciferase reporter was cloned into a vector suitable for mammalian cell selection by transferring ERSE-FLuc from ERSE-FLuc.pGL3[1] into a promotorless pcDNA3.1 vector using Xba1 and Not1 restriction sites to create ERSE.FLuc.pcDNA3.1. XBP1s-*Renilla* luciferase was generated from a known XBP1s-GFP reporter. GFP was exchanged for *Renilla* luciferase by the Polymerase Incomplete Primer Extension (PIPE) method[3] using the following primers: vector, XBP1s-GFP.pCEFL, CTGAAGAACGAGCAGTAAGTGAGCAAGGGCGAG-GAG (SEQ ID NO: 1) and CGTACACCTTGGAAGCA-GATCTTGAATCTGAAGAGTCAATACC (SEQ ID NO: 2); gene, CMV-*Renilla*, CGGTATTGACTCTTCAGATT-CAAGATCTGCTTCCAAGGTGTACG (SEQ ID NO: 3) and CTCCTCGCCCTTGCTCACT-TACTGCTCGTTCTTCAG (SEQ ID NO: 4) to create XBP1s.RLuc.pCEFL. TTR point mutations were incorporated into the FLAG$_2$.TTR.pcDNA3.1 vector through site-directed mutagenesis[4].

Compounds

All specific compounds discussed herein were obtained from commercial vendors and were used without further purification by dissolving in sterile dimethyl sulfoxide (DMSO). The identity of screening compounds was confirmed by LCMS analysis and all compounds were shown to be >90% pure. Compounds described herein, including the specific examples and the compounds of formulas (I) through (IX) as recited in the Disclosure and the Claims can be prepared using procedures described herein and in the literature, in conjunction with the ordinary skill and knowledge of the skilled practitioner in the art of organic synthesis. FIG. 7 shows the preparation of analogs of compound 147.

Cell Culture and Transfections

HEK293T-Rex, HEK293T, HEK293$^{DAX}$, HepG2, ATF6$^{+/+}$ MEFs and ATF6$^{-/-}$ MEFs were cultured in High-Glucose Dulbecco's Modified Eagle's Medium (DMEM) supplemented with glutamine, penicillin/streptomycin and 10% fetal bovine serum. HEK293 cells containing the ERSE-FLuc or XBP1s-RLuc reporters were created by transfection with ERSE.FLuc.pcDNA3.1 or XBP1s.RLuc.pCEFL by calcium phosphate followed by culturing in geneticin sulfate (G-418, 500 μg/mL, ERSE) or puromycin (20 μg/mL, XPB1s). Creation and maintenance of HEK293$^{DAX}$ cells has been described previously[4]. U2OS cells stably expressing GFP-ATF6 were purchased from Thermo Scientific (084_01) and cultured with 500 μg/mL G418 (Roche) to maintain expression of GFP-ATF6. Transient transfections of $^{FT}$TTR variants were performed with Lipofectamine 3000 (Life Technologies). ALMC-2 and KAS-6/1 plasma cells were cultured in Iscove's Modified Dulbecco's Medium (IMDM) GlutaMAX (Life Technologies) supplemented with penicillin/streptomycin, 5% fetal bovine serum and 2 ng/mL interleukin-6 (IL-6). All cells were cultured under typical tissue culture conditions (37° C., 5% $CO_2$).

Reporter Assays

96-Well, HEK293$^{DAX}$ Experiments and SIP Inhibition

HEK293T-Rex cells incorporating the ERSE-FLuc reporter and HEK293$^{DAX}$ cells were plated approximately 20,000 cells/well in flat-bottomed, black 96-well assay plates (Costar, Corning, Inc.) overnight prior to compound administration. Cells were treated with compounds as described for 12-18 h then the plates were equilibrated to room temperature and 50 μL of SteadyLite (PerkinElmer) was added to each well. Luminescence activity was measured in a Safire II microplate reader with a 1000 ms integration time.

384-Well, Tg and Tm Dose Response in Reporter Cells

HEK293T-Rex cells incorporating either the ERSE-FLuc or XBP1s-RLuc reporters were plated 20 μL/well from 250,000 cells/mL in white 384-well plates (Corning). Cell plates were centrifuged for 1 min at 1000 rpm, then incubated at 37° C. overnight. The following day cells were treated as described with various concentrations of Thapsigargin or Tunicamycin, incubated for a further 18 h at 37° C., equilibrated to room temperature, then 20 μL of Steady-Lite (PerkinElmer) or *Renilla*-Glo (Promega) were added to each well. Luminescence activity was measured 10 minutes after reagent addition with an EnVision Multilabel Reader (PerkinElmer) using a 100 ms integration time.

1536-Well, High-Throughput Screening

HEK293T-Rex cells incorporating either the ERSE-FLuc or XBP1s-RLuc reporters were collected by trypsinization and resuspended at a density of 500,000 cells per mL. The assay was started by dispensing 5 μL of cell suspension into each well of white, solid-bottom 1536-well plates using a flying reagent dispenser (FRD) and placed into an online incubator 3 h. Cells were then treated with 34 nL/well of either test compounds to give final concentrations of 6.8 μM, DMSO (Low control, final concentration 0.68%, 0% activation) or 37 μM of Delta-7 thapsigargin (High control, final concentration 500 nM, 100% activation). Plates were incubated for 18 h at 37° C., removed from the incubator and equilibrated to room temperature for 10 min. Luciferase activity was detected by addition of 5 μL of ONE-Glo reagent (Promega) to each well. After a 10 min incubation time, light emission was measured with the ViewLux reader (PerkinElmer). The percent activation of each test compound was calculated as follows: % Activation=100*(Test Compound−Median Low Control)/(Median High Control ~Median Low Control).

Cytotoxicity Assays

HEK293T-Rex cells incorporating either the ERSE-FLuc or XBP1s-RLuc reporters were collected by trypsinization and resuspended at a density of 500,000 cells per mL. The assay was started by dispensing 5 μL of cell suspension into each well of white, solid-bottom 1536-well plates using a flying reagent dispenser (FRD) and placed into an online incubator 3 h. Cells were then treated for 48 h with various concentrations of proteostasis regulator, DMSO (0% toxicity) or 340 μM Doxorubicin as a positive control (100% toxicity). After 48 h of incubation, toxicity was determined using an ATP detection method (CellTiter Glo, Promega).

HepG2 cells were plated at 5,000 cells/well in a translucent, flat-bottomed 96 well plate, and treated for 48 hr with vehicle, 10 μM Tg or 10 μM ER proteostasis regulator. ALMC-2 or KAS-6/1 cells were plated at 33,000 cells/well in 96-well plates then treated with proteostasis regulators for 16 h as described. Cell metabolic activity was measured using the CellTiter-Glo assay (Promega), which reports on intracellular ATP concentration. CellTiter-Glo reagent was added to cell culture media at a 1:1 ratio and incubated for 2 minutes on an orbital shaker to induce cell lysis. The plate was then incubated at room temperature for 10 minutes to stabilize the luminescent signal and read on a Tecan F200 Pro microplate reader.

Multiplex Gene Expression (MGE) Profiling 96-well plates were seeded with HEK293 cells, 20,000 cells/well and incubated at 37° C. overnight. Cells were treated with compounds in media to give a final concentration of 10 μM and incubated for 6 h. Media was removed then cell pellets in the plates were frozen at −80° C. On day of assay, cell pellets were thawed, lysed and analyzed for gene expression as previously described[5].

Quantitative RT-PCR

Cells were treated as described at 37° C., washed with Dulbecco's phosphate-buffered saline (Gibco), and then RNA was extracted using the RNeasy Mini Kit (Qiagen). qPCR reactions were performed on cDNA prepared from 500 ng of total cellular RNA using the QuantiTect Reverse Transcription Kit (Qiagen). The FastStart Universal SYBR Green Master Mix (Roche), cDNA, and appropriate human primers[4] or mouse primers (BiP; GTCCAGGCTGGTGTCCTCTC (SEQ ID NO: 5) and GATTATCGGAAGCCGTGGAG (SEQ ID NO: 6) purchased from Integrated DNA Technologies were used for amplifications (45 cycles of 1 min at 95° C., 10 s at 95° C., 30 sec at 60° C.) in an ABI 7900HT Fast Real Time PCR machine. Primer integrity was assessed by a thermal melt to confirm homogeneity and the absence of primer dimers. Transcripts were normalized to the housekeeping gene Rplp2 and all measurements were performed in triplicate. Data were analyzed using the RQ Manager and DataAssist 2.0 softwares (ABI).

XBP1 splicing was assessed by RT-PCR followed by gel electrophoresis on a 3% agarose gel using primers the following primers flanking the XBP1 splicing sites:

5'-CCTTGTAGTTGAGAACCAGG-3' (SEQ ID NO: 7),
5'-GAGTCAATACCGCCAGAATC-3' (SEQ ID NO: 8).

ATF6 Nuclear Localization

300 μL of 1.375×104 U2OS-GFP-ATF6 cells per ml were plated per well in 96 well imaging plate (ibidi 89626) and sealed with breathable seals (E&K Scientific T896100) two days prior to drug addition. Immediately prior to addition to cells, compounds were diluted to 6× in media from 500× DMSO stock and 60 μL 6× was added to cells for 1× final (0.2% DMSO).

After 5h, media was removed and cells were fixed in 4% PFA (Electron Microscopy Sciences 15714) in PHEM buffer (60 mM PIPES, 25 mM HEPES, 10 mM EGTA, 2 mM MgCl2-hexahydrate, pH 6.9) for 15 minutes at RT. Cells were permeabilized with PHEM-Tx (PHEM containing 0.1% Triton X-100, two washes, 5 min at RT), washed twice in PHEM and blocked in PHEM containing 2% normal goat serum (Jackson Immunoresearch Laboratories 005-000-121) for 1 hour at RT. Primary antibodies were incubated in blocking solution overnight at 4 degrees. Cells were washed three times in PHEM-Tx then incubated with secondary antibodies and nuclear stain (DAPI, Molecular Probes D-1306, 5 μg/ml) in blocking solution for 2 hours at RT protected from light. Cells were washed three times in PHEM-Tx, then twice in PHEM. Antibodies used were rat anti-GRP94 9G10 (Abcam ab2791), mouse anti-GFP 3E6 (Invitrogen A11120), anti-rat-Alexa-555 (Invitrogen A21434), and anti-mouse-Alexa-488 (Invitrogen A11029), each at 1:1000 dilution.

Plate was imaged on a spinning disk confocal with Yokogawa CSUX A1 scan head, Andor iXon EMCCD camera and 20× Plan Apo Objective NA 0.79. Using the μManager high-content screening plugin "HCS Site Generator"[6] 49 fields per well were acquired for a mean cell number per well of 368±12.

Images were analyzed using CellProfiler[7], MATLAB R2014a and GraphPad Prism 5. Masks for the ER and nucleus of each cell were created using the GRP94 and DAPI staining, respectively. The ratio of the GFP intensity in the nucleus versus the ER was calculated for each cell and plotted as a histogram per well. A threshold for the minimum ratio of nuclear to ER signal corresponding to an activated (i.e. nuclear localized ATF6) cell was calculated as the minimum nuclear: ER ratio greater than 1 where the number of ER stressed cells (Tg) was greater than the corresponding unstressed control. Percent activation per well was calculated as the percentage of cells per well with a nuclear: ER ratio greater than the calculated threshold for that plate. Mean percent activation per well for a minimum of three replicate wells per treatment was plotted and error bars are standard error of the mean. Compounds are annotated as hits if they show percent activation more than three standard deviations away from the mean of vehicle treated control.

mRNA-Seq

HEK293T-Rex and HEK293$^{DAX}$ cells in 12-well plates were treated for 6 h with vehicle, 1 μM Tg, 10 μM TMP (in HEK293$^{DAX}$), or 10 μM 132, 147 or 263 in biological triplicate at 37° C. Cells were harvested, and RNA was extracted using the RNeasy Mini Kit (Qiagen). Total RNA was quantified using NanoDrop (ND-1000). Samples were run on the Illuina HiSeq system.

Single end, 100 bp-long reads from RNA-Seq experiments were aligned to the GRCh37.p13 human genome reference assembly using SeqMan NGen 11.2.1 (DNAStar, Inc.). The assembly data were then imported into ArrayStar with QSeq (DNAStar, Inc.) to quantify the gene expression levels. The sequence counts were normalized to reads per kilobase per million (RPKM) after filtering out non-mRNA sequence features. The statistical significance of the difference between the expression levels of a gene under different conditions was assessed using a Student's t-test with the Benjamini-Hochberg multiple testing correction.

Geneset Analysis of Transcriptional Data

ATF6- and XBP1s-selective target genes were identified from transcriptional profiles of HEK293D$^X$ cells following stress-independent activation of TMP-dependent DHFR-ATF6 and/or tetracycline inducible XBP1s, as previously described[4]. PERK-selective target genes were identified from[8]. Only ATF6-, XBP1s- or PERK-selective genes induced >1.5 fold in Tg-treated samples were used in this analysis. The log transformed fold-increase of these target genes in HEK293T-Rex cells treated with the respective ER proteostasis regulators were then normalized to the log transformed fold increase of these genes induced by Tg treatment. The plots shown in FIG. 5b-e were prepared as box and whisker plots using Kaleidograph. Differential activation of the ATF6, XBP1s, and PERK genesets was assessed by one-way ANOVA and significance of pairwise comparison confirmed by unpaired t-test. An analogous strategy was employed to prepare the heat map using transcriptional data from the MGE analysis.

Proteomics by TMT-MuDPIT

HEK293T-Rex cells in 6-well plates were treated for 16 h with vehicle, or 132, 147 or 263 at 37° C. Lysates were prepared in radioimmunoprecipitation assay (RIPA) buffer (150 mM NaCl, 50 mM Tris pH 7.5, 1% Triton X-100, 0.5% sodium deoxycholate, and 0.1% SDS) with fresh protease inhibitor cocktail (Roche) and centrifuged for 20 min at 10000×g. Protein concentrations of supernatants were determined by BCA (Pierce). For each sample, 100 μg of lysate was washed by chloroform/methanol precipitation. Air-dried pellets were resuspended in 1% RapiGest SF (Waters) and brought up in 100 mM HEPES (pH 8.0). Proteins were reduced with 5 mM Tris(2-carboxyethyl)phosphine hydrochloride (Pierce) for 30 min and alkylated with 10 mM iodoacetamide (Sigma) for 30 min at ambient temperature and protected from light. Proteins were digested for 18 h at 37° C. with 2 μg trypsin (Promega). After digestion, 20 μg of peptides from each sample were reacted for 1 h with the appropriate TMT-NHS isotopic label (Pierce) in 40% (v/v) anhydrous acetonitrile and quenched with 0.4% NH$_4$HCO$_3$ for 1 h. Samples with different TMT labels were pooled and acidified with 5% formic acid. Acetonitrile was evaporated on a SpeedVac and debris was removed by centrifugation for 30 min at 18000×g. MuDPIT microcolumns were prepared as described[9]. LCMS/MS analysis was performed using a Q Exactive mass spectrometer equipped with an EASY nLC 1000 (Thermo Scientific, San Jose, Calif.). MuDPIT experiments were performed by 5 min sequential injections of 0, 10, 20, 30, ..., 100% buffer C (500 mM ammonium acetate in buffer A) and a final step of 90% buffer C/10% buffer B (20% water, 80% acetonitrile, 0.1% formic acid, v/v/v) and each step followed by a gradient from buffer A (95% water, 5% acetonitrile, 0.1% formic acid) to buffer B. Electrospray was performed directly from the analytical column by applying a voltage of 2.5 kV with an inlet capillary temperature of 275° C. Data-dependent acquisition of MS/MS spectra were performed with the following settings: eluted peptides were scanned from 100 to 1800 m/z with a resolution of 30000 and the mass spectrometer in a data dependent acquisition mode. The top ten peaks for each full scan were fragmented by HCD using a normalized collision energy of 30%, a 100 ms activation time, and a resolution of 7500. Dynamic exclusion parameters were 1 repeat count, 30 ms repeat duration, 500 exclusion list size, 120 s exclusion duration, and exclusion width between 0.51 and 1.51. Peptide identification and protein quantification was performed using the Integrated Proteomics Pipeline Suite (IP2, Integrated Proteomics Applications, Inc.) as described previously[9]. The geneset analysis (Supplementary FIG. 5f-k) was performed analogous to the analysis of the RNA-seq data using the same genesets for ATF6, XBP1s and PERK and log transformed fold changes of protein expression. The plots shown in FIG. 5b-e were prepared as box and whisker plots using Kaleidograph. Differential activation of the ATF6, XBP1s, and PERK genesets was assessed by one-way ANOVA and significance of pairwise comparison confirmed by unpaired t-test.

[$^{35}$S] Metabolic Labeling Experiments

HepG2 cells or HEK293T cells plated on poly-D-lysine coated plates were metabolically labeled in DMEM-Cys/-Met (CellGro) supplemented with glutamine, penicillin/streptomycin, dialyzed fetal bovine serum, and EasyTag EXPRESS$^{35}$S Protein Labeling Mix (Perkin Elmer) for 30 min. Cells were washed twice with complete media and incubated in prewarmed DMEM for the indicated times. Media or lysates were harvested at the indicated times. Lysates were prepared in RIPA buffer with fresh protease inhibitor cocktail (Roche). FLAG tagged TTR variants or ALLC were immunopurified using M1 anti-FLAG agarose beads (Sigma-Aldrich) and washed three times with RIPA buffer. The immunoisolates were then eluted by boiling in Laemmli buffer and separated on SDS-PAGE. For total secreted media, 15 uL aliquots from media incubated for 4 hrs on pulsed cells were run on a SDS-PAGE. The gels were then dried, exposed to phosphorimager plates (GE Healthcare), and imaged with a Typhoon imager. Band intensities were quantified by densitometry in ImageQuant. Fraction secreted was calculated using the equation: fraction secreted=[extracellular [$^{35}$S]-LC signal at t=t/(extracellular [$^{35}$S]-LC signal at t=0+intracellular [$^{35}$S]-LC signal at t=0)]. Fraction remaining was calculated using the equation: [(extracellular [$^{35}$S]-LC signal at t=t+intracellular [$^{35}$S]-LC signal at t=t)/(extracellular [$^{35}$S]-LC signal at t=0+ intracellular [$^{35}$S]-LC signal at t=0)].

Immunoblotting, SDS-PAGE and Immunoprecipitation

For immunoblotting, cells were lysed in 50 mM Tris buffer, pH 7.5 containing 0.1% TritonX (Fisher Scientific) and supplemented with protease inhibitor cocktail (Roche). For immunoblots of endogenous ATF6, cells were washed in PBS containing protease inhibitor cocktail and 10 μM MG-132 and subsequently lysated in 1× Laemmli buffer, supplemented in the same way, by repeating cycles of boiling and vortexing. Protein lysate concentrations were normalized by Bradford assays (Bio-Rad). Lysates or media were boiled for 10 min in Laemmli buffer+100 mM DTT before loading onto SDS-PAGE gel. Proteins were transferred from gel slabs to nitrocellulose, and the Odyssey Infrared Imaging System (Li-Cor Biosciences) was used to detect proteins of interest.

For immunoprecipitations, cells were washed with PBS then cross-linked with 0.5 mM Dithiobis(succinimidyl propionate) (DSP) for 30 min at room temperature. The reaction was quenched by addition of 100 mM Tris pH 7.5, then RIPA buffer was added to the cell pellets for lysis. Lysates were cleared by centrifugation at centrifuged at 10000×g for 15 min. Proteins were immunopurified using sheep polyclonal free λ LC antibody (Bethyl Laboratories A80-127A) that was covalently conjugated to CNBr-activated Sepharose 4B (GE Healthcare). After four washes in RIPA buffer, proteins were eluted by boiling in Laemmli buffer+100 mM DTT and samples were separated by SDS-PAGE and transferred to nitrocellulose membranes. Blots were probed with the following primary antibodies: monoclonal mouse M2 anti-FLAG (1:500, Sigma), polyclonal rabbit anti-TTR (1:1000, Dako), rabbit polyclonal anti-human lambda light chain (1:1000, Bethyl Laboratories A90-112A), mouse monoclonal anti-Grp78 (1:500, Santa Cruz Biotechnology sc-166490), rabbit polyclonal anti-Grp94 (1:1000, GeneTex GTX103203), rabbit polyclonal anti-PDIA4 (1:1000, Protein Tech Group 14712-1-AP), mouse monoclonal anti-ATF6a (1-7) (BioAcademia, 1:1000), rabbit anti-phospho eIF2α (CellSignaling #9721, 1:500), mouse anti-eIF2α (Abcam ab5369, 1:1000) and mouse monoclonal anti β-actin (1:10000, Sigma).

Light Chain ELISA

ALMC-2 or KAS-6/1 plasma cells were plated 100,000 cells/well in 150 μL of media in 96-well MultiScreen$_{HTS}$ filtration plates (Millipore MSBVS1210). Triplicate wells were treated with DMSO or compounds at the indicated concentrations and incubated for 16 h. Media was removed by filtration using a QIAvac 96 vacuum manifold (Qiagen) and wells were washed two times with 150 μL media. Wells were then incubated with 150 μL of fresh media for 2 hr and the conditioned media was harvested into a 96-well plate using the vacuum manifold. Free λLC and IgG concentrations were determined by ELISA in 96-well plates (Immulon 4HBX, Thermo Scientific). Wells were coated overnight at 37° C. with rabbit anti-human A light chain polyclonal antibody (Bethyl Laboratories, A90-112A) at a 1:1000 dilution or human IgG-heavy and light chain antibody (Bethyl Laboratories, A80-118A) at a 1:2000 dilution in 50 mM sodium carbonate (pH 9.6). In between all incubation steps, the plates were rinsed extensively with Tris-buffered saline containing 0.05% Tween-20 (TBST). Plates were blocked with 5% non-fat dry milk in TBST for 1 h at 37° C. Media analytes were diluted between 5-200 fold in 5% non-fat dry milk in TBST and 100 μL of each sample was added to individual wells. Light chain or IgG standards ranging from 3-300 ng/mL were prepared from purified human Bence Jones A light chain or human reference serum (Bethyl Laboratories, P80-127 and RS10-110). Plates were incubated at 37° C. for 1.5 h while shaking. Finally, HRP-conjugated goat anti-human A light chain antibody (Bethyl Laboratories, A80-116P) was added at a 1:10,000 dilution or HRP-conjugate IgG-Fc fragment cross-adsorbed antibody (Bethyl Laboratories, A80-304P, 1:30,000 dilution) was added in 5% non-fat dry milk in TBST, followed by a 1.5 h incubation of the plates at 37° C. The detection was carried out with 2,2'-azinobis(3-ethylbenzothiazoline-6-sulfonic acid) (ABTS, 0.18 mg/mL) and 0.03% hydrogen peroxide in 100 mM sodium citrate pH 4.0. Detection solution (100 μL) was added to each well and the plates were incubated at room temperature. The absorbance was recorded at 405 nm and the values for the LC standards were fitted to a 4-parameter logistic function. Light chain or IgG concentrations were averaged from at least 3 independent replicates under each treatment and then normalized to vehicle conditions.

Conditioned Media Aggregation and Blue-Native PAGE

ALMC-2 plasma cells were plated 2 10$^6$ cells/well in 1 mL of media in 12-well plates. Wells were treated with DMSO or 10 μL of compounds and incubated for 16 h. Cells were transferred to microcentrifuge tubes and washed two times in media. Small aliquots (10 μL) of cells were removed for a Cytotoxicity assay as described above. Cells were resuspended in media (1 mL for DMSO treatment) and the volume was adjusted for each treatment based on cell viability.

Cells were conditioned in the media for 8 h and then were removed by centrifugation. The media samples were immunoprecipitated overnight at 4° C. with recombinant Protein A—Sepharose 4B resin (Life Technologies) to remove fully assembled IgGs that interfere with LC aggregate detection. Cleared media samples were then heated to 55° C. for 8 h to induce LC aggregation, added to Blue-Native PAGE loading dye (10% glycerol, 0.5% Coomassie G-250) and then loaded onto 3-12% Bis-Tris gradient gels (Life Technologies). The cathode buffer contained 50 mM Tricene and 15 mM Bis-Tris, pH 7.0 with 0.02% Coomassie G-250. The anode buffer contained 50 mM Bis-Tris pH 7.0. The gels were transferred onto PVDF membranes and LC was detected by rabbit anti-human A light chain polyclonal antibody (Bethyl), followed by HRP-conjugated secondary antibodies. The blots were imaged using a chemiluminescence substrate (Luminata Forte Western Luminescence Substrate, Millipore) and imaged with a ChemiDoc XRS+ scanner (Bio-rad).

Statistical Methods

Unless otherwise noted, all p-values were calculated by performing a paired or unpaired (noted) t-test.

DOCUMENTS CITED IN EXAMPLES

1 Yoshida, H., Haze, K., Yanagi, H., Yura, T. & Mori, K. Identification of the cis-acting endoplasmic reticulum stress response element responsible for transcriptional induction of mammalian glucose-regulated proteins. Involvement of basic leucine zipper transcription factors. *J Biol Chem* 273, 33741-33749 (1998).

2 Iwawaki, T., Akai, R., Kohno, K. & Miura, M. A transgenic mouse model for monitoring endoplasmic reticulum stress. *Nat Med* 10, 98-102, doi:10.1038/nm970 (2004).

3 Klock, H. E. & Lesley, S. A. The Polymerase Incomplete Primer Extension (PIPE) method applied to high-throughput cloning and site-directed mutagenesis. *Methods in molecular biology* (Clifton, N.J.) 498, 91-103, doi: 10.1007/978-1-59745-196-3_6 (2009).

4 Shoulders, M. D. et al. Stress-independent activation of XBP1s and/or ATF6 reveals three functionally diverse ER proteostasis environments. *Cell Rep* 3, 1279-1292, doi: 10.1016/j.celrep.2013.03.024 (2013).

5 Calamini, B. et al. Small-molecule proteostasis regulators for protein conformational diseases. *Nat Chem Biol* 8, 185-196, doi:10.1038/nchembio.763 (2012).

6 Edelstein, A. D. et al. Advanced methods of microscope control using muManager software. *Journal of biological methods* 1, doi:10.14440/jbm.2014.36 (2014).

7 Carpenter, A. E. et al. CellProfiler image analysis software for identifying and quantifying cell phenotypes. *Genome biology* 7, R100, doi: 10.1186/gb-2006-7-10-r100 (2006).

8 Lu, P. D. et al. Cytoprotection by pre-emptive conditional phosphorylation of translation initiation factor 2. *The EMBO journal* 23, 169-179, doi:10.1038/sj.emboj.7600030 (2004).

9 Ryno, L. M. et al. Characterizing the altered cellular proteome induced by the stress-independent activation of heat shock factor 1. *ACS Chem Biol* 9, 1273-1283, doi: 10.1021/cb500062n (2014).

DOCUMENTS CITED IN THE DISCLOSURE

The following documents are incorporated by reference in the disclosure of the present application for patent.

1 Kleizen, B. & Braakman, I. Protein folding and quality control in the endoplasmic reticulum. *Curr Opin Cell Biol* 16, 343-349, doi:10.1016/j.ceb.2004.06.012 (2004).

2 Balch, W. E., Morimoto, R. I., Dillin, A. & Kelly, J. W. Adapting proteostasis for disease intervention. *Science* 319, 916-919, doi:10.1126/science.1141448 (2008).

3 Brodsky, J. L. & Skach, W. R. Protein folding and quality control in the endoplasmic reticulum: Recent lessons from yeast and mammalian cell systems. *Curr Opin Cell Biol* 23, 464-475, doi:10.1016/j.ceb.2011.05.004 (2011).

4 Brandizzi, F. & Barlowe, C. in *Nat Rev Mol Cell Biol Vol.* 14 382-392 (2013).

5 Smith, M. H., Ploegh, H. L. & Weissman, J. S. Road to ruin: targeting proteins for degradation in the endoplasmic reticulum. *Science* 334, 1086-1090, doi: 10.1126/science.1209235 (2011).

6 Powers, E. T., Morimoto, R. I., Dillin, A., Kelly, J. W. & Balch, W. E. Biological and chemical approaches to diseases of proteostasis deficiency. *Annu Rev Biochem* 78, 959-991, doi:10.1146/annurev.biochem.052308.114844 (2009).

7 Gooptu, B., Dickens, J. A. & Lomas, D. A. The molecular and cellular pathology of alpha(1)-antitrypsin deficiency. *Trends in molecular medicine* 20, 116-127, doi:10.1016/j.molmed.2013.10.007 (2014).

8 Perlmutter, D. H. & Silverman, G. A. in *Cold Spring Harbor perspectives in biology* Vol. 3 a005801-a005801 (Cold Spring Harbor Lab, 2011).

9 Tzekov, R., Stein, L. & Kaushal, S. in *Cold Spring Harbor perspectives in biology* Vol. 3 a007492-a007492 (Cold Spring Harbor Lab, 2011).

10 Blancas-Mejia, L. M. & Ramirez-Alvarado, M. Systemic amyloidoses. *Annu Rev Biochem* 82, 745-774, doi: 10.1146/annurev-biochem-072611-130030 (2013).

11 Eisele, Y. S. et al. Targeting protein aggregation for the treatment of degenerative diseases. *Nature reviews. Drug discovery* 14, 759-780, doi:10.1038/nrd4593 (2015).

12 Calamini, B. & Morimoto, R. I. Protein homeostasis as a therapeutic target for diseases of protein conformation. *Current topics in medicinal chemistry* 12, 2623-2640 (2012).

13 Lindquist, S. L. & Kelly, J. W. Chemical and biological approaches for adapting proteostasis to ameliorate protein misfolding and aggregation diseases: progress and prognosis. *Cold Spring Harbor perspectives in biology* 3, doi:10.1101/cshperspect.a004507 (2011).

14 Ryno, L. M., Wiseman, R. L. & Kelly, J. W. Targeting unfolded protein response signaling pathways to ameliorate protein misfolding diseases. *Curr Opin Chem Biol* 17, 346-352, doi:10.1016/j.cbpa.2013.04.009 (2013).

15 Chen, J. J., Genereux, J. C. & Wiseman, R. L. in *IUBMB life* Vol. 67 404-413 (2015).

16 Walter, P. & Ron, D. The unfolded protein response: from stress pathway to homeostatic regulation. *Science* 334, 1081-1086, doi:10.1126/science.1209038 (2011).

17 Yoshida, H. Unconventional splicing of XBP-1 mRNA in the unfolded protein response. *Antioxid Redox Signal* 9, 2323-2333, doi: 10.1089/ars.2007.1800 (2007).

18 Ye, J. et al. ER stress induces cleavage of membrane-bound ATF6 by the same proteases that process SREBPs. *Mol Cell* 6, 1355-1364 (2000).

19 Yamamoto, K., Yoshida, H., Kokame, K., Kaufman, R. J. & Mori, K. Differential contributions of ATF6 and XBP1 to the activation of endoplasmic reticulum stress-responsive cis-acting elements ERSE, UPRE and ERSE-II. *J Biochem* 136, 343-350, doi:10.1093/jb/mvh122 (2004).

20 Adachi, Y. et al. ATF6 is a transcription factor specializing in the regulation of quality control proteins in the endoplasmic reticulum. *Cell Struct Funct* 33, 75-89 (2008).

21 Shoulders, M. D. et al. Stress-independent activation of XBP1s and/or ATF6 reveals three functionally diverse ER proteostasis environments. *Cell reports* 3, 1279-1292, doi:10.1016/j.celrep.2013.03.024 (2013).

22 Chiang, W. C., Hiramatsu, N., Messah, C., Kroeger, H. & Lin, J. H. Selective activation of ATF6 and PERK endoplasmic reticulum stress signaling pathways prevent mutant rhodopsin accumulation. *Invest Ophthalmol Vis Sci* 53, 7159-7166, doi:10.1167/iovs.12-10222 (2012).

23 Jerry Chiang, W. C. & Lin, J. H. The effects of IRE1, ATF6, and PERK signaling on adRP-linked rhodopsins. *Adv Exp Med Biol* 801, 661-667, doi:10.1007/978-1-4614-3209-8_83 (2014).

24 Smith, S. E. et al. Activating transcription factor 6 limits intracellular accumulation of mutant alpha(1)-antitrypsin Z and mitochondrial damage in hepatoma cells. *The Journal of biological chemistry* 286, 41563-41577, doi: 10.1074/jbc.M111.280073 (2011).

25 Chen, J. J. et al. ATF6 activation reduces the secretion and extracellular aggregation of destabilized variants of an amyloidogenic protein. *Chemistry & biology* 21, 1564-1574, doi:10.1016/j.chembiol.2014.09.009 (2014).

26 Cooley, C. B. et al. Unfolded protein response activation reduces secretion and extracellular aggregation of amyloidogenic immunoglobulin light chain. *Proceedings of the National Academy of Sciences of the United States of America* 111, 13046-13051, doi:10.1073/pnas.1406050111 (2014).

27 Maly, D. J. & Papa, F. R. Druggable sensors of the unfolded protein response. *Nature chemical biology* 10, 892-901, doi:10.1038/nchembio.1664 (2014).

28 Hetz, C. in *Nat Rev Mol Cell Biol* (2012).

29 Tabas, I. & Ron, D. in *Nat Cell Biol* Vol. 13 184-190 (2011).

30 Papa, F. R., Zhang, C., Shokat, K. & Walter, P. Bypassing a kinase activity with an ATP-competitive drug. *Science* 302, 1533-1537, doi: 10.1126/science.1090031 (2003).

31 Wang, L. et al. Divergent allosteric control of the IRE1alpha endoribonuclease using kinase inhibitors. *Nature chemical biology* 8, 982-989, doi:10.1038/nchembio.1094 (2012).

32 Mendez, A. S. et al. Endoplasmic reticulum stress-independent activation of unfolded protein response kinases by a small molecule ATP-mimic. *eLife* 4, doi: 10.7554/eLife.05434 (2015).

33 Kudo, T. et al. A molecular chaperone inducer protects neurons from ER stress. *Cell death and differentiation* 15, 364-375, doi:10.1038/sj.cdd.4402276 (2008).

34 Yoshida, H., Haze, K., Yanagi, H., Yura, T. & Mori, K. Identification of the cis-acting endoplasmic reticulum stress response element responsible for transcriptional induction of mammalian glucose-regulated proteins. Involvement of basic leucine zipper transcription factors. *The Journal of biological chemistry* 273, 33741-33749 (1998).

35 Calamini, B. et al. Small-molecule proteostasis regulators for protein conformational diseases. *Nature chemical biology* 8, 185-196, doi:10.1038/nchembio.763 (2012).

36 Back, S. H., Lee, K., Vink, E. & Kaufman, R. J. Cytoplasmic IRE1alpha-mediated XBP1 mRNA splicing in the absence of nuclear processing and endoplasmic reticulum stress. *The Journal of biological chemistry* 281, 18691-18706, doi: 10.1074/jbc. M602030200 (2006).

37 Iwawaki, T., Akai, R., Kohno, K. & Miura, M. A transgenic mouse model for monitoring endoplasmic reticulum stress. *Nat Med* 10, 98-102, doi:10.1038/nm970 (2004).

38 Wu, J. et al. ATF6alpha optimizes long-term endoplasmic reticulum function to protect cells from chronic stress. *Developmental cell* 13, 351-364, doi:10.1016/j.devcel.2007.07.005 (2007).

39 Hay, B. A. et al. Aminopyrrolidineamide inhibitors of site-1 protease. *Bioorg Med Chem Lett* 17, 4411-4414, doi:10.10161j.bmcl.2007.06.031 (2007).

40 Ryno, L. M. et al. Characterizing the altered cellular proteome induced by the stress-independent activation of heat shock factor 1. *ACS chemical biology* 9, 1273-1283, doi:10.1021/cb500062n (2014).

41 Yang, Y. et al. An overview of the molecular mechanisms and novel roles of Nrf2 in neurodegenerative disorders. *Cytokine Growth Factor Rev* 26, 47-57, doi:10.1016/j.cytogfr.2014.09.002 (2015).

42 Lu, P. D. et al. Cytoprotection by pre-emptive conditional phosphorylation of translation initiation factor 2. *The EMBO journal* 23, 169-179, doi:10.1038/sj.emboj.7600030 (2004).

43 Shoulders, M. D., Ryno, L. M., Cooley, C. B., Kelly, J. W. & Wiseman, R. L. in *Journal of the American Chemical Society* Vol. 135 8129-8132 (2013).

44 Arendt, B. K. et al. Biologic and genetic characterization of the novel amyloidogenic lambda light chain-secreting human cell lines, ALMC-1 and ALMC-2. *Blood* 112, 1931-1941, doi: 10.1182/blood-2008-03-143040 (2008).

45 Westendorf, J. J. et al. Establishment and characterization of three myeloma cell lines that demonstrate variable cytokine responses and abilities to produce autocrine interleukin-6. *Leukemia* 10, 866-876 (1996).

46 Das, I. et al. Preventing proteostasis diseases by selective inhibition of a phosphatase regulatory subunit. *Science (New York, N. Y)* 348, 239-242, doi:10.1126/science.aaa4484 (2015).

47 Calamini, B. et al. in *Nat. Chem. Biol.* Vol. 8 185-196 (2012).

48 Shen, J., Chen, X., Hendershot, L. & Prywes, R. ER stress regulation of ATF6 localization by dissociation of BiP/GRP78 binding and unmasking of Golgi localization signals. *Developmental cell* 3, 99-111 (2002).

49 Nadanaka, S., Okada, T., Yoshida, H. & Mori, K. Role of disulfide bridges formed in the luminal domain of ATF6 in sensing endoplasmic reticulum stress. *Molecular and cellular biology* 27, 1027-1043, doi: 10.1128/mcb.00408-06 (2007).

50 Wiseman, R. L. et al. Flavonol activation defines an unanticipated ligand-binding site in the kinase-RNase domain of IRE1. *Molecular cell* 38, 291-304, doi: 10.1016/j.molcel.2010.04.001 (2010).

51 Howarth, D. L. et al. Activating transcription factor 6 is necessary and sufficient for alcoholic fatty liver disease in zebrafish. *PLoS genetics* 10, e1004335, doi:10.1371/journal.pgen.1004335 (2014).

Therapeutic Potential for ATF6 Activation

The following documents, referred to in the Disclosure, above, and incorporated by reference in their entireties, describe medical conditions wherein it is believed that preferentially activating the activating transcription factor 6 (ATF6) arm of the unfolded protein response (UPR) in the endoplasmic reticulum of a cell, by contacting the cell or administering to a patient afflicted by the medical condition or disease with an effective amount of dose of a compound of any one of formulas (I) through (IX) as described herein, will provide a beneficial effect in treatment of the medical condition or disease. It is within ordinary skill to evaluate a compound of any one of formulas (I) through (IX) described herein as suitable for practicing a method of the invention for treatment of the medical conditions or diseases described in the following documents.

1 Powers, E. T., Morimoto, R. I., Dillin, A., Kelly, J. W. & Balch, W. E. Biological and chemical approaches to diseases of proteostasis deficiency. *Annual review of biochemistry* 78, 959-991, doi: 10.1146/annurev.biochem.052308.114844 (2009).
2 Eisele, Y. S. et al. Targeting protein aggregation for the treatment of degenerative diseases. *Nature reviews. Drug discovery* 14, 759-780, doi:10.1038/nrd4593 (2015).
3 Chen, J. J., Genereux, J. C. & Wiseman, R. L. Endoplasmic reticulum quality control and systemic amyloid disease: Impacting protein stability from the inside out. *IUBMB life* 67, 404-413, doi:10.1002/iub.1386 (2015).
4 Ryno, L. M., Wiseman, R. L. & Kelly, J. W. Targeting unfolded protein response signaling pathways to ameliorate protein misfolding diseases. *Current opinion in chemical biology* 17, 346-352, doi:10.1016/j.cbpa.2013.04.009 (2013).
5 Chen, J. J. et al. ATF6 activation reduces the secretion and extracellular aggregation of destabilized variants of an amyloidogenic protein. *Chemistry & biology* 21, 1564-1574, doi:10.1016/j.chembiol.2014.09.009 (2014).
6 Cooley, C. B. et al. Unfolded protein response activation reduces secretion and extracellular aggregation of amyloidogenic immunoglobulin light chain. *Proceedings of the National Academy of Sciences of the United States of America* 111, 13046-13051, doi:10.1073/pnas.1406050111 (2014).
7 Shoulders, M. D., Ryno, L. M., Cooley, C. B., Kelly, J. W. & Wiseman, R. L. Broadly applicable methodology for the rapid and dosable small molecule-mediated regulation of transcription factors in human cells. *Journal of the American Chemical Society* 135, 8129-8132, doi: 10.1021/ja402756p (2013).
8 Genereux, J. C. et al. Unfolded protein response-induced ERdj3 secretion links ER stress to extracellular proteostasis. *The EMBO journal* 34, 4-19, doi:10.15252/embj.201488896 (2015).
9 Smith, S. E. et al. Activating transcription factor 6 limits intracellular accumulation of mutant alpha(1)-antitrypsin Z and mitochondrial damage in hepatoma cells. *The Journal of biological chemistry* 286, 41563-41577, doi: 10.1074/jbc.M111.280073 (2011).
10 Chiang, W. C., Hiramatsu, N., Messah, C., Kroeger, H. & Lin, J. H. Selective activation of ATF6 and PERK endoplasmic reticulum stress signaling pathways prevent mutant rhodopsin accumulation. *Investigative ophthalmology & visual science* 53, 7159-7166, doi:10.1167/iovs.12-10222 (2012).
11 Wang, F. & Segatori, L. Remodeling the proteostasis network to rescue glucocerebrosidase variants by inhibiting ER-associated degradation and enhancing ER folding. *PloS one* 8, e61418, doi:10.1371/journal.pone.0061418 (2013).
12 Tan, Y. L. et al. ERdj3 is an endoplasmic reticulum degradation factor for mutant glucocerebrosidase variants linked to Gaucher's disease. *Chemistry & biology* 21, 967-976, doi: 10.1016/j.chembiol.2014.06.008 (2014).
13 Ong, D. S. et al. FKBP10 depletion enhances glucocerebrosidase proteostasis in Gaucher disease fibroblasts. *Chemistry & biology* 20, 403-415, doi:10.1016/j.chembiol.2012.11.014 (2013).
14 Ong, D. S., Mu, T. W., Palmer, A. E. & Kelly, J. W. Endoplasmic reticulum Ca2+ increases enhance mutant glucocerebrosidase proteostasis. *Nature chemical biology* 6, 424-432, doi: 10.1038/nchembio.368 (2010).
15 Mu, T. W. et al. Chemical and biological approaches synergize to ameliorate protein-folding diseases. *Cell* 134, 769-781, doi:10.1016/j.cell.2008.06.037 (2008).
16 Wang, F., Song, W., Brancati, G. & Segatori, L. Inhibition of endoplasmic reticulum-associated degradation rescues native folding in loss of function protein misfolding diseases. *The Journal of biological chemistry* 286, 43454-43464, doi:10.1074/jbc.M111.274332 (2011).
17 Di, X. J., Han, D. Y., Wang, Y. J., Chance, M. R. & Mu, T. W. SAHA enhances Proteostasis of epilepsy-associated alpha1 (A322D)beta2gamma2 GABA(A) receptors. *Chemistry & biology* 20, 1456-1468, doi:10.1016/j.chembiol.2013.09.020 (2013).
18 Han, D. Y., Di, X. J., Fu, Y. L. & Mu, T. W. Combining valosin-containing protein (VCP) inhibition and suberanilohydroxamic acid (SAHA) treatment additively enhances the folding, trafficking, and function of epilepsy-associated gamma-aminobutyric acid, type A (GABAA) receptors. *The Journal of biological chemistry* 290, 325-337, doi:10.1074/jbc.M114.580324 (2015).
19 Glembotski, C. C. Roles for ATF6 and the sarco/endoplasmic reticulum protein quality control system in the heart. *Journal of molecular and cellular cardiology* 71, 11-15, doi:10.1016/1.yjmcc.2013.09.018 (2014).
20 Glembotski, C. C. The role of the unfolded protein response in the heart. *Journal of molecular and cellular cardiology* 44, 453-459, doi: 10.1016/j.yjmcc.2007.10.017 (2008).
21 Minamino, T., Komuro, I. & Kitakaze, M. Endoplasmic reticulum stress as a therapeutic target in cardiovascular disease. *Circulation research* 107, 1071-1082, doi: 10.1161/CIRCRESAHA.110.227819 (2010).
22 Minamino, T. & Kitakaze, M. ER stress in cardiovascular disease. *Journal of molecular and cellular cardiology* 48, 1105-1110, doi:10.1016/j.yjmcc.2009.10.026 (2010).
23 Groenendyk, J., Sreenivasaiah, P. K., Kim do, H., Agellon, L. B. & Michalak, M. Biology of endoplasmic reticulum stress in the heart. *Circulation research* 107, 1185-1197, doi: 10.1161/CIRCRESAHA.110.227033 (2010).
24 Doroudgar, S., Thuerauf, D. J., Marcinko, M. C., Belmont, P. J. & Glembotski, C. C. Ischemia activates the ATF6 branch of the endoplasmic reticulum stress response. *The Journal of biological chemistry* 284, 29735-29745, doi:10.1074/jbc.M109.018036 (2009).
25 Toko, H. et al. ATF6 is important under both pathological and physiological states in the heart. *Journal of molecular and cellular cardiology* 49, 113-120, doi:10.1016/j.yjmcc.2010.03.020 (2010).
26 Martindale, J. J. et al. Endoplasmic reticulum stress gene induction and protection from ischemia/reperfusion injury in the hearts of transgenic mice with a tamoxifen-regulated form of ATF6. *Circulation research* 98, 1186-1193, doi:10.1161/01.RES.0000220643.65941.8d (2006).
27 Fu, H. Y. et al. Overexpression of endoplasmic reticulum-resident chaperone attenuates cardiomyocyte death induced by proteasome inhibition. *Cardiovascular research* 79, 600-610, doi:10.1093/cvr/cvn128 (2008).
28 Tadimalla, A. et al. Mesencephalic astrocyte-derived neurotrophic factor is an ischemia-inducible secreted endoplasmic reticulum stress response protein in the heart. *Circulation research* 103, 1249-1258, doi: 10.1161/CIRCRESAHA. 108.180679 (2008).

29. Belmont, P. J. et al. Roles for endoplasmic reticulum-associated degradation and the novel endoplasmic reticulum stress response gene Derlin-3 in the ischemic heart. *Circulation research* 106, 307-316, doi:10.1161/CIRCRESAHA.109.203901 (2010).

30. Lynch, J. M. et al. A thrombospondin-dependent pathway for a protective ER stress response. *Cell* 149, 1257-1268, doi:10.1016/j.cell.2012.03.050 (2012).

31. Rothermel, B. A. et al. Myocyte-enriched calcineurin-interacting protein, MCIP1, inhibits cardiac hypertrophy in vivo. *Proceedings of the National Academy of Sciences of the United States of America* 98, 3328-3333, doi:10.1073/pnas.041614798 (2001).

32. Belmont, P. J. et al. Coordination of growth and endoplasmic reticulum stress signaling by regulator of calcineurin 1 (RCAN1), a novel ATF6-inducible gene. *The Journal of biological chemistry* 283, 14012-14021, doi:10.1074/jbc. M709776200 (2008).

33. Papa, F. R. Endoplasmic reticulum stress, pancreatic beta-cell degeneration, and diabetes. *Cold Spring Harbor perspectives in medicine* 2, a007666, doi:10.1101/cshperspect.a007666 (2012).

34. Salvado, L., Palomer, X., Barroso, E. & Vazquez-Carrera, M. Targeting endoplasmic reticulum stress in insulin resistance. *Trends in endocrinology and metabolism: TEM* 26, 438-448, doi:10.1016/j.tem.2015.05.007 (2015).

35. Hotamisligil, G. S. Endoplasmic reticulum stress and the inflammatory basis of metabolic disease. *Cell* 140, 900-917, doi:10.1016/j.cell.2010.02.034 (2010).

36. Thameem, F., Farook, V. S., Bogardus, C. & Prochazka, M. Association of amino acid variants in the activating transcription factor 6 gene (ATF6) on 1q21-q23 with type 2 diabetes in Pima Indians. *Diabetes* 55, 839-842 (2006).

37. Teodoro-Morrison, T., Schuiki, I., Zhang, L., Belsham, D. D. & Volchuk, A. GRP78 overproduction in pancreatic beta cells protects against high-fat-diet-induced diabetes in mice. *Diabetologia* 56, 1057-1067, doi:10.1007/s00125-013-2855-7 (2013).

38. Cadavez, L. et al. Chaperones ameliorate beta cell dysfunction associated with human islet amyloid polypeptide overexpression. *PloS one* 9, e101797, doi:10.1371/journal.pone.0101797 (2014).

39. Ladiges, W. C. et al. Pancreatic beta-cell failure and diabetes in mice with a deletion mutation of the endoplasmic reticulum molecular chaperone gene P58IPK. *Diabetes* 54, 1074-1081 (2005).

40. Oyadomari, S. et al. Cotranslocational degradation protects the stressed endoplasmic reticulum from protein overload. *Cell* 126, 727-739, doi:10.1016/j.cell.2006.06.051 (2006).

41. Odisho, T., Zhang, L. & Volchuk, A. ATF6beta regulates the Wfs1 gene and has a cell survival role in the ER stress response in pancreatic beta-cells. *Experimental cell research* 330, 111-122, doi:10.1016/j.yexcr.2014.10.007 (2015).

42. Fonseca, S. G. et al. Wolfram syndrome 1 gene negatively regulates ER stress signaling in rodent and human cells. *The Journal of clinical investigation* 120, 744-755, doi:10.1172/JCI39678 (2010).

43. Engin, F. et al. Restoration of the unfolded protein response in pancreatic beta cells protects mice against type 1 diabetes. *Science translational medicine* 5, 211 ra156, doi:10.1126/scitranslmed.3006534 (2013).

44. Yang, L., Zhao, D., Ren, J. & Yang, J. Endoplasmic reticulum stress and protein quality control in diabetic cardiomyopathy. *Biochimica et biophysica acta* 1852, 209-218, doi:10.1016/j.bbadis.2014.05.006 (2015).

45. Zhang, Q. et al. ER stress and autophagy dysfunction contribute to fatty liver in diabetic mice. *International journal of biological sciences* 11, 559-568, doi:10.7150/ijbs.10690 (2015).

46. Lee, J. & Ozcan, U. Unfolded protein response signaling and metabolic diseases. *The Journal of biological chemistry* 289, 1203-1211, doi:10.1074/jbc. RI 13.534743 (2014).

47. Wang, Y., Vera, L., Fischer, W. H. & Montminy, M. The CREB coactivator CRTC2 links hepatic ER stress and fasting gluconeogenesis. *Nature* 460, 534-537, doi:10.1038/nature08111 (2009).

48. Rutkowski, D. T. et al. UPR pathways combine to prevent hepatic steatosis caused by ER stress-mediated suppression of transcriptional master regulators. *Developmental cell* 15, 829-840, doi:10.1016/j.devcel.2008.10.015 (2008).

49. Kammoun, H. L. et al. GRP78 expression inhibits insulin and ER stress-induced SREBP-1c activation and reduces hepatic steatosis in mice. *The Journal of clinical investigation* 119, 1201-1215, doi:10.1172/JCI37007 (2009).

50. Brandl, K. et al. Enhanced sensitivity to DSS colitis caused by a hypomorphic Mbtps1 mutation disrupting the ATF6-driven unfolded protein response. *Proceedings of the National Academy of Sciences of the United States of America* 106, 3300-3305, doi:10.1073/pnas.0813036106 (2009).

51. Ansar, M. et al. Mutation of ATF6 causes autosomal recessive achromatopsia. *Human genetics* 134, 941-950, doi:10.1007/s00439-015-1571-4 (2015).

52. Xu, M. et al. ATF6 Is Mutated in Early Onset Photoreceptor Degeneration With Macular Involvement. *Investigative ophthalmology & visual science* 56, 3889-3895, doi:10.1167/iovs.15-16778 (2015).

53. Kohl, S. et al. Mutations in the unfolded protein response regulator ATF6 cause the cone dysfunction disorder achromatopsia. *Nature genetics* 47, 757-765, doi:10.1038/ng.3319 (2015).

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating light chain amyloidosis in a patient afflicted therewith, comprising administering to the patient an effective amount of:

a compound of formula (I)

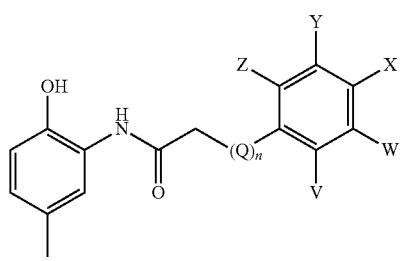

(I)

wherein Q is S, O, $CH_2$, CHF, or $CF_2$, n=1, 2, 3, or 4, when Q is $CH_2$, CHF, or $CF_2$;

n=1 when Q is S or O, and V, W, X, Y and Z are each independently hydrogen, halogen, alkyl, alkenyl, alkynyl, or alkoxy; or a pharmaceutically acceptable salt thereof.

2. The method of claim 1, wherein the compound of formula (I) is any one of

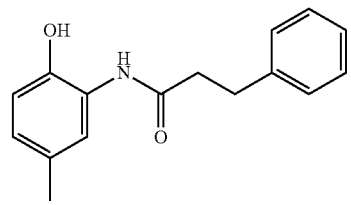

RP8

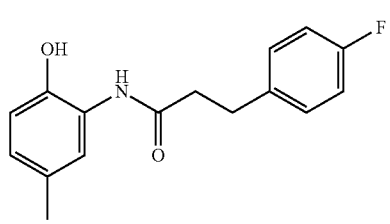

RP10

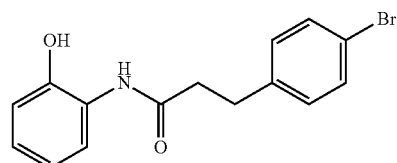

RP13

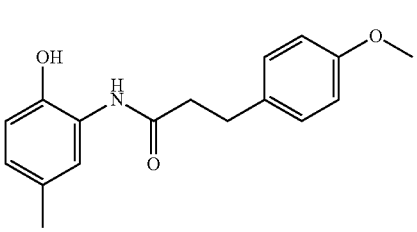

RP14

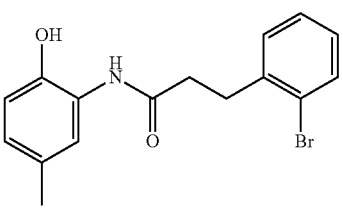

RP15

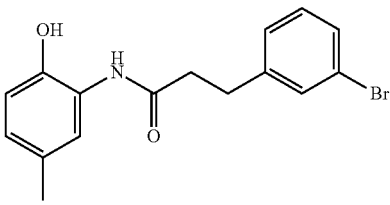

RP17

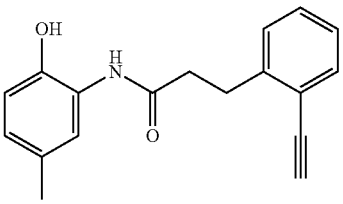

RP20

-continued
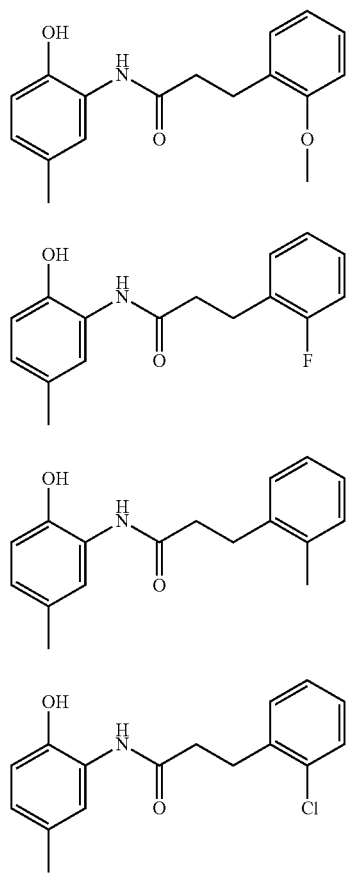
RP23
RP24
RP25
RP26
-continued
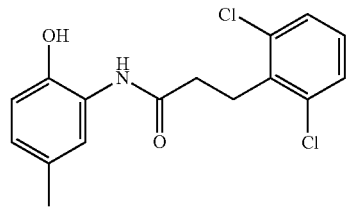
RP27
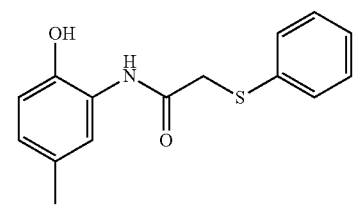
156
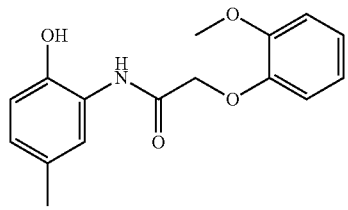
276
* * * * *

SEQUENCE LISTING

<160> NUMBER OF SEQ ID NOS: 8

<210> SEQ ID NO 1
<211> LENGTH: 36
<212> TYPE: DNA
<213> ORGANISM: Artificial Sequence
<220> FEATURE:
<223> OTHER INFORMATION: A synthetic primer

<400> SEQUENCE: 1
ctgaagaacg agcagtaagt gagcaagggc gaggag        36

<210> SEQ ID NO 2
<211> LENGTH: 43
<212> TYPE: DNA
<213> ORGANISM: Artificial Sequence
<220> FEATURE:
<223> OTHER INFORMATION: A synthetic primer

<400> SEQUENCE: 2
cgtacacctt ggaagcagat cttgaatctg aagagtcaat acc        43

<210> SEQ ID NO 3
<211> LENGTH: 44
<212> TYPE: DNA
<213> ORGANISM: Artificial Sequence
<220> FEATURE:
<223> OTHER INFORMATION: A synthetic primer

<400> SEQUENCE: 3
cggtattgac tcttcagatt caagatctgc ttccaaggtg tacg        44

<210> SEQ ID NO 4
<211> LENGTH: 36
<212> TYPE: DNA
<213> ORGANISM: Artificial Sequence
<220> FEATURE:
<223> OTHER INFORMATION: A synthetic primer

<400> SEQUENCE: 4
ctcctcgccc ttgctcactt actgctcgtt cttcag        36

<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
gtccaggctg gtgtcctctc        20

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
gattatcgga agccgtggag        20

<210> SEQ ID NO 7
<211> LENGTH: 20
<212> TYPE: DNA
<213> ORGANISM: Artificial Sequence

```
<220> FEATURE:
<223> OTHER INFORMATION: A synthetic primer

<400> SEQUENCE: 7
ccttgtagtt gagaaccagg                                               20

<210> SEQ ID NO 8
<211> LENGTH: 20
<212> TYPE: DNA
<213> ORGANISM: Artificial Sequence
<220> FEATURE:
<223> OTHER INFORMATION: A synthetic primer

<400> SEQUENCE: 8
gagtcaatac cgccagaatc                                               20
```